US011628159B2

(12) United States Patent
Abd Alla et al.

(10) Patent No.: US 11,628,159 B2
(45) Date of Patent: Apr. 18, 2023

(54) CELL-PROTECTIVE COMPOUNDS AND THEIR USE

(71) Applicant: ETH ZURICH, Zurich (CH)

(72) Inventors: Joshua Abd Alla, Zurich (CH); Stefan Wolf, Zurich (CH); Ursula Quitterer, Zurich (CH)

(73) Assignee: ETH ZURICH, Zurich (CH)

( * ) Notice: Subject to any disclaimer, the term of this patent is extended or adjusted under 35 U.S.C. 154(b) by 74 days.

(21) Appl. No.: 16/475,941

(22) PCT Filed: Jan. 10, 2018

(86) PCT No.: PCT/EP2018/050504
§ 371 (c)(1),
(2) Date: Jul. 3, 2019

(87) PCT Pub. No.: WO2018/130537
PCT Pub. Date: Jul. 19, 2018

(65) Prior Publication Data
US 2019/0343802 A1 Nov. 14, 2019

(30) Foreign Application Priority Data

Jan. 10, 2017 (EP) ..................................... 17150829

(51) Int. Cl.
| A61K 31/4025 | (2006.01) |
| A61K 31/416 | (2006.01) |
| A61K 31/4184 | (2006.01) |
| A61K 31/506 | (2006.01) |
| A61K 31/541 | (2006.01) |

(52) U.S. Cl.
CPC ........ *A61K 31/4025* (2013.01); *A61K 31/416* (2013.01); *A61K 31/4184* (2013.01); *A61K 31/506* (2013.01); *A61K 31/541* (2013.01)

(58) Field of Classification Search
CPC .............. A61K 31/4025; A61K 31/416; A61K 31/4184; A61K 31/506; A61K 31/541; A61P 9/00; A61P 9/10
See application file for complete search history.

(56) References Cited

U.S. PATENT DOCUMENTS

| 5,703,097 A | 12/1997 | Kim et al. |
| 2005/0234095 A1 | 10/2005 | Xie |
| 2005/0250808 A1 | 11/2005 | Xie et al. |
| 2008/0255200 A1 | 10/2008 | Gant |
| 2010/0256214 A1 | 10/2010 | Pasquale et al. |
| 2012/0237475 A1 | 9/2012 | Heiser et al. |
| 2018/0086768 A1 | 3/2018 | Jayarman |

FOREIGN PATENT DOCUMENTS

| EP | 1810969 B1 | 7/2007 |
| GB | 2372986 | * 9/2002 |
| JP | 2007145786 A | 6/2007 |
| WO | 1996033192 | 10/1996 |
| WO | 2003073999 A2 | 9/2003 |
| WO | 2004101495 A1 | 11/2004 |
| WO | 2007034846 A1 | 3/2007 |
| WO | 2007056582 A1 | 5/2007 |
| WO | 2009025477 A1 | 2/2009 |
| WO | 2009079011 A1 | 6/2009 |
| WO | 2013186229 A1 | 12/2013 |
| WO | 2014026327 A1 | 2/2014 |
| WO | 2015011396 A1 | 1/2015 |
| WO | 2017102091 A1 | 6/2017 |
| WO | 2017207534 A1 | 12/2017 |

OTHER PUBLICATIONS

Abd Alla et al., "Inhibition of G-protein-coupled Receptor Kinase 2 Prevents the Dysfunctional Cardiac Substrate Metabolism in Fatty Acid Synthase Transgenic Mice," J. Biol. Chem., 2016, vol. 291, No. 6, pp. 2583-2600.
Fu et al., "Inhibition of G-protein-coupled Receptor Kinase 2 (GRK2) Triggers the Growth-promoting Mitogen-activated Protein Kinase (MAPK) Pathway," Journal of Biological Chemistry, 2013, vol. 288, pp. 7739-7755.
Gros et al., "G-Protein-coupled Receptor Kinase Activity Is Increased in Hypertension," J. Clin. Invest., 1997, vol. 99, No. 9, pp. 2087-2093.
Hullmann et al., "The Expanding GRK Interactome: Implications in Cardiovascular Disease and Potential for Therapeutic Development," Pharmacol. Res., 2016, vol. 110, pp. 52-64.
Jaber et al., "Essential role of b-adrenergic receptor kinase 1 in cardiac development and function," PNAS USA, 1996, vol. 93, pp. 12974-12979.
Koch et al., "Cardiac function in mice overexpressing the beta-adrenergic receptor kinase or a beta ARK inhibitor," Science, 1995, vol. 268(5215), pp. 1350-1353.
Medina et al., "Aminoindazole PDK1 Inhibitors: A Case Study in Fragment-Based Drug Discovery," ACS Med. Chem. Lett., 2010, vol. 1, No. 8, pp. 439-442.

(Continued)

*Primary Examiner* — Barbara P Badio
(74) *Attorney, Agent, or Firm* — Bryan D. Zerhusen, Esq.; Nicholas R. Herrel, Esq.; Cantor Colburn LLP

(57) ABSTRACT

The present invention is directed to cell-protective, in particular, cardio- and renal-protective organic compounds, preferably to organic compounds that inhibit substrate phosphorylation by the G-protein-coupled receptor kinase 2 (GRK2, ADRBK1). Preferably, the organic compounds inhibit the GRK2-mediated phosphorylation of serine/arginine-rich splicing factor 1 (SRSF1, ASF-1, SF2) and/or phosducin for treating hypertension, heart diseases, heart dysfunction or failure and heart disease-associated pathologies, e.g. cardiomyocyte necrosis, ischemic cardiac disease and/or ischemic heart damage or ageing. Furthermore, the present invention is directed to a method for the identification of inhibitors of the (GRK2)-mediated phosphorylation of (SRSF1) and/or phosducin.

17 Claims, 24 Drawing Sheets

Figure 2:
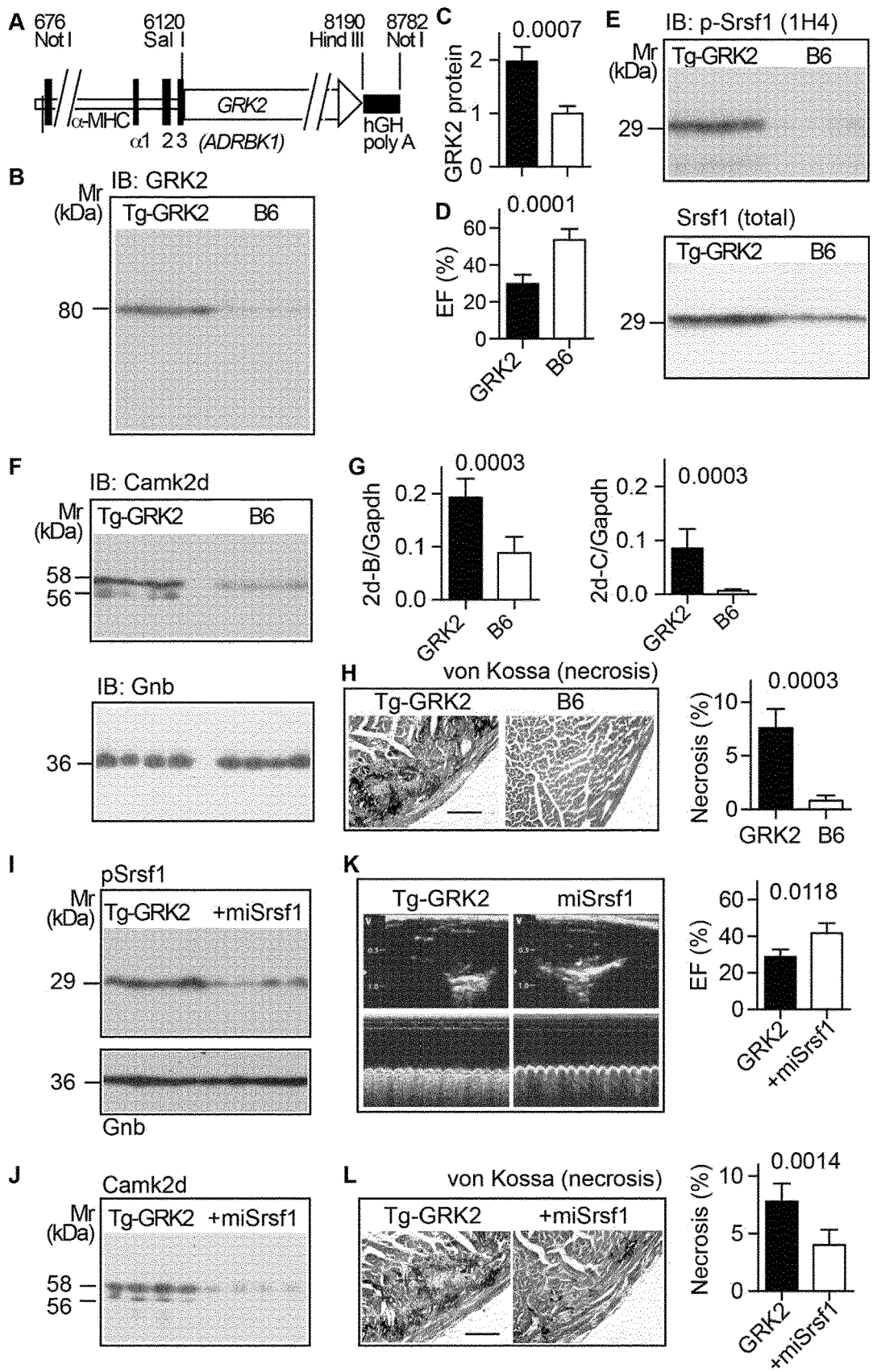

Specification includes a Sequence Listing.

(56) References Cited

OTHER PUBLICATIONS

Pegklidou et al., "N-substituted Pyrrole-based Scaffolds as Potential Anticancer and Antiviral Lead Structures," Medicinal Chemistry, 2015, vol. 11, No. 6, pp. 602-608.
Schumacher et al., "Paroxetine-mediated GRK2 inhibition reverses cardiac dysfunction and remodeling after myocardial infarction," Science Translational Medicine, 2015, vol. 7, Issue 277, pp. 1-11.
Thal et al., "Paroxetine Is a Direct Inhibitor of G Protein-Coupled Receptor Kinase 2 and Increases Myocardial Contractility," ACS Chem. Biol., 2012, vol. 7, No. 11, pp. 1830-1839.
Uguz et al., "Weight gain and associated factors in patients using newer antidepressant drugs," General Hospital Psychiatry, 2015, vol. 37, Issue 1, pp. 46-48.
Ungerer et al., "Altered Expression of ,B-Adrenergic Receptor Kinase and B1-Adrenergic Receptors in the Failing Human Heart," Circulation, 1993, vol. 87, pp. 454-463.
Volkers et al., "The Inotropic Peptide BARKct Improves BAR Responsiveness in Normal and Failing Cardiomyocytes Through Gby-Mediated L-Type Calcium Current Disinhibition," Circulation Research, 2011, vol. 108, pp. 27-39.
Waldschmidt et al., "Structure-Based Design, Synthesis, and Biological Evaluation of Highly Selective and Potent G Protein-Coupled Receptor Kinase 2 Inhibitors," J. Med. Chem., 2016, vol. 59, pp. 3793-3807.
Winstel et al., "Peptide inhibitors of G protein-coupled receptor kinases," Biochem. Pharmacol., 2005, vol. 70, pp. 1001-1008.
International Search Report and Written Opinion for PCT/EP2018/050504 dated Jun. 22, 2018.

* cited by examiner

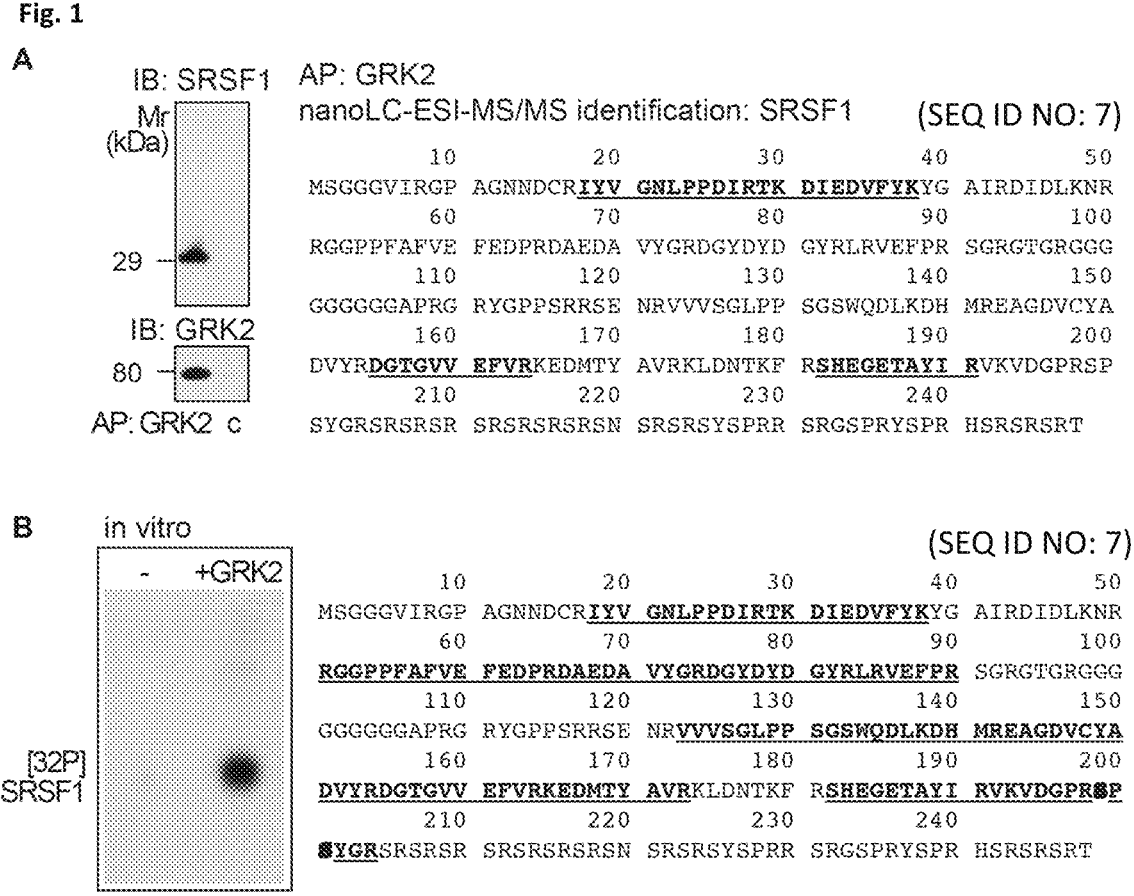

Fig. 1B (Continued)

(SEQ ID NO: 8)

| | | | | | | | | |
|---|---|---|---|---|---|---|---|---|
| 1276 | 192-204 | 499.9112 | 1496.7119 | 1496.7137 | -1.18 | 2 | 26 | 0.27 | 1 | U | R.VKVDGPRSPSYGR.S + Phospho (ST) |
| 1277 | 192-204 | 749.3638 | 1496.7130 | 1496.7137 | -0.47 | 2 | 37 | 0.023 | 1 | U | R.VKVDGPRSPSYGR.S + Phospho (ST) |
| 1278 | 192-204 | 499.9116 | 1496.7130 | 1496.7137 | -0.46 | 2 | 34 | 0.048 | 1 | U | R.VKVDGPRSPSYGR.S + Phospho (ST) |
| 1279 | 192-204 | 499.9117 | 1496.7132 | 1496.7137 | -0.33 | 2 | 35 | 0.037 | 1 | U | R.VKVDGPRSPSYGR.S + Phospho (ST) |
| 1280 | 192-204 | 499.3641 | 1496.7136 | 1496.7137 | -0.036 | 2 | 36 | 0.036 | 1 | U | R.VKVDGPRSPSYGR.S + Phospho (ST) |

(SEQ ID NO: 9)

| | | | | | | | | |
|---|---|---|---|---|---|---|---|---|
| 1064 | 194-204 | 424.1903 | 1269.5490 | 1269.5503 | -1.04 | 1 | 34 | 0.031 | 1 | U | K.VDGPRSPSYGR.S + Phospho (ST) |
| 1065 | 194-204 | 424.1903 | 1269.5491 | 1269.5503 | -0.95 | 1 | 22 | 0.47 | 1 | U | K.VDGPRSPSYGR.S + Phospho (ST) |
| 1066 | 194-204 | 635.7819 | 1269.5492 | 1269.5503 | -0.91 | 1 | 23 | 0.44 | 1 | U | K.VDGPRSPSYGR.S + Phospho (ST) |
| 1067 | 194-204 | 635.7820 | 1269.5495 | 1269.5503 | -0.61 | 1 | 31 | 0.058 | 1 | U | K.VDGPRSPSYGR.S + Phospho (ST) |
| 1068 | 194-204 | 635.7821 | 1269.5496 | 1269.5503 | -0.58 | 1 | 28 | 0.12 | 1 | U | K.VDGPRSPSYGR.S + Phospho (ST) |

Fig. 1
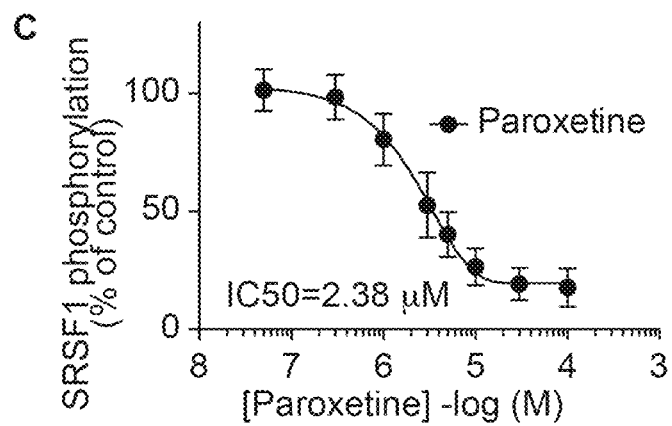
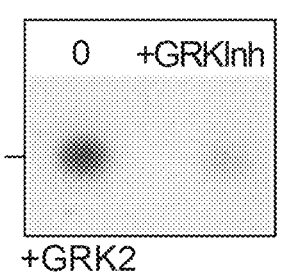
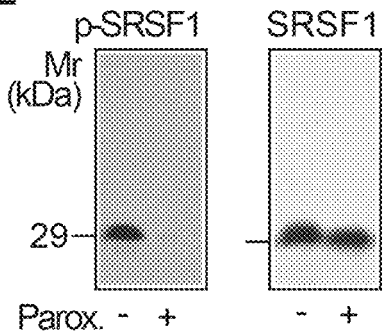

Fig. 7
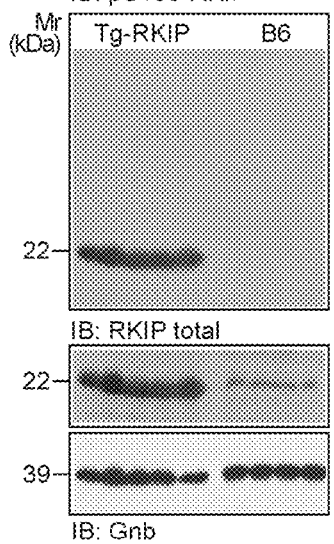
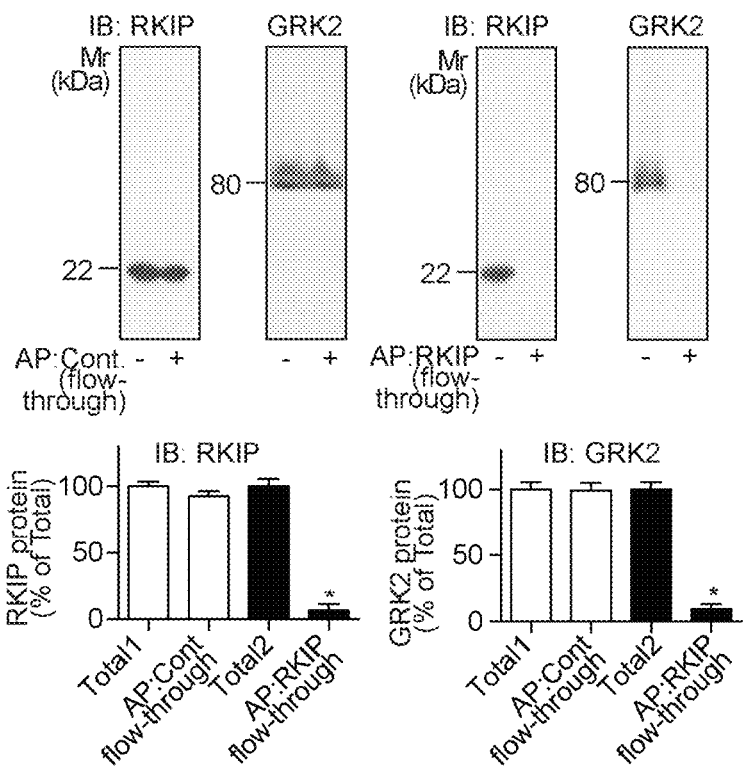
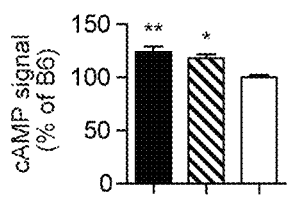
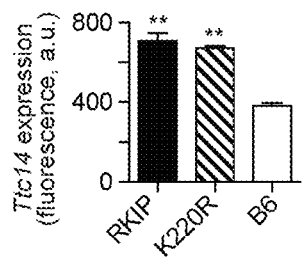
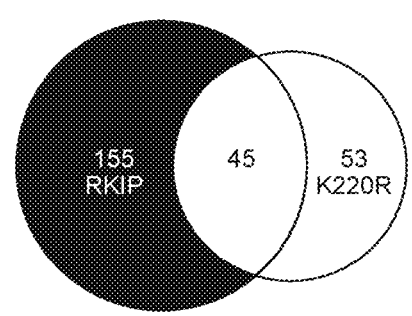
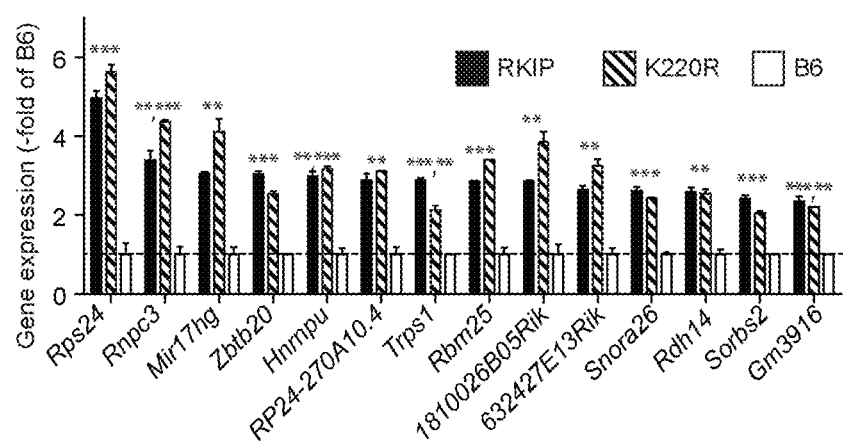

Figure 13B:
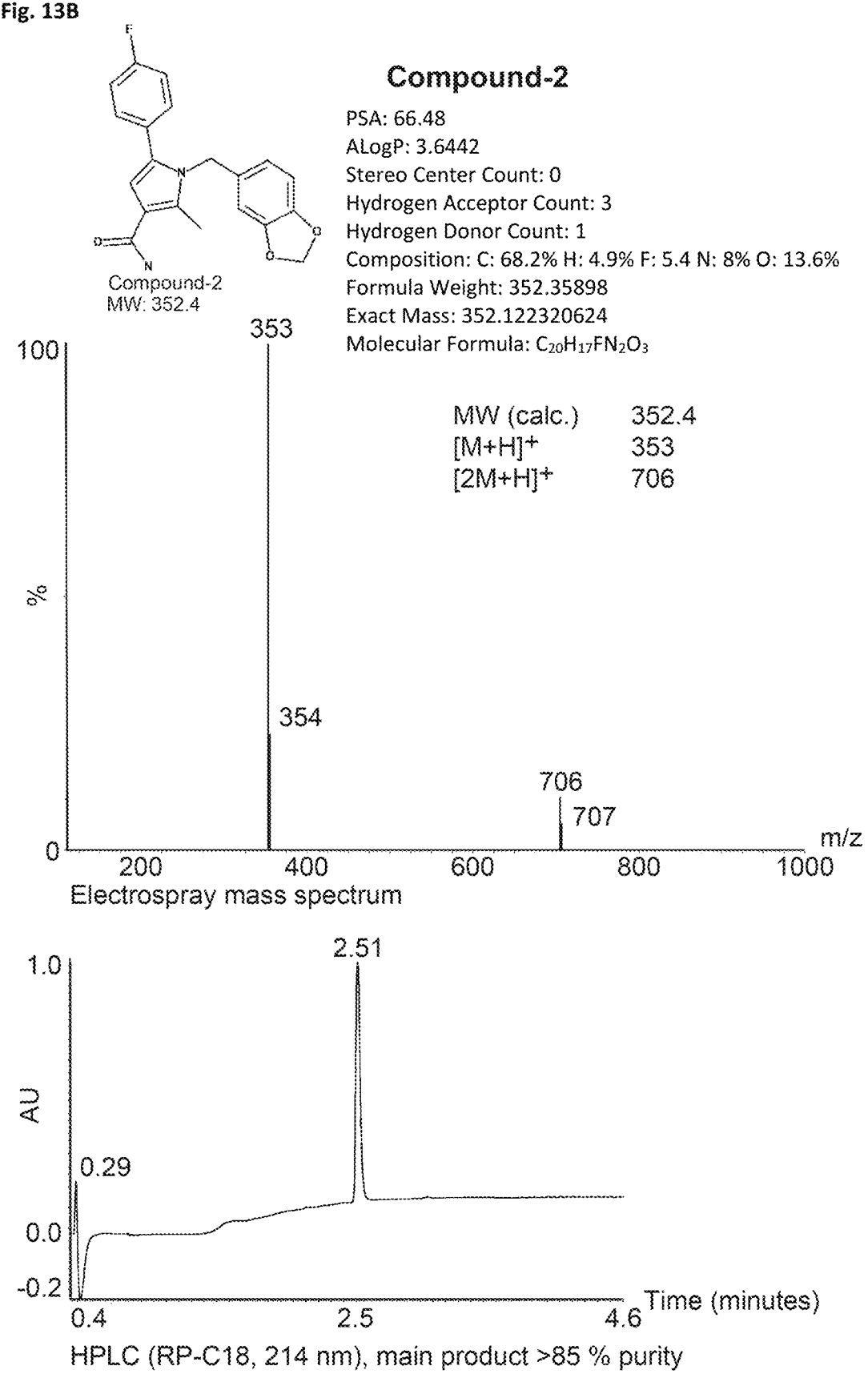
Figure 13G:
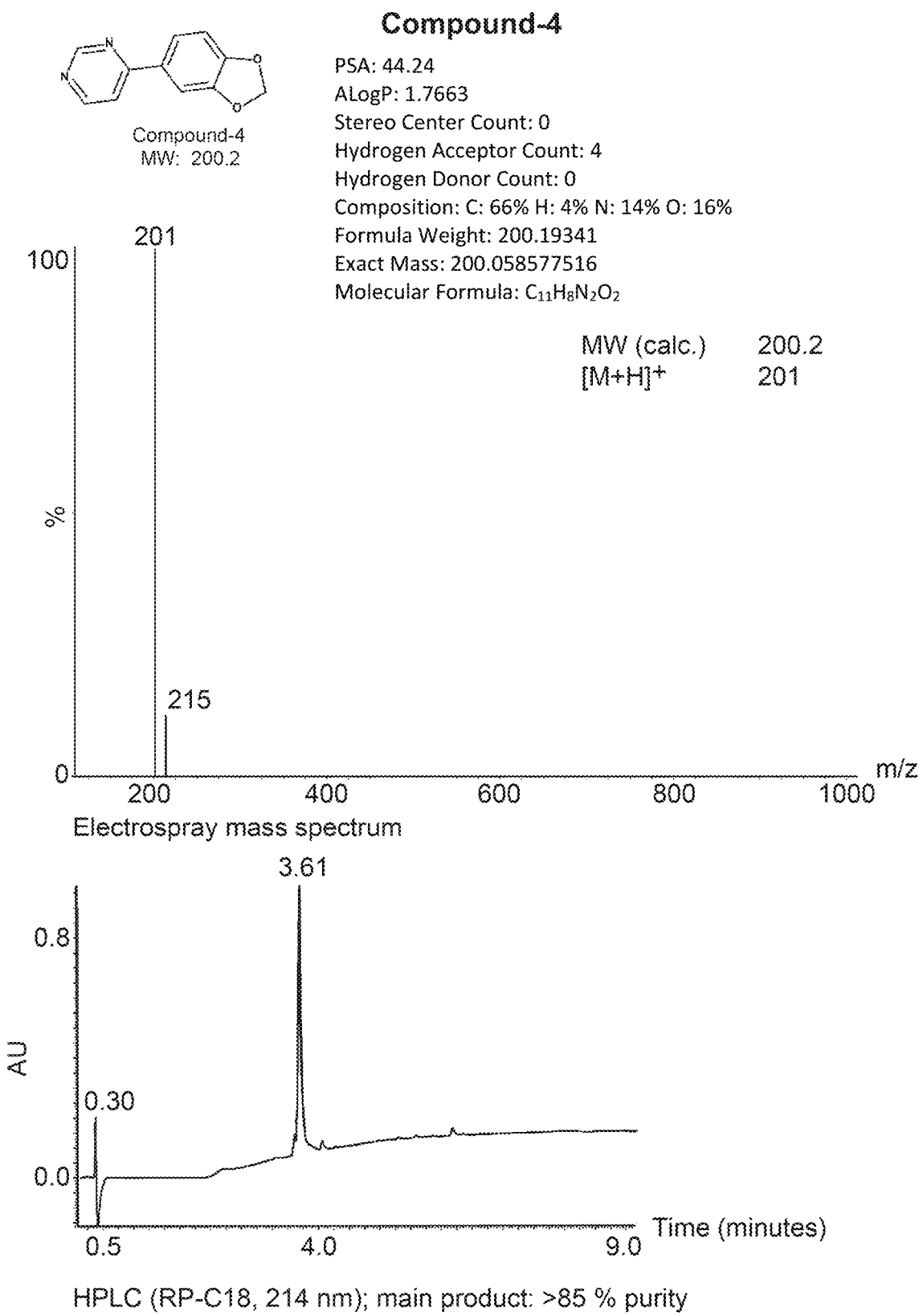
Figure 13I:
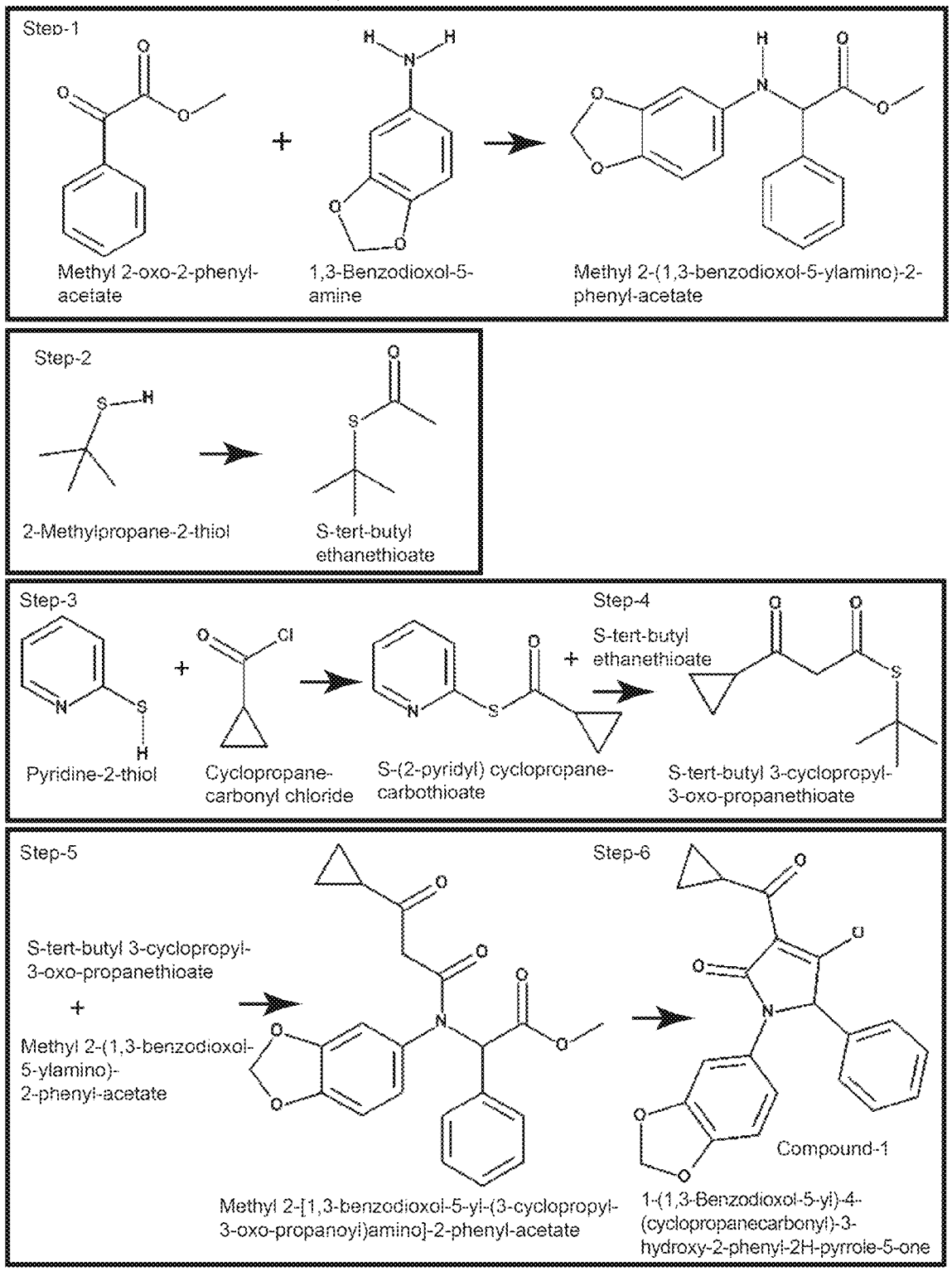
Figure 13J:
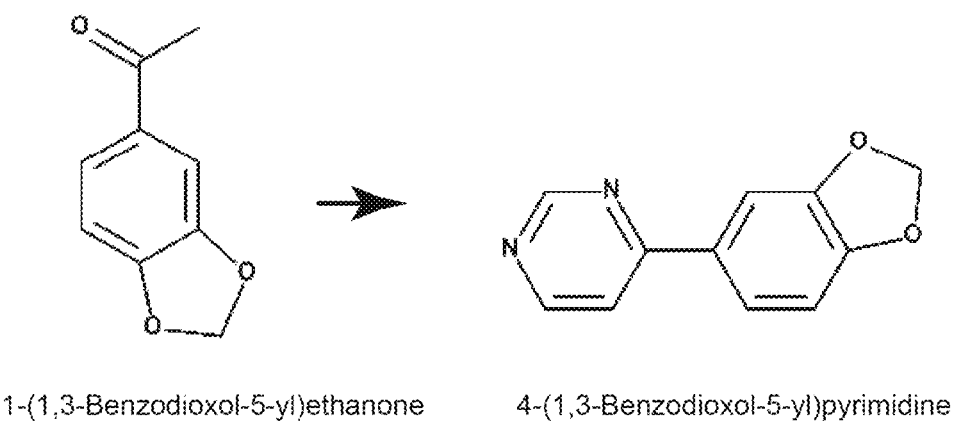

Fig. 13A
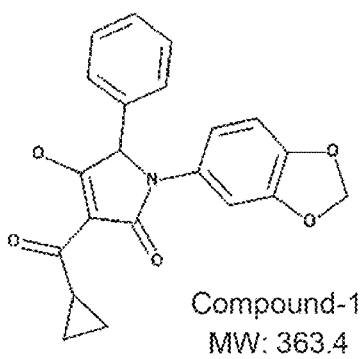
Compound-1
MW: 363.4
Compound-1
PSA: 76.07
ALogP: 2.8144
Stereo Center Count: 1
Hydrogen Acceptor Count: 5
Hydrogen Donor Count: 1
Composition: C: 69.4% H: 4.7% N: 3.9% O: 22%
Formula Weight: 363.36337
Exact Mass: 363.110672654
Molecular Formula: $C_{21}H_{17}NO_5$
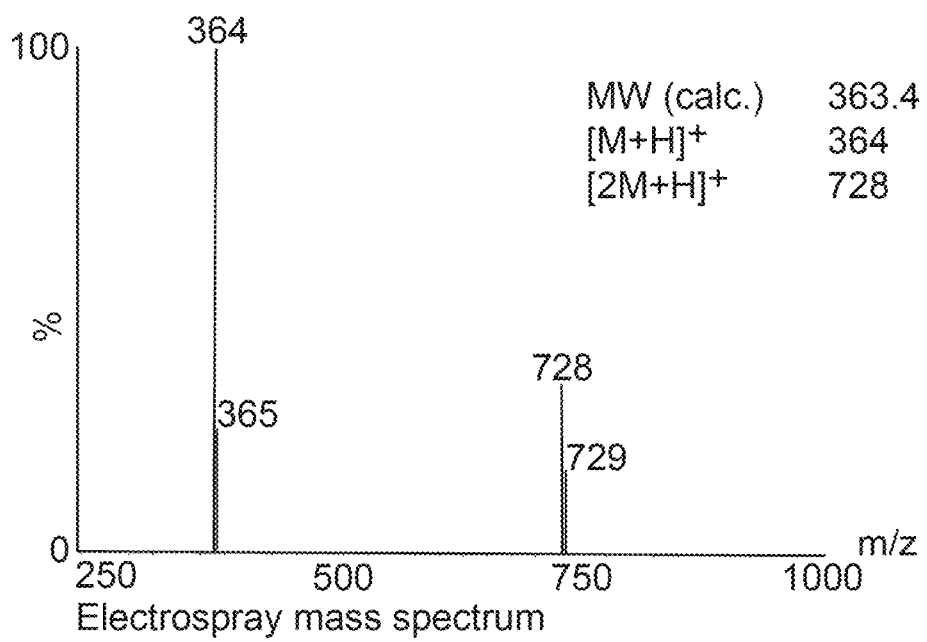
MW (calc.)     363.4
$[M+H]^+$      364
$[2M+H]^+$     728
Electrospray mass spectrum
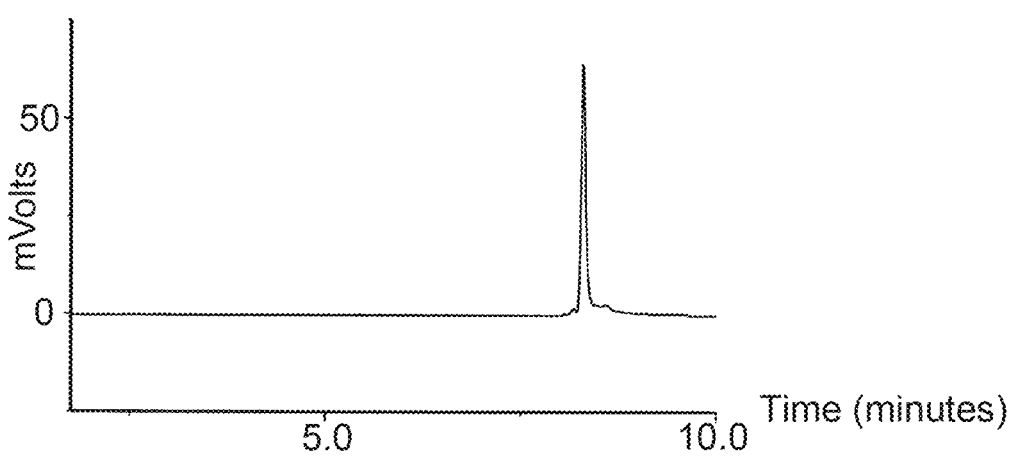
HPLC (RP-C18, 214 nm); main product: >85 % purity

Compound-2

PSA: 66.48
ALogP: 3.6442
Stereo Center Count: 0
Hydrogen Acceptor Count: 3
Hydrogen Donor Count: 1
Composition: C: 68.2% H: 4.9% F: 5.4 N: 8% O: 13.6%
Formula Weight: 352.35898
Exact Mass: 352.122320624
Molecular Formula: $C_{20}H_{17}FN_2O_3$

| | |
|---|---|
| MW (calc.) | 352.4 |
| $[M+H]^+$ | 353 |
| $[2M+H]^+$ | 706 |

Electrospray mass spectrum

HPLC (RP-C18, 214 nm), main product >85 % purity

Fig. 13C
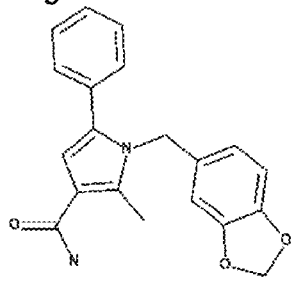
Compound-22
MW: 334.4
Compound-22
PSA: 66.48
ALogP: 3.4387
Stereo Center Count: 0
Hydrogen Acceptor Count: 3
Hydrogen Donor Count: 1
Composition: C: 71.8% H: 5.4% N: 8.4% O: 14.4%
Formula Weight: 334.36851
Exact Mass: 334.131742456
Molecular Formula: $C_{20}H_{18}N_2O_3$
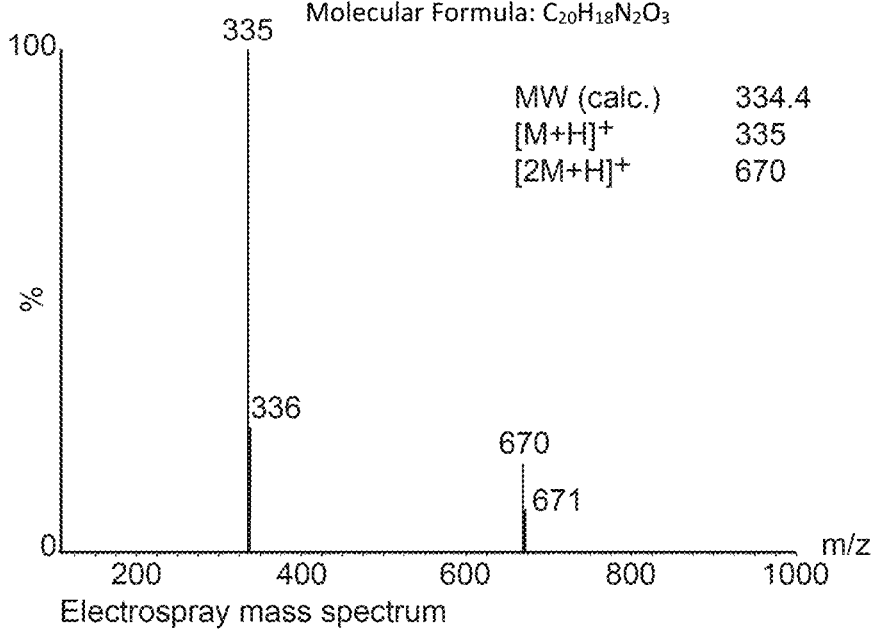
| | |
|---|---|
| MW (calc.) | 334.4 |
| $[M+H]^+$ | 335 |
| $[2M+H]^+$ | 670 |
Electrospray mass spectrum
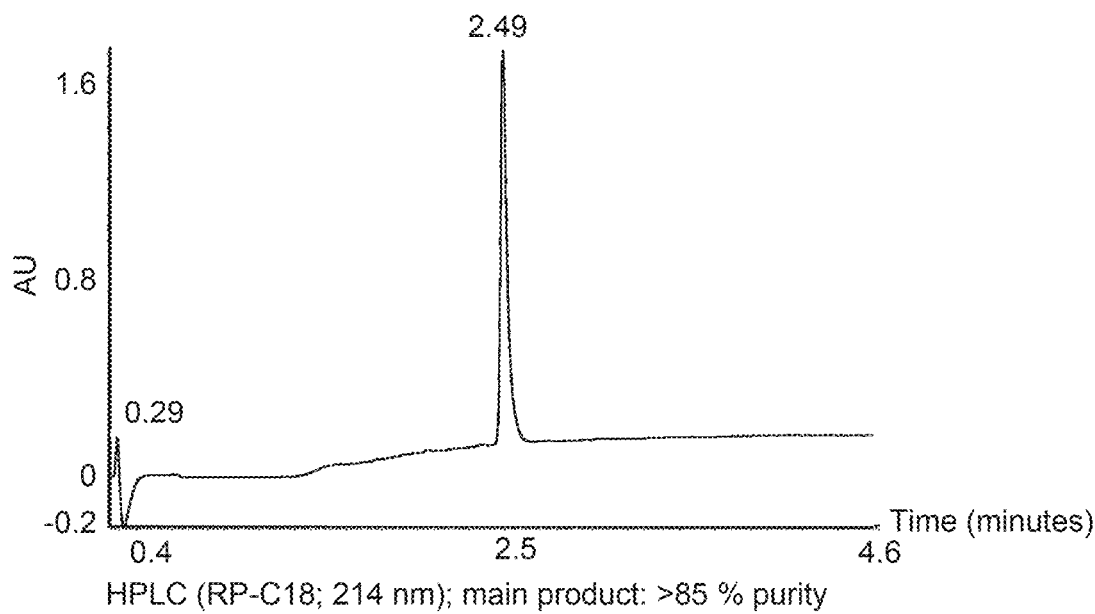
HPLC (RP-C18; 214 nm); main product: >85 % purity

Fig. 13D
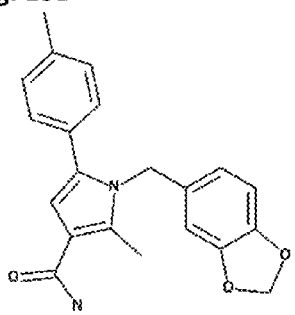
Compound-23
MW: 348.4
Compound-23
PSA: 66.48
ALogP: 3.9249
Stereo Center Count: 0
Hydrogen Acceptor Count: 3
Hydrogen Donor Count: 1
Composition: C: 72.4% H: 5.8% N: 8% O: 13.8%
Formula Weight: 348.39509
Exact Mass: 348.14739252
Molecular Formula: $C_{21}H_{20}N_2O_3$
| | |
|---|---|
| MW (calc.) | 348.4 |
| $[M+H]^+$ | 349 |
| $[2M+H]^+$ | 698 |
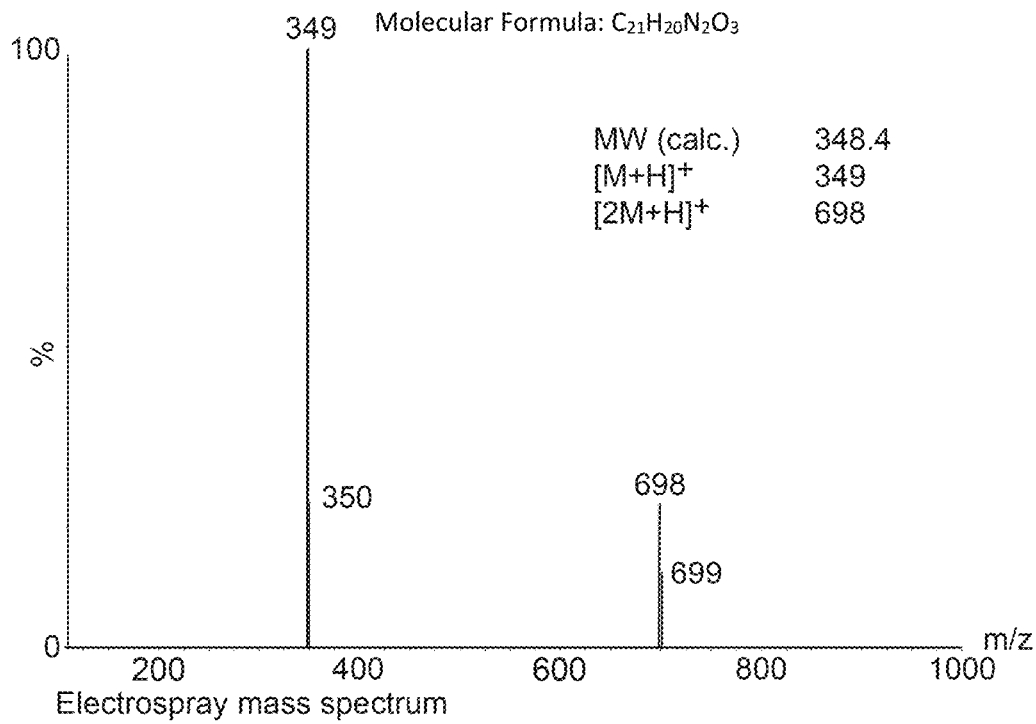
Electrospray mass spectrum
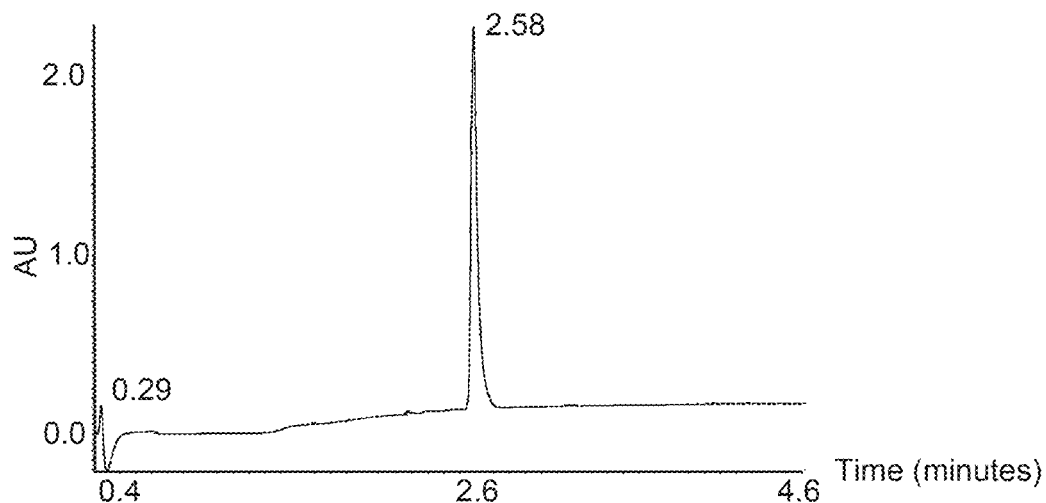
HPLC (RP-C18; 214 nm); main product: > 85 % purity Fig. 13E
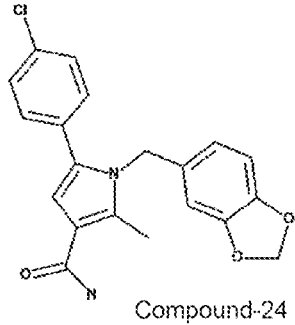
Compound-24
MW: 368.8
Compound-24
PSA: 66.48
ALogP: 4.1031
Stereo Center Count: 0
Hydrogen Acceptor Count: 3
Hydrogen Donor Count: 1
Composition: C: 65.1% H: 4.6% Cl: 9.6% N: 7.6% O: 13%
Formula Weight: 368.81357
Exact Mass: 368.092770134
Molecular Formula: $C_{20}H_{17}ClN_2O_3$
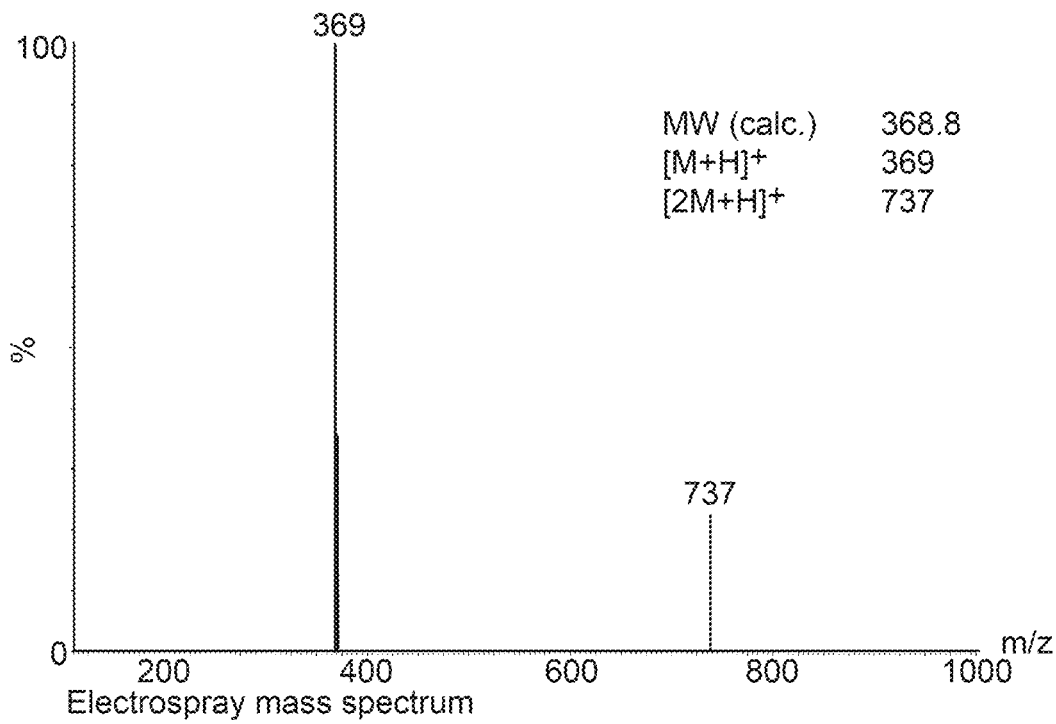
| | |
|---|---|
| MW (calc.) | 368.8 |
| $[M+H]^+$ | 369 |
| $[2M+H]^+$ | 737 |
Electrospray mass spectrum
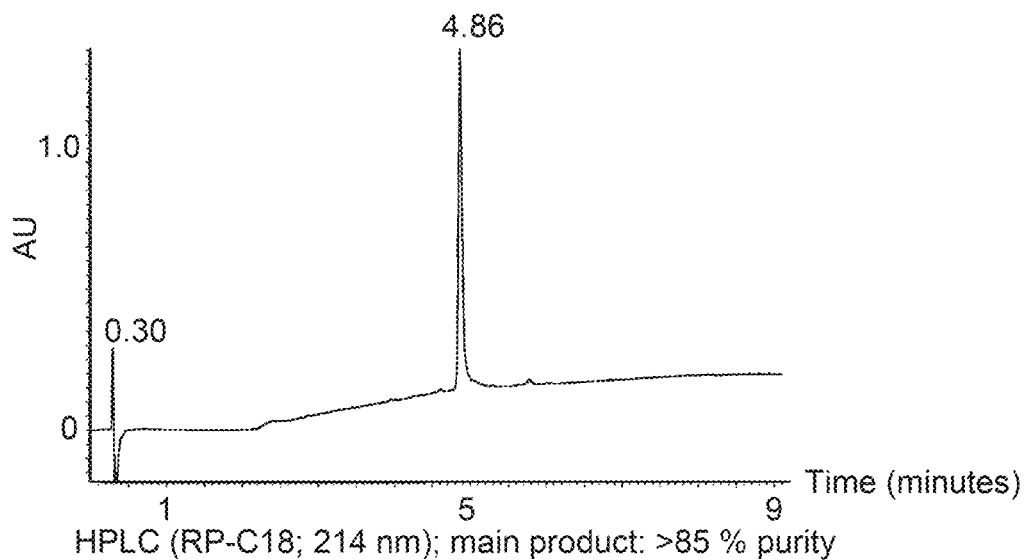
HPLC (RP-C18; 214 nm); main product: >85 % purity Fig. 13F
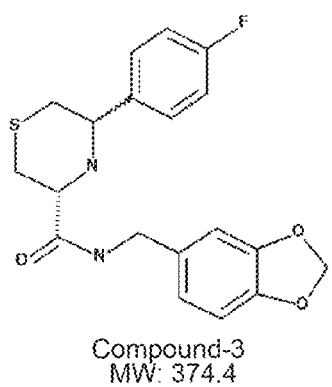
Compound-3
MW: 374.4
Compound-3
PSA: 84.89
ALogP: 2.5811
Stereo Center Count: 2
Hydrogen Acceptor Count: 5
Hydrogen Donor Count: 2
Composition: C: 60.9% H: 5.1% F: 5.1% N: 7.5% O: 12.8% S: 8.6%
Formula Weight: 374.42916
Exact Mass: 374.110041378
Molecular Formula: $C_{19}H_{19}FN_2O_3S$
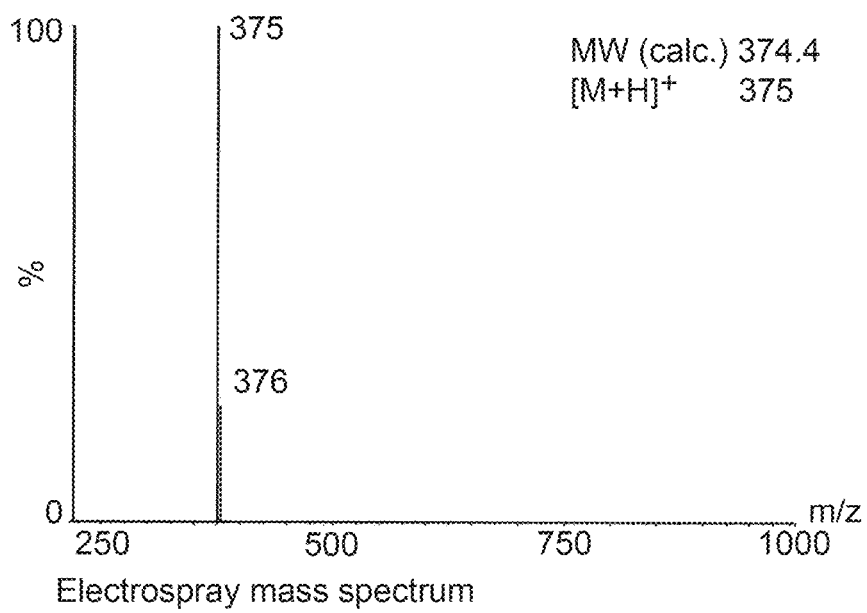
MW (calc.) 374.4
$[M+H]^+$ 375
Electrospray mass spectrum
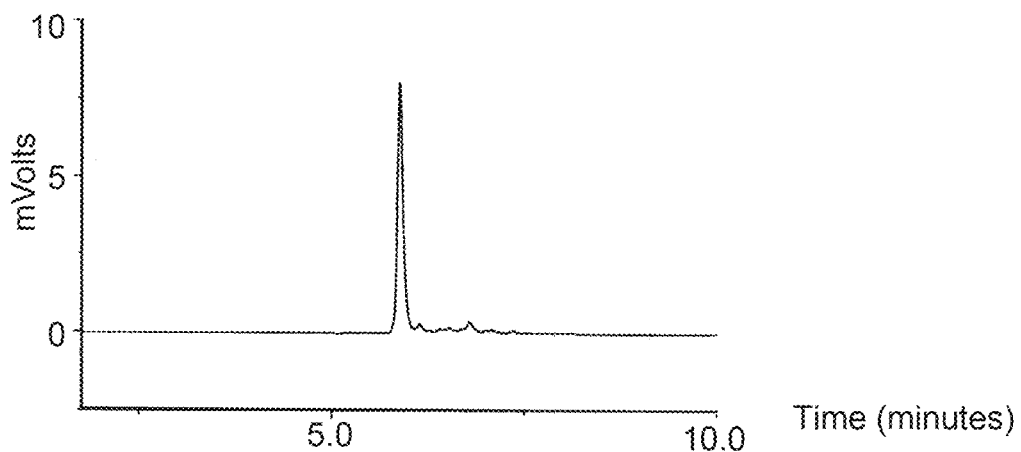
HPLC (RP-C18, 214 nm); main product: >85 % purity Fig. 13H
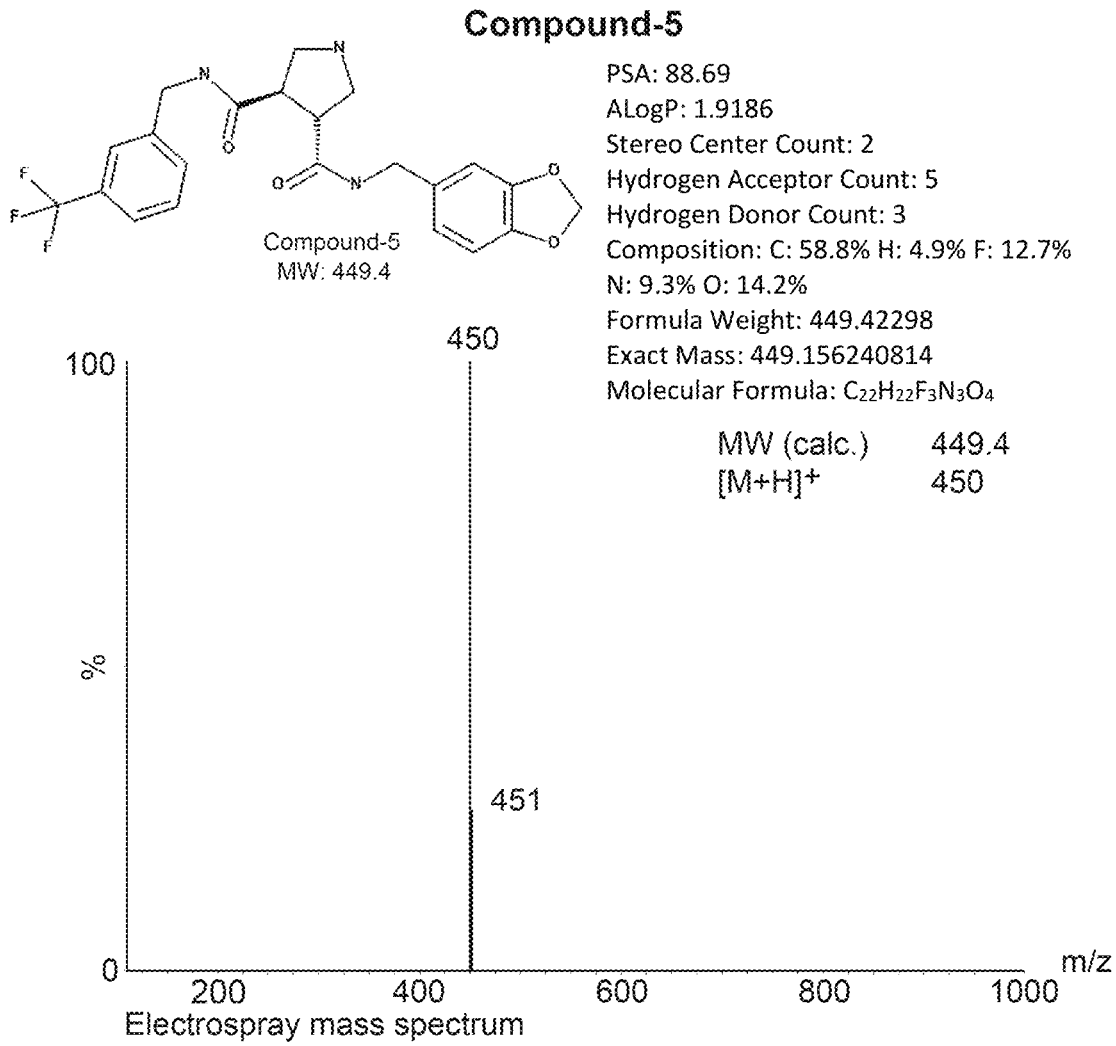
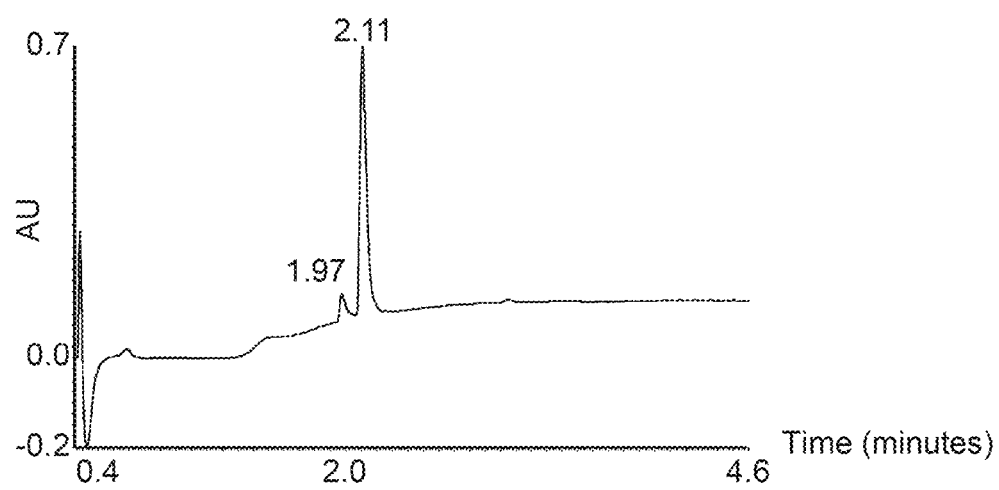
HPLC (RP-C18, 214 nm); main product: > 85 % purity Synthesis of Compound-4

1-(1,3-Benzodioxol-5-yl)ethanone     4-(1,3-Benzodioxol-5-yl)pyrimidine

CELL-PROTECTIVE COMPOUNDS AND THEIR USE

RELATED APPLICATIONS

The present application is a National Stage of PCT/EP2018/050504, filed 10 Jan. 2018, titled CELL-PROTECTIVE COMPOUNDS AND THEIR USE, published as International Patent Application Publication No. WO 2018/130537, which claims the benefit and priority to European Application No. 17150829.4, filed on 10 Jan. 2017, both of which are incorporated herein by reference in their entirety for all purposes.

Incorporate by Reference

In compliance with 37 C.F.R. § 1.52(e)(5), the sequence information contained in electronic file name: 50572PCT_Sequence Listing ST25_v_27 12 2017.txt; size 6.54 KB; created on: 27 Dec. 2017 and confirmed via Checker 4.4.0 is hereby incorporated herein by reference in its entirety."

The present invention is directed to cell-protective, in particular, cardio- and renal-protective organic compounds, preferably to organic compounds that inhibit substrate phosphorylation by the G-protein-coupled receptor kinase 2 (GRK2, ADRBK1). Preferably, the organic compounds inhibit the GRK2-mediated phosphorylation of serine/arginine-rich splicing factor 1 (SRSF1, ASF-1, SF2) and/or phosducin for treating heart diseases, hypertension, heart dysfunction or failure and heart disease-associated pathologies, e.g. cardiomyocyte necrosis, ischemic cardiac disease and/or ischemic heart damage and ageing. Furthermore, the present invention is directed to a method for the identification of inhibitors of the GRK2-mediated phosphorylation of SRSF1 and/or phosducin.

Cardiovascular disease and heart failure are the most frequent causes of death and, thus, there is an urgent need for new treatment approaches. Established pharmacological therapies for cardiovascular disease include, e.g. beta-blockers, inhibitors of the angiotensin II AT1 system, ACE inhibitors, mineralcorticoid receptor blockers and the combined neprilysin-AT1 receptor blockers sacubitril-valsartan. Despite these available therapies, the prognosis of patients with end-stage heart failure is worse than that of most cancer patients.

Inhibition of the G-protein-coupled receptor kinase 2 (GRK2, ADRBK1, betaARK) has been connected to cardioprotection in experimental models for heart disease and heart failure (Hullmann et al., Pharmacol. Res. 110, 52-64 (2016); Abd Alla, et al., J. Biol. Chem. 291, 2583-2600 (2016)), and GRK2 is up-regulated in patients with cardiovascular disease and hypertension (Ungerer et al., Circulation 87, 454-463 (1993); Gros et al., J. Clin. Invest. 99, 2087-2093 (1997)).

One approach used the betaARK-C-terminus, which inhibits GRK2-mediated receptor phosphorylation by scavenging the activating betagamma subunits of heterotrimeric G-proteins (Koch et al., Science 268, 1350-1353 (1995); U.S. Pat. No. 7,060,871).

However, the betaARK-C-terminus did not reach clinical studies because it is a large protein of 194 amino acids, which is difficult to administer and requires a gene therapeutic approach to reach its intracellular target, the GRK2. Moreover, the betaATRK-C-terminus also inhibits activities of G-betagamma subunits, which have multiple other relevant functions in vivo. In agreement with this statement, the cardio-protective effect of the BetaARK-C-terminus in vivo involves also GRK2 inhibition-independent mechanisms (Volkers M, et al., Circ. Res. 108, 27-39 (2011)).

Compounds which were identified by an in silico screening for interaction with the Gbeta subunit of heterotrimeric G-proteins have also shown to increase cardiac contractility similarly as the BetaARK-C-terminus (WO 2004/101495 A1). But this approach is also not specific for GRK2 and is expected to interfere with other Gbeta-gamma-mediated functions similarly as does the BetaARK-C-terminus. These compounds were not further characterized and did not reach clinical studies.

Another scientific investigation concerned GRKInh, a peptidic inhibitor of GRK2 (18 amino acids), which is derived from the first intracellular loop of the beta2-adrenergic receptor (Winstel et al., Biochem. Pharmacol. 70, 1001-1008 (2005)). GRKinh is cardio-protective in vivo (Abd Alla et al., J. Biol. Chem. 291, 2583-2600 (2016); Fu et al., J. Biol. Chem. 288, 7739-7755 (2013)). However, to date, the binding site of GRKInh on GRK2 is not determined, and GRKInh is a peptide, which is difficult to administer and requires a gene therapeutic approach to reach its intracellular target, the GRK2. Moreover, GRKInh is an immunogenic peptide, which could trigger an auto-immune response against the beta2-adrenergic receptor.

Paroxetine is an ATP-site-directed kinase inhibitor of GRK2 (Thal et al., ACS Chem. Biol. 7, 1830-1839 (2012); Schumacher et al., Sci. Transl. Med. 7, 277ra31 (2015)). The fact that paroxetine (i) is non-specific for GRK2, (ii) has a low inhibitory activity for GRK2, (iii) has a different major high-affinity target, the serotonine transporter, and (iv) causes weight gain, renders paroxetine not suitable for cardio-protective therapy (Uguz et al., Gen Hosp Psychiatry 46-48, 37 (2015).

Other ATP-site-directed GRK2 inhibitors, e.g. the Takeda compounds, which have high affinity and selectivity for GRK2 (WO 2007/034846 A1) were not tested in vivo and cardio-protective properties are not known. Also, Waldschmidt et al. (J. Med. Chem. 59, 3793-3807 (2016)) report GRK2 inhibitors. However, all these high affinity GRK2-specific ATP-site-directed kinase inhibitors block all functions of GRK2 and may have major side effects because GRK2 exerts an indispensable role in vivo, which cannot be compensated, i.e. the knockout of GRK2 is lethal (Jaber et al., PNAS USA 93, 12974-12979 (1996)). In addition, in vivo effects of the Takeda or Waldschmidt compounds are not documented and off-target effects as well as the bioavailability of the compounds are not known.

In summary, to date no new approach for cardio-protective treatment reached clinical studies. Lack of suitable targets, specificity and/or the occurrence of side effects of available inhibitors for given targets are a major problem. Moreover, the mechanism underlying many therapy approaches, e.g. the cardio-protective effect of GRK2 inhibition, as well as its actual suitability for cardio-protective treatment, are still discussed controversially in the prior art.

The problem underlying the present invention is the provision of new and/or improved cell-protective, preferably cardio- and renal-protective compounds, preferably for use in medical and/or in cell-protective, preferably cardio- and/or renal-protective treatment.

In a first aspect the problem underlying the present invention is solved by a compound according to Formula (I) or (II):

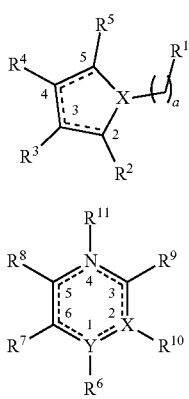

Formula (I)

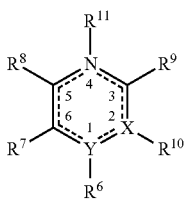

Formula (II)

wherein:
the dotted lines between positions (2), (3), (4) and (5) in Formula (I) and between positions (1), (2), (3), (4), (5) and (6) in Formula (II) represent single bonds or double bonds between the respective positions;
X is selected from the group consisting of N and C;
Y is selected from the group consisting of S and C, with the proviso that when Y is C, X is N;
a is an integer between 0 and 15, preferably between 0 and 10, more preferably between 0 and 5, most preferably is 0 or 1;
$R^1$ is selected from the group consisting of
  (i) hydrogen, hydroxyl, F, Cl, Br and oxo, preferably if X is not N or if X is N and a is not 0, $R^1$ is selected from the group consisting of hydroxyl, F, Cl, Br and oxo;
  (ii) linear or branched, substituted or non-substituted $(C_{1-10})$alkyl ether, $(C_{2-10})$alkenyl ether, $(C_{2-10})$alkynyl ether and $(C_{4-10})$carbocyclic ether;
  (iii) linear or branched, substituted or non-substituted $(C_{1-10})$alkyl, preferably $(C_{1-5})$alkyl, more preferably methyl, ethyl and propyl, most preferably methyl, $(C_{2-10})$alkenyl and $(C_{2-10})$alkynyl;
  (iv) substituted or non-substituted carbocycle selected from the group consisting of $(C_{3-10})$carbocycle, preferably $(C_3)$carbocycle and $(C_{5-6})$carbocycle, preferably aromatic $(C_6)$carbocycle, more preferably a non-substituted phenyl and a para-substituted phenyl that is substituted by a substituent selected from the group consisting of Cl, F, Br, substituted or non-substituted methyl, preferably —(CF$_3$), ethyl, propyl and cyclopropyl; and
  (v) substituted or non-substituted $(C_{3-6})$heterocycle and $(C_7-C_{10})$carbo- or heterobicycle having 1 to 3 heteroatoms each independently selected from N, O and S, preferably substituted or non-substituted $(C_7)$heterobicycle having 2 heteroatoms selected from N and S, more preferably substituted or non-substituted indazolyl, benzimidazolyl and benzodioxolyl, preferably indazolyl, benzimidazolyl and benzodioxolyl connected via position (5) or (6), more preferably via position (6) of the indazolyl or benzodioxolyl or position (5) of the benzimidazolyl;
$R^2$ is selected from the group consisting of
  (i) hydrogen, hydroxyl, O—$R^{14}$, —O—C(=O)—$R^{14}$, F, Cl, Br and oxo wherein $R^{14}$ is selected from the group consisting of
    (aa) linear or branched, substituted or non-substituted $(C_{1-10})$alkyl, preferably $(C_{1-5})$alkyl, more preferably methyl, ethyl and propyl, most preferably methyl, $(C_{2-10})$alkenyl, and $(C_{2-10})$alkynyl;
    (bb) substituted or non-substituted aromatic or non-aromatic $(C_{3-10})$carbocycle, preferably $(C_{3-6})$cycloalkyl, more preferably $(C_3)$carbocycle and $(C_6)$carbocycle, preferably $(C_6)$carbocycle, more preferably phenyl that is mono-substituted in para position by $(C_3)$carbocycle or —(CF$_3$) or di-substituted in meta position by $(C_3)$carbocycle or —(CF$_3$); and
    (cc) substituted or non-substituted aromatic or non-aromatic, preferably aromatic, $(C_{3-6})$heterocycle having 1 to 3 heteroatoms each independently selected from N, O and S;
  (ii) linear or branched, substituted or non-substituted $(C_{1-10})$alkyl, preferably $(C_{1-5})$alkyl, more preferably methyl, ethyl and propyl, most preferably methyl, $(C_{2-10})$alkenyl, $(C_{2-10})$alkynyl, and $(C_{3-10})$carbocycle, preferably $(C_{3-6})$cycloalkyl;
  (iii) linear or branched, substituted or non-substituted $(C_{1-10})$alkyl ether, $(C_{2-10})$alkenyl ether, $(C_{2-10})$alkynyl ether and $(C_{4-10})$carbocyclic ether; and
  (iv) substituted or non-substituted $(C_{3-6})$heterocycle and $(C_7-C_{10})$carbo- or heterobicycle having 1 to 3 heteroatoms each independently selected from N, O and S, preferably substituted or non-substituted $(C_7)$heterobicycle having 2 heteroatoms selected from N and S, more preferably substituted or non-substituted indazolyl, benzimidazolyl and benzodioxolyl, preferably indazolyl, benzimidazolyl and benzodioxolyl connected via position (5) or (6) of the indazolyl, benzodioxolyl or benzimidazolyl;
$R^3$ and $R^4$ are independently selected from the group consisting of
  (i) hydrogen, —O—$R^{14}$, —O—C(=O)—$R^{14}$, F, Cl, Br and oxo, wherein $R^{14}$ is selected from the group consisting of
    (aa) linear or branched, substituted or non-substituted $(C_{1-10})$alkyl, preferably $(C_{1-5})$alkyl, more preferably methyl, ethyl and propyl, most preferably methyl, $(C_{2-10})$alkenyl, and $(C_{2-10})$alkynyl;
    (bb) substituted or non-substituted aromatic or non-aromatic $(C_{3-10})$carbocycle, preferably $(C_{3-6})$cycloalkyl, more preferably $(C_3)$carbocycle and $(C_6)$carbocycle, preferably $(C_6)$carbocycle, more preferably phenyl that is mono-substituted in para position by $(C_3)$carbocycle or —(CF$_3$) or di-substituted in meta position by $(C_3)$carbocycle or —(CF$_3$); and
    (cc) substituted or non-substituted aromatic or non-aromatic, preferably aromatic, $(C_{3-6})$heterocycle having 1 to 3 heteroatoms each independently selected from N, O and S;
  (ii) linear or branched, substituted or non-substituted $(C_{1-10})$alkyl, preferably $(C_{1-5})$alkyl, more preferably methyl, ethyl and propyl, most preferably methyl, $(C_{2-10})$alkenyl, $(C_{2-10})$alkynyl and $(C_{3-10})$carbocycle, preferably substituted or non-substituted $(C_{3-6})$cycloalkyl and $(C_{3-6})$heterocycle having 1 to 3 heteroatoms each independently selected from N, O and S;
  (iii) linear or branched, substituted or non-substituted $(C_{1-10})$alkyl ether, $(C_{2-10})$alkenyl ether, $(C_{2-10})$alkynyl ether and $(C_{4-10})$carbocyclic ether;

(iv)

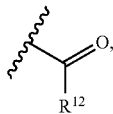

wherein $R^{12}$ is selected from the group consisting of
- (aa) hydrogen, hydroxyl, substituted or non-substituted N, F, Cl and Br;
- (bb) linear or branched, substituted or non-substituted $(C_{1-10})$alkyl, preferably $(C_{1-5})$alkyl, more preferably methyl, ethyl and propyl, most preferably methyl, $(C_{2-10})$alkenyl, and $(C_{2-10})$alkynyl;
- (cc) substituted or non-substituted aromatic or non-aromatic $(C_{3-10})$carbocycle, preferably $(C_{3-6})$cycloalkyl, more preferably $(C_3)$carbocycle and $(C_6)$carbocycle, preferably $(C_6)$carbocycle, more preferably phenyl that is mono-substituted in para position by $(C_3)$carbocycle or —$(CF_3)$ or di-substituted in meta position by $(C_3)$carbocycle or —$(CF_3)$; and
- (dd) substituted or non-substituted aromatic or non-aromatic, preferably aromatic, $(C_{3-6})$heterocycle having 1 to 3 heteroatoms each independently selected from N, O and S; and (v)

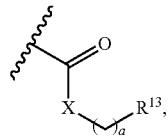

wherein X is N or C, a is an integer between 0 and 15, preferably between 0 and 10, more preferably between 0 and 5, most preferably is 0 or 1, and $R^{13}$ is selected from the group consisting of
- (aa) hydrogen, hydroxyl, F, Cl and Br;
- (bb) linear or branched, substituted or non-substituted $(C_{1-10})$alkyl, preferably $(C_{1-5})$alkyl, more preferably methyl, ethyl and propyl, most preferably methyl, $(C_{2-10})$alkenyl and $(C_{2-10})$alkynyl;
- (cc) substituted or non-substituted $(C_{3-10})$carbocycle, preferably $(C_{3-6})$cycloalkyl, $(C_{7}-C_{10})$carbo- or heterobicycle and $(C_{3-6})$heterocycle having 1 to 3 heteroatoms each independently selected from N, O and S, more preferably, for $R^3$, $R^{13}$ is $(C_7)$heterobicycle having 2 heteroatoms selected from N and S, most preferably substituted or non-substituted indazolyl, benzimidazolyl and benzodioxolyl, preferably indazolyl, benzimidazolyl and benzodioxolyl connected via position (5) or (6), more preferably via position (5) of the indazolyl and benzodioxolyl or position (6) of the benzimidazolyl, and
  - most preferably, for $R^4$, $R^{13}$ is substituted or non-substituted aromatic $(C_6)$carbocycle, preferably $(C_6)$carbocycle that is mono- or di-substituted in meta position by $(C_3)$-carbocycle or —$(CF_3)$, or mono-substituted in para position by $(C_3)$-carbocycle or —$(CF_3)$; and
- (dd) linear or branched, substituted or non-substituted $(C_{1-10})$alkyl ether, $(C_{2-10})$alkenyl ether, $(C_{2-10})$alkynyl ether and $(C_{4-10})$carbocyclic ether;

wherein, if positions (2), (3) and/or (4) of the ring of Formula (I) are sp³-hybridized, $R^2$ and $R^4$ and/or $R^3$ and $R^4$ are preferably in cis or trans configuration to each other, more preferably in trans configuration, preferably, $R^2$ is (R)- or (S)-, $R^3$ is (R)- or (S)- and/or $R^4$ is (R)- or (S)-configured, more preferably, $R^2$ is (R)-, $R^3$ is (R)- and/or $R^4$ is (R)-configured, or $R^2$ is (S)-, $R^3$ is (S)- and/or $R^4$ is (S)-configured.

$R^5$ and $R^9$ are selected from the group consisting of
- (i) hydrogen, hydroxyl, F, Cl, Br and oxo, with the proviso that $R^9$ is not oxo if X is N and Y is C;
- (ii) linear or branched, substituted or non-substituted $(C_{1-10})$alkyl ether, $(C_{2-10})$alkenyl ether, $(C_{2-10})$alkynyl ether and $(C_{4-10})$carbocyclic ether;
- (iii) linear or branched, substituted or non-substituted $(C_{1-10})$alkyl, preferably $(C_{1-5})$alkyl, more preferably methyl, ethyl and propyl, most preferably methyl, $(C_{2-10})$alkenyl and $(C_{2-10})$alkynyl;
- (iv) substituted or non-substituted $(C_{3-10})$carbocycle, preferably substituted or non-substituted $(C_3)$carbocycle, substituted or non-substituted aromatic $(C_{5-6})$carbocycle, more preferably cyclopenta-2,4-dien-1-yl and aromatic $(C_6)$carbocycle, most preferably phenyl that is non-substituted or substituted in para position by a substituent selected from the group consisting of Cl, F, Br, substituted or non-substituted methyl, preferably —$(CF_3)$, ethyl, propyl and cyclopropyl; and
- (v) $(C_{3-6})$heterocycle having 1 to 3 heteroatoms each independently selected from N, O and S, preferably substituted or non-substituted imidazolyl and pyrazolyl, more preferably imidazolyl and pyrazolyl connected via imidazolyl-/pyrazolyl-position-(1)-nitrogen to the rings of Formula (I);

wherein, if position (5) of the ring of Formula (I) is sp³-hybridized, $R^5$ is preferably (S)- or (R)-configured, more preferably (R)-configured;

and wherein, if position (3) of the ring of Formula (II) is sp³-hybridized, $R^9$ is preferably (S)- or (R)-configured, more preferably (S)-configured;

$R^6$ and $R^{11}$ are independently selected from the group consisting of
- (i) linear or branched, substituted or non-substituted $(C_{1-10})$alkyl ether, $(C_{2-10})$alkenyl ether, $(C_{2-10})$alkynyl ether and $(C_{4-10})$carbocyclic ether;
- (ii) linear or branched, substituted or non-substituted $(C_{1-10})$alkyl, preferably $(C_{1-5})$alkyl, more preferably methyl, ethyl and propyl, most preferably methyl, $(C_{2-10})$alkenyl and $(C_{2-10})$alkynyl;
- (iii) substituted or non-substituted carbocycle selected from the group consisting of $(C_{3-10})$carbocycle, preferably $(C_3)$carbocycle and $(C_{5-6})$carbocycle, more preferably aromatic $(C_6)$carbocycle, most preferably phenyl that is non-substituted or mono- or di-substituted in meta and para position by a substituent selected from the group consisting of Cl, F, Br, substituted or non-substituted methyl, ethyl, propyl and cyclopropyl; and
- (iv) substituted or non-substituted $(C_{3-6})$heterocycle and $(C_7-C_{10})$carbo- or heterobicycle having 1 to 3 heteroatoms each independently selected from N, O and S, preferably substituted or non-substituted $(C_7)$heterobicycle having 2 heteroatoms selected from N and S, most preferably substituted or non-substituted indazolyl, benzimidazolyl and benzodioxolyl, preferably indazolyl, benzimidazolyl and benzodioxolyl connected via position (5) or (6), more preferably via position (6) of the indazolyl or benzodioxolyl or position (5) of the benzimidazolyl, wherein R⁶ is not present if Y is S; and/or
wherein R¹¹ is absent if the ring of Formula (II) has a double bond between positions (4) and (5) or between positions (3) and (4) of the ring of Formula (II), and with the proviso that R⁶ is not 1,2,4-triazolyl if X is N, Y is C and the ring of Formula (II) is aromatic;

R⁷ is selected from the group consisting of
  (i) hydrogen, hydroxyl, F, Cl, Br and oxo;
  (ii) linear or branched, substituted or non-substituted (C₁₋₁₀)alkyl, preferably (C₁₋₅)alkyl, more preferably methyl, ethyl and propyl, most preferably methyl, (C₂₋₁₀)alkenyl, (C₂₋₁₀)alkynyl and (C₃₋₁₀)carbocycle, preferably (C₃₋₆)cycloalkyl and (C₃₋₆)heterocycle having 1 to 3 heteroatoms each independently selected from N, O and S;
  (iii) linear or branched, substituted or non-substituted (C₁₋₁₀)alkyl ether, (C₂₋₁₀)alkenyl ether, (C₂₋₁₀)alkynyl ether and (C₄₋₁₀)carbocyclic ether; and
  (iv)

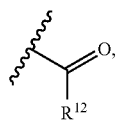

wherein R¹² is selected from the group consisting of
  (aa) hydrogen, hydroxyl, substituted or non-substituted N, F, Cl and Br;
  (bb) linear or branched, substituted or non-substituted (C₁₋₁₀)alkyl, preferably (C₁₋₅)alkyl, more preferably methyl, ethyl and propyl, most preferably methyl, (C₂₋₁₀)alkenyl, (C₂₋₁₀)alkynyl and aromatic or non-aromatic (C₃₋₁₀)carbocycle, preferably (C₃₋₆)cycloalkyl, more preferably (C₃)carbocycle, most preferably aromatic (C₆)carbocycle that is mono-substituted in para position by (C₃)carbocycle or —(CF₃) or di-substituted in meta position by (C₃)carbocycle or —(CF₃); and
  (cc) substituted or non-substituted, aromatic or non-aromatic, preferably aromatic, (C₃₋₆)heterocycle having 1 to 3 heteroatoms each independently selected from N, O and S;

R⁸ is selected from the group defined above for R⁷, the group further comprising
  (i)

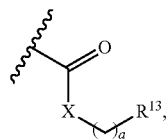

wherein X is N or C, a is an integer between 0 and 15, preferably between 0 and 10, more preferably between 0 and 5, most preferably is 0 or 1, and R¹³ is selected from the group consisting of
  (aa) hydrogen, hydroxyl, F, Cl and Br;
  (bb) linear or branched, substituted or non-substituted (C₁₋₁₀)alkyl, preferably (C₁₋₅)alkyl, more preferably methyl, ethyl and propyl, most preferably methyl, (C₂₋₁₀)alkenyl and (C₂₋₁₀)alkynyl;
  (cc) substituted or non-substituted (C₃₋₁₀)carbocycle, preferably (C₃₋₆)cycloalkyl, (C₇-C₁₀)carbo- or heterobicycle and (C₃₋₆)heterocycle having 1 to 3 heteroatoms each independently selected from N, O and S, more preferably substituted or non-substituted (C₇)heterobicycle having 2 heteroatoms selected from N and S, most preferably substituted or non-substituted indazolyl, benzimidazolyl and benzodioxolyl, preferably indazolyl and benzodioxolyl connected via position (5) or (6), more preferably via position (5) of the indazolyl and benzodioxolyl or position (6) of the benzimidazolyl, most preferably substituted or non-substituted aromatic (C₆)carbocycle, preferably (C₆)carbocycle that is mono- or di-substituted in meta position by (C₃)-carbocycle or —(CF₃) or mono-substituted in para position by (C₃)-carbocycle or —(CF₃); and
  (dd) linear or branched, substituted or non-substituted (C₁₋₁₀)alkyl ether, (C₂₋₁₀)alkenyl ether, (C₂₋₁₀)alkynyl ether and (C₄₋₁₀)carbocyclic ether;

with the proviso that R⁸ is not 1,2,4-triazolyl if X is N, Y is C and the ring of Formula (II) is aromatic,
and wherein, if position (5) of the ring of Formula (II) is sp³-hybridized, R⁸ is preferably (R)- or (S)-configured, more preferably (R)-configured;

R¹⁰ is absent or selected from the group consisting of
  (i) hydrogen;
  (ii) methyl; and
  (iii) cyclopropyl or phenyl that is mono-substituted in para position by a substituent selected from the group consisting of H, Cl, F, Br, methyl, —(CF₃) and cyclopropyl;

wherein one or more of R², R³, R⁴, R⁵, R⁶, R⁷, R⁸, R⁹, R¹⁰ and R¹¹ are either directly attached to the rings of Formulas (I) or (II) or are attached to a linker between R², R³, R⁴, R⁵, R⁶, R⁷, R⁸, R⁹, R¹⁰ and/or R¹¹ and the rings of Formulas (I) or (II), wherein the linker is selected from the group consisting of linear or branched, substituted or non-substituted (C₁₋₁₀)alkyl ether, (C₂₋₁₀)alkenyl ether, (C₂₋₁₀)alkynyl ether, (C₄₋₁₀) carbocyclic ether, linear or branched, substituted or non-substituted (C₁₋₁₀)alkyl, (C₂₋₁₀)alkenyl and (C₂₋₁₀) alkynyl;

and pharmaceutically acceptable salts or solvates thereof;
for use in medical treatment, preferably in cell-protective, more preferably cardio- and/or renal-protective treatment.

Figure 3:
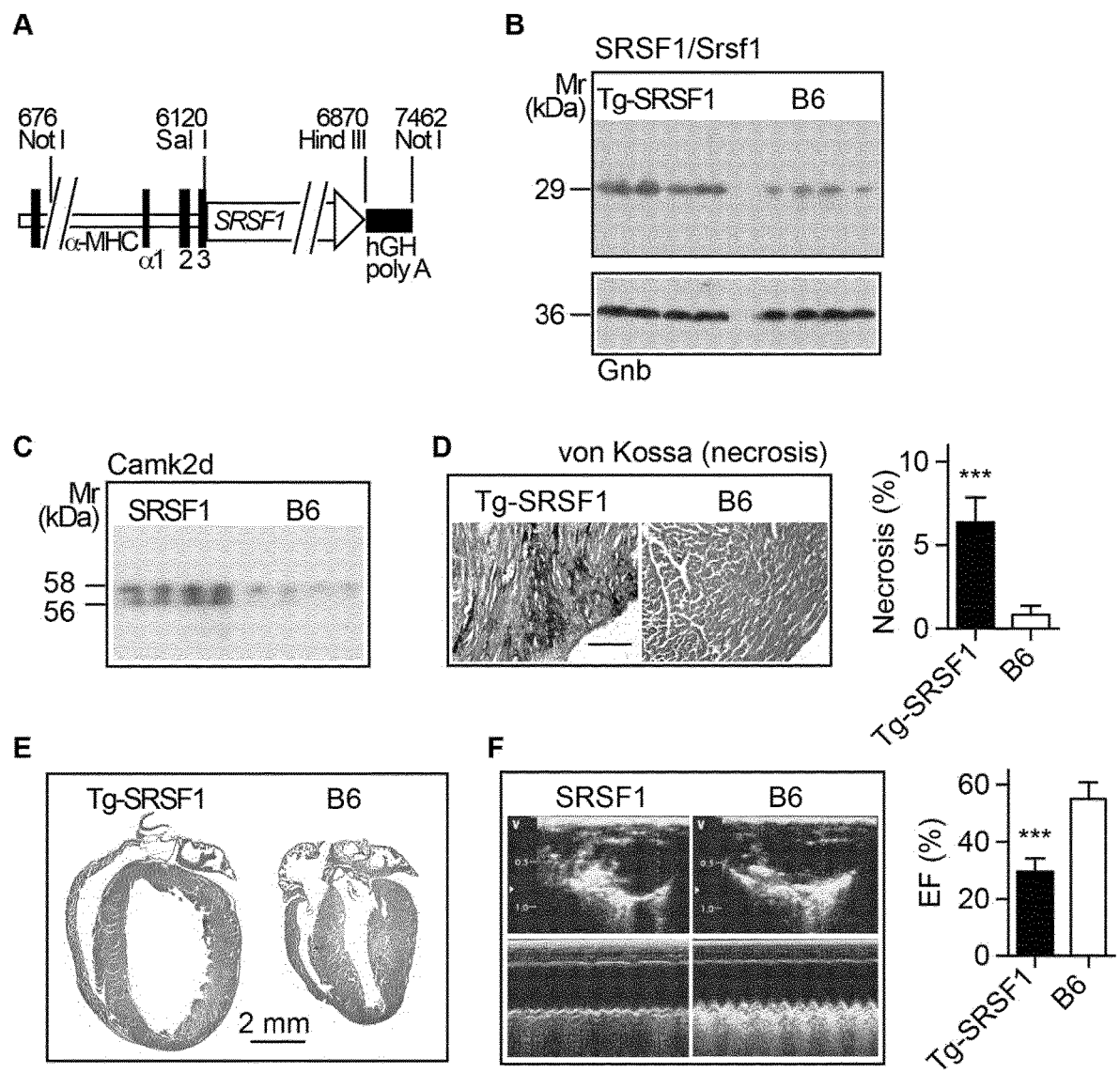
Figure 8:
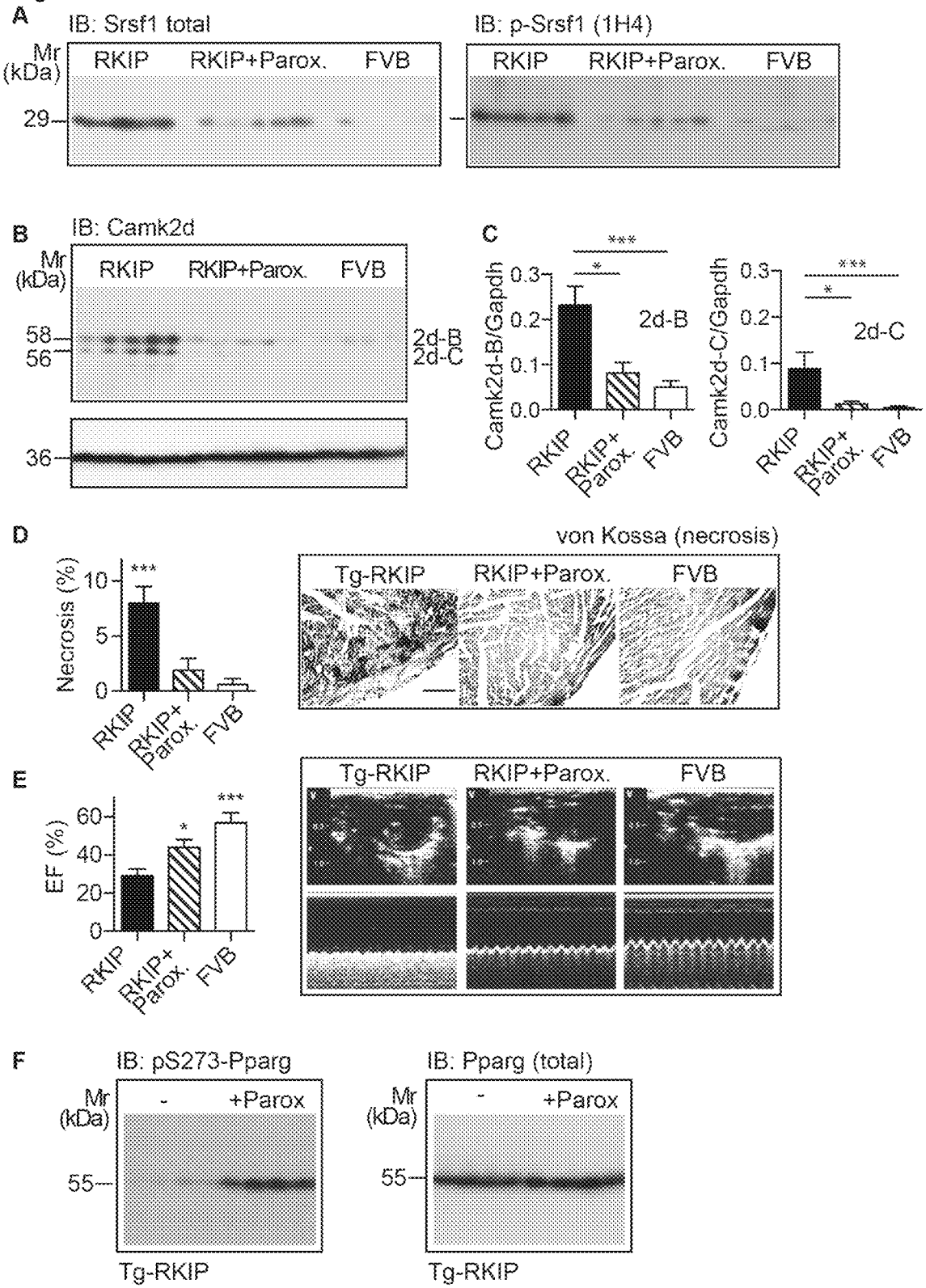
Figure 11:
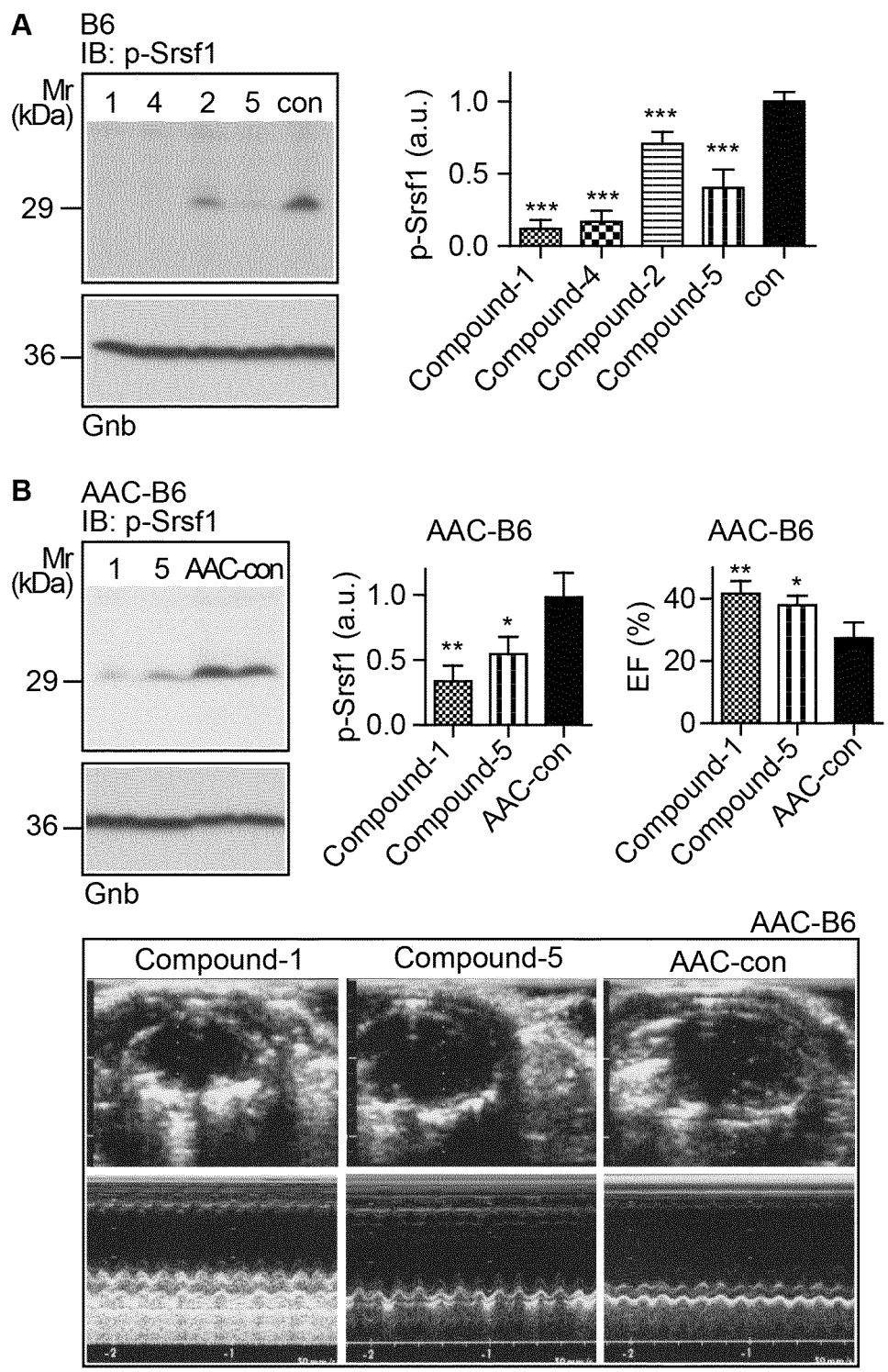
Figure 12:
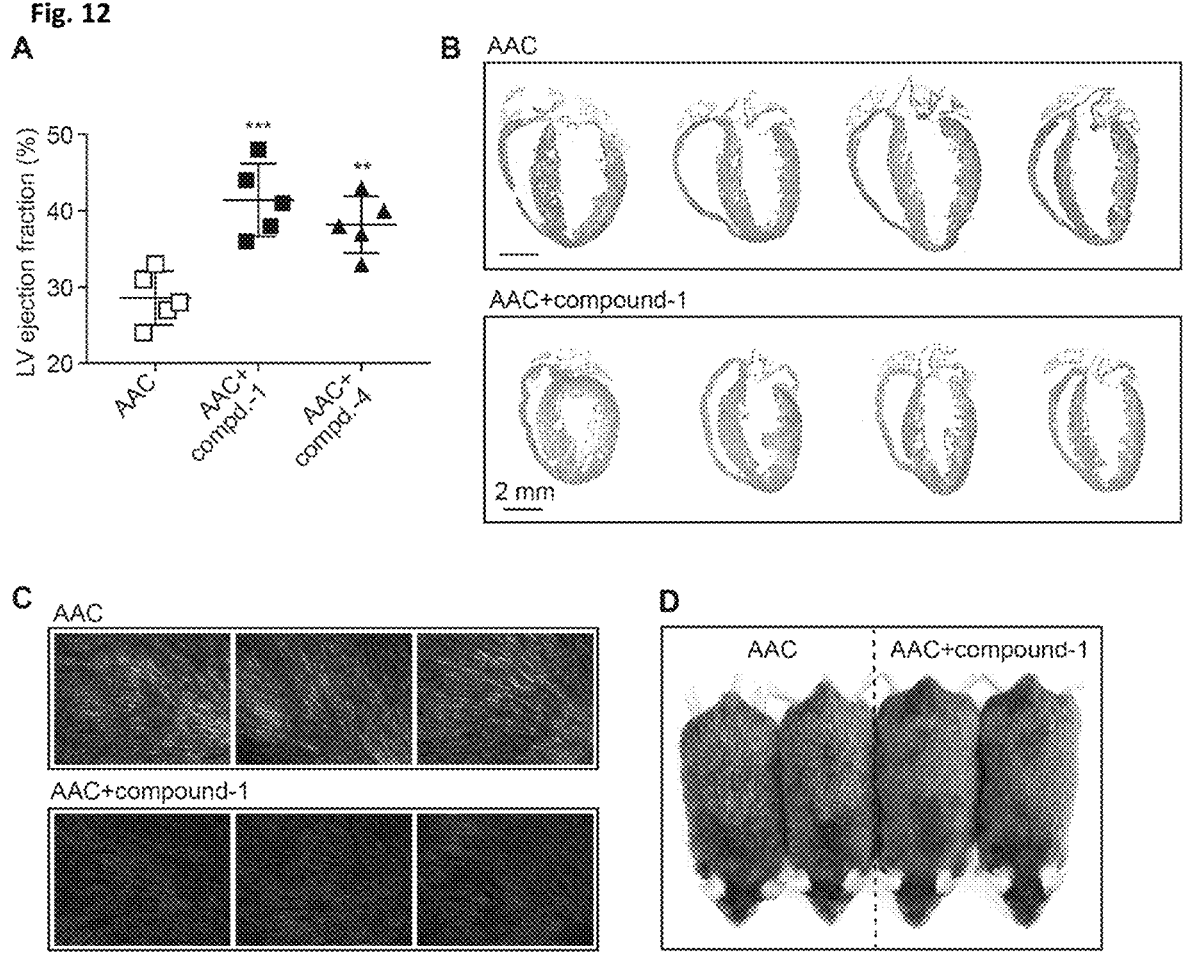

The above compounds target the GRK2-mediated activating phosphorylation of the non-receptor substrate SRSF1— a target which has not been considered before in cell protection, in particular cardio- and/or renal-protection and cardiotreatment. SRSF1 is a non-receptor GRK2 substrate, which promotes signs of heart failure, and GRK2-mediated phosphorylation of SRSF1 contributes to irreversible cardiomyocyte necrosis and cardiac dysfunction. The Examples 1 to 3 and FIGS. 1 to 3 further below with transgenic animal models document that GRK2-mediated SRSF1 phosphorylation promotes signs of heart failure, and cardiomyocyte necrosis, which is a major cause for irreversible heart damage. The compounds of the present invention interfere with this previously unrecognized major heart failure-promoting mechanism that is triggered by GRK2 (see Examples 9 to 12 and FIGS. 9 to 12 below). GRK2 is up-regulated in patients with cardiovascular disease and hypertension (see above). Transgenic mice with human GRK2 overexpression, which mimic the up-regulation of GRK2 found in the hearts of patients, developed enhanced SRSF1-mediated cardiomyocyte necrosis and cardiac dysfunction, e.g. due to enhanced splicing of CAMK2D isoforms B/C, which promote cardiomyocyte necrosis and heart failure (see Example 3 and FIG. 3 below). Notably, irreversible necrotic cardiomyocyte death is the main feature of myocardial infarction and ischemic heart disease, which are triggered by major cardiovascular risk factors, e.g. essential hypertension and other hypertensive disorders, atherosclerosis, chronic heart failure, hyperlipidemia, diabetes, stroke, depressive disorders, stress, aging. For example, inhibition of the GRK2-mediated heart failure-promoting SRSF1 phosphorylation by the compounds of the present invention exerts cardioprotection against chronic pressure overload-induced signs of heart failure in vivo (see Examples 11, 12 and FIG. 11, 12), e.g. by retarding the development of cardiomyocyte necrosis (see Examples 9 to 12 and FIGS. 9 to 12 below), cardiac dysfunction (see Examples 11,12 and FIG. 11,12) and cardiovascular disease-induced ageing (see Examples 12 and FIG. 12). It is noted that paroxetine also inhibits the GRK2-mediated SRSF1 phosphorylation in vitro and in vivo (see Example 8 and FIG. 8) but in a non-specific way with all its drawbacks mentioned above that render paroxetine not suitable for cardio-protective therapy in patients (Uguz et al., Gen Hosp Psychiatry 46-48, 37 (2015).

In a first aspect, the present invention is directed to the compounds disclosed above as such, i.e. in the context of substance claims. In a further aspect, the present invention relates to these compounds for use in medical treatment, preferably in cell-protective, in particular in cardio- and renal-protective treatment.

The term cardio-protective therapy, as used herein, means prevention or treatment of any disease or disorder that affects the heart, i.e. treatment that protects the heart from disease or treats an existing heart disease. Cardio-protective therapy includes, e.g. risk reduction of cardiovascular mortality and/or morbidity, prevention and treatment of irreversible necrotic cardiomyocyte death caused by, e.g. myocardial infarction, ischemic cardiovascular disease, angina pectoris, atherosclerosis, hypertensive disorders, chronic heart failure, chronic renal failure, cerebrovascular disease, decompensated heart failure, stress, aging and/or depression. Irreversible necrotic cardiomyocyte death can be or often is the major cause of cardiac remodeling culminating finally in cardiac dysfunction, cardiac hypertrophy with dilatation, thinning of the myocardium and end-stage heart failure.

In a preferred embodiment, the compound for use according to the present invention is a compound, wherein in Formula (I), a double bond is present between positions (3) and (4), or between positions (2) and (3) and between positions (4) and (5), or no double bond is present in the ring; and in Formula (II), no double bond is present in the ring or the ring is aromatic; and/or
a is 0 or 1; and/or
$R^1$ is selected from the group consisting of
  (i) hydrogen;
  (ii) linear or branched, substituted or non-substituted $(C_{1-5})$alkyl, more preferably methyl, ethyl and propyl, most preferably methyl;
  (iii) substituted or non-substituted cyclopropyl and phenyl, preferably substituted phenyl, more preferably phenyl that is mono-substituted in para position by a substituent selected from the group consisting of H, Cl, F, Br, methyl, —(CF$_3$) and cyclopropyl; and
  (iv) substituted or non-substituted, preferably non-substituted indazolyl, benzimidazolyl and benzodioxolyl connected via position (5) or (6), preferably via position (6) of the indazolyl and benzodioxolyl or position (5) of the benzimidazolyl.

In a further preferred embodiment, the compound for use according to the present invention is a compound, wherein $R^2$ is selected from the group consisting of
  (i) hydrogen or oxo;
  (ii) linear or branched, substituted or non-substituted $(C_{1-5})$alkyl, more preferably methyl, ethyl and propyl, most preferably methyl; and
  (iii) substituted or non-substituted indazolyl, benzimidazolyl and benzodioxolyl, preferably indazolyl, benzimidazolyl and benzodioxolyl connected via position (5) or (6) of the indazolyl, benzodioxolyl and benzimidazolyl; and/or
$R^3$ is selected from the group consisting of
  (i) hydrogen;
  (ii) linear or branched, substituted or non-substituted $(C_{1-5})$alkyl, more preferably methyl, ethyl and propyl, most preferably methyl;
  (iii)

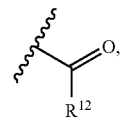

wherein $R^{12}$ is selected from the group consisting of
  (aa) N; and
  (bb) substituted or non-substituted cyclopropyl and phenyl, preferably phenyl that is mono-substituted in para position by cyclopropyl or —(CF$_3$) or di-substituted in meta position by cyclopropyl or —(CF$_3$) in each meta position; and
  (iv)

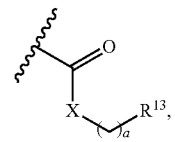

wherein X is N, a is 1 and $R^{13}$ is selected from the group consisting of substituted or non-substituted, preferably non-substituted indazolyl, benzimidazolyl and benzodioxolyl connected via position (6) or (5) of indazolyl, benzimidazolyl and benzodioxolyl, preferably via position (5) of the indazolyl and benzodioxolyl or position (6) of the benzimidazolyl;
and/or
$R^4$ is selected from the group consisting of
  (i) hydrogen and hydroxyl;
  (ii) linear or branched, substituted or non-substituted $(C_{1-5})$alkyl, more preferably methyl, ethyl and propyl, most preferably methyl;

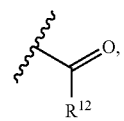

(iii) wherein $R^{12}$ is selected from the group consisting of
    (aa) N; and (bb) substituted or non-substituted cyclopropyl and phenyl, preferably phenyl that is mono-substituted in para or meta position by cyclopropyl or —($CF_3$), or di-substituted in meta position by cyclopropyl or —($CF_3$) in each meta position; and (iv)

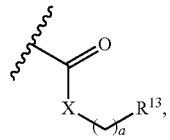

wherein X is N, a is 1 and $R^{13}$ is phenyl that is mono- or di-substituted in each meta position by cyclopropyl or —($CF_3$) or mono-substituted in para position by cyclopropyl or —($CF_3$);

wherein, if positions (2), (3) and/or (4) of the ring of Formula (I) are sp3-hybridized $R^2$ and $R^4$ and/or $R^3$ and $R^4$ are preferably in cis or trans configuration to each other, more preferably in trans configuration, preferably, $R^2$ is (R)- or (S)-, $R^3$ is (R)- or (S)- and/or $R^4$ is (R)- or (S)-configured, more preferably, $R^2$ is (R)-, $R^3$ is (R)- and/or $R^4$ is (R)-configured, or $R^2$ is (S)-, $R^3$ is (S)- and/or $R^4$ is (S)-configured; and/or $R^5$ is selected from the group consisting of
(i) hydrogen;
(ii) linear or branched, substituted or non-substituted ($C_{1-5}$)alkyl, more preferably methyl, ethyl and propyl, most preferably methyl;
(iii) substituted or non-substituted cyclopropyl and phenyl, preferably substituted phenyl, more preferably phenyl that is mono-substituted in para position by a substituent selected from the group consisting of H, Cl, F, Br, methyl, —($CF_3$) and cyclopropyl;
(iv) cyclopenta-2,4-dien-1-yl; and
(v) substituted or non-substituted, preferably non-substituted imidazolyl and pyrazolyl connected via the imidazolyl-/pyrazolyl-position-(1)-nitrogen to the ring of Formula (I);
wherein, if position (5) of the ring of Formula (I) is sp3-hybridized, $R^5$ is preferably (R)- or (S)-configured, more preferably (R)-configured; and/or $R^6$ and $R^{11}$ are independently selected from the group consisting of substituted or non-substituted, preferably non-substituted indazolyl, benzimidazolyl and benzodioxolyl connected via position (6) or (5), preferably via position (6) of the indazolyl and benzodioxolyl or position (5) of the benzimidazolyl;
wherein $R^6$ is not present if Y is S; and/or
wherein $R^{11}$ is absent if the ring of Formula (II) has a double bond between positions (4) and (5) or between positions (3) and (4) of the ring of Formula (II); and/or $R^7$ and $R^8$ are independently selected from the group consisting of
(i) hydrogen;
(ii) linear or branched, substituted or non-substituted ($C_{1-5}$)alkyl, more preferably methyl, ethyl and propyl, most preferably methyl; and (iii)

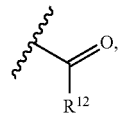

wherein $R^{12}$ is selected from the group consisting of
(aa) N; and
(bb) substituted or non-substituted cyclopropyl and phenyl, preferably phenyl that is mono-substituted in para position by cyclopropyl or —($CF_3$), or di-substituted in meta position by cyclopropyl or —($CF_3$) in each meta position;
wherein, for $R^8$, the group further comprises

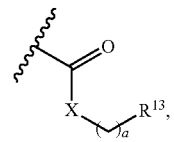

wherein X is N, a is 1 and $R^{13}$ is selected from the group consisting of substituted or non-substituted, preferably non-substituted indazolyl, benzimidazolyl and benzodioxolyl connected via position (6) or (5), preferably via position (5) of the indazolyl and benzodioxolyl or position (6) of the benzimidazolyl; and
wherein, if position (5) of the ring of Formula (II) is sp3-hybridized, $R^8$ is preferably (R)- or (S)-configured, more preferably (R)-configured; and/or $R^9$ is selected from the group consisting of
(i) hydrogen, methyl and cyclopropyl; and
(ii) substituted or non-substituted phenyl, preferably phenyl that is substituted in para position by a substituent selected from the group consisting of H, Cl, F, Br, methyl, —($CF_3$) and cyclopropyl; and
wherein, if position (3) of the ring of Formula (II) is sp3-hybridized, $R^9$ is preferably (R)- or (S)-configured, more preferably (S)-configured; and/or $R^{10}$ is absent or selected from the group consisting of
(i) hydrogen;
(ii) methyl; and
(iii) cyclopropyl and phenyl that is mono-substituted in para position by a substituent selected from the group consisting of H, Cl, F, Br, methyl, —($CF_3$) and cyclopropyl,
wherein $R^{10}$ is absent if X is C and/or if the ring of Formula (II) has a double bond between positions (1) and (2) or between positions (2) and (3) of the ring of Formula (II).

In a further preferred embodiment, the compound for use according to the present invention is a compound of Formula (I), wherein a double bond is located between positions (3) and (4) (Formula Ia)

Formula (Ia)

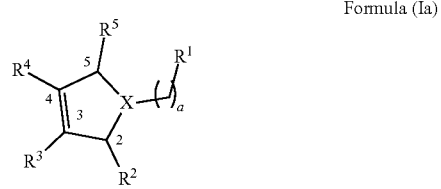

wherein X is N and a is 0, and wherein
$R^1$ is selected from the group consisting of indazolyl, benzimidazolyl and benzodioxolyl connected via position (6) or (5), preferably via position (6) of the indazolyl and benzodioxolyl or position (5) of the benzimidazolyl; and/or
$R^2$ is oxo; and/or
$R^3$ is selected from the group consisting of
  (i) hydrogen;
  (ii) methyl; and
  (iii)

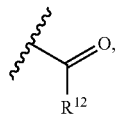

wherein $R^{12}$ is selected from the group consisting of
  (aa) N; and
  (bb) cyclopropyl and phenyl that is mono-substituted in para position by cyclopropyl or —($CF_3$), or di-substituted in meta position by cyclopropyl or —($CF_3$) in each meta position; and/or
$R^4$ is hydroxyl; and/or
$R^5$ is selected from the group consisting of
  (i) hydrogen;
  (ii) methyl;
  (iii) cyclopropyl and phenyl that is mono-substituted in para position by a substituent selected from the group consisting of H, Cl, F, Br, methyl, —($CF_3$) and cyclopropyl;
  (iv) cyclopenta-2,4-dien-1-yl; and
  (v) imidazolyl and pyrazolyl connected via the imidazolyl-/pyrazolyl-position-(1)-nitrogen to the ring of Formula (I);
  wherein $R^5$ is preferably (R)- or (S)-configured, more preferably (R)-configured.

In a further preferred embodiment, the compound for use according to the present invention is a compound of Formula (I), wherein two double bonds are located between positions (2) and (3) and between positions (4) and (5), respectively (Formula Ib)

Formula (Ib)

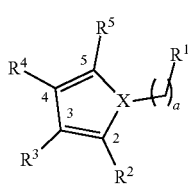

wherein X is N or C, preferably N, a is 0 or 1, preferably a is 0 if X is C, and wherein
$R^1$ is selected from the group consisting of indazolyl, benzimidazolyl and benzodioxolyl connected via position (5) or (6), preferably via position (6) of the indazolyl and benzodioxolyl or position (5) of the benzimidazolyl; and/or
$R^2$ is selected from the group consisting of
  (i) hydrogen; and
  (ii) methyl; and/or $R^3$ is selected from the group consisting of
  (i) hydrogen;
  (ii) methyl; and
  (iii)

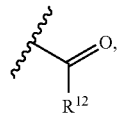

wherein $R^{12}$ is selected from the group consisting of
  (aa) N; and
  (bb) cyclopropyl and phenyl that is mono-substituted in para position by cyclopropyl or —($CF_3$), or di-substituted in meta position by cyclopropyl or —($CF_3$) in each meta position; and/or
$R^4$ is hydrogen; and/or
$R^5$ is selected from the group consisting of
  (i) hydrogen;
  (ii) methyl; and
  (iii) cyclopropyl and phenyl that is mono-substituted in para position by a substituent selected from the group consisting of H, Cl, F, Br, methyl, —($CF_3$) and cyclopropyl.

In a further preferred embodiment, the compound for use according to the present invention is a compound of Formula (I), wherein the bonds in the five-membered ring of Formula (I) are fully saturated (Formula Ic)

Formula (Ic)

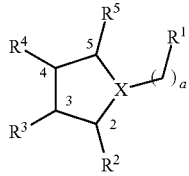

wherein X is N, a is 0 and wherein
$R^1$ is selected from the group consisting of
  (i) hydrogen;
  (ii) methyl; and
  (iii) cyclopropyl and phenyl that is mono-substituted in para position by a substituent selected from the group consisting of H, Cl, F, Br, methyl, —($CF_3$) and cyclopropyl; and/or
$R^2$ is selected from the group consisting of
  (i) hydrogen; and
  (ii) indazolyl, benzimidazolyl and benzodioxolyl, preferably indazolyl, benzimidazolyl and benzodioxolyl connected via position (5) or (6), more preferably via position (5) of the indazolyl and benzodioxolyl or position (6) of the benzimidazolyl if $R^3$ is not methyl, most preferably via position (6) of the indazolyl and benzodioxolyl or position (5) of the benzimidazolyl if $R^3$ is methyl; and/or
$R^3$ is selected from the group consisting of
  (i) hydrogen or methyl; and
  (ii)

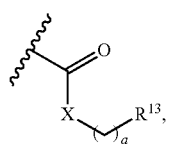

wherein X is N, a is 1 and R¹³ is selected from the group consisting of indazolyl, benzimidazolyl and benzodioxolyl connected via position (6) or (5) of indazolyl, benzimidazolyl and benzodioxolyl, preferably via position (5) of the indazolyl and benzodioxolyl or position (6) of the benzimidazolyl; and/or R⁴ is selected from the group consisting of
(i) hydrogen;
(ii) methyl;
(iii)

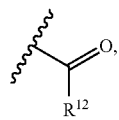

wherein R¹² is selected from the group consisting of
(aa) N; and
(bb) cyclopropyl and phenyl that is mono-substituted in para position by cyclopropyl or —(CF₃), or di-substituted in meta position by cyclopropyl or —(CF₃) in each meta position; and
(iv)

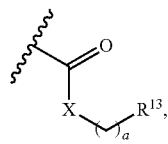

wherein X is N, a is 1 and R¹³ is phenyl that is mono-substituted in meta position by cyclopropyl or —(CF₃), or di-substituted in each meta position by cyclopropyl or —(CF₃), or mono-substituted in para position by cyclopropyl or —(CF₃); wherein, R² and R⁴ and/or R³ and R⁴ are preferably in a trans configuration to each other, preferably, R² is (S)-, R³ is (S)- and R⁴ is (R)-configured; and/or R⁵ is hydrogen.

In a further preferred embodiment, the compound for use according to the present invention is a compound of Formula (II), wherein the bonds within the ring of Formula (II) are fully saturated (Formula IIa)

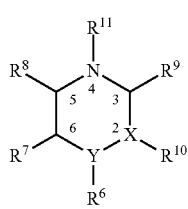

Formula (IIa)

wherein X is C, Y is S and wherein
R⁶ is not present; and/or
R⁷ is selected from the group consisting of
(i) hydrogen;
(ii) methyl; and (iii)

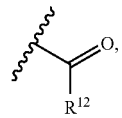

wherein R¹² is selected from the group consisting of
(aa) N; and
(bb) cyclopropyl or phenyl mono-substituted in para position by cyclopropyl or —(CF₃) or di-substituted in meta position by cyclopropyl or —(CF₃) in each meta position; and/or R⁸ is selected from the group consisting of
(i) hydrogen and methyl; and
(ii)

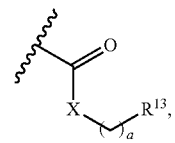

wherein X is N, a is 1 and R¹³ is selected from the group consisting of indazolyl, benzimidazolyl and benzodioxolyl connected via position (6) or (5), preferably via position (5) of the indazolyl and benzodioxolyl or position (6) of the benzimidazolyl;
wherein R⁸ is preferably (R)- or (S)-configured, more preferably (R)-configured; and/or R⁹ is selected from the group consisting of
(i) hydrogen, methyl and cyclopropyl; and
(ii) phenyl that is mono-substituted in para position by a substituent selected from the group consisting of H, Cl, F, Br, methyl, —(CF₃) and cyclopropyl;
wherein R⁹ is preferably (R)- or (S)-configured, more preferably (S)-configured; and/or R¹⁰ is hydrogen; and/or
R¹¹ is hydrogen or selected from the group consisting of indazolyl, benzimidazolyl and benzodioxolyl connected via position (6) or (5), preferably via position (6) of the indazolyl and benzodioxolyl or position (5) of the benzimidazolyl.

In a further preferred embodiment, the compound for use according to the present invention is a compound of Formula (II), wherein the ring of Formula (II) is aromatic (Formula IIb)

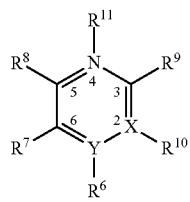

Formula (IIb)

wherein X is N, Y is C and wherein
R⁶ is selected from the group consisting of indazolyl, benzimidazolyl and benzodioxolyl connected via position (6) or (5), preferably via position (6) of the indazolyl and benzodioxolyl or position (5) of the benzimidazolyl; and/or $R^7$ and $R^8$ are independently selected from the group consisting of
(i) hydrogen;
(ii) methyl; and
(iii)

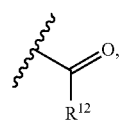

wherein $R^{12}$ is selected from the group consisting of
(aa) N; and
(bb) cyclopropyl and phenyl that is mono-substituted in para position by cyclopropyl or —($CF_3$), or di-substituted in meta position by cyclopropyl or —($CF_3$) in each meta position; and/or $R^9$ is hydrogen; and/or $R^{10}$ and/or $R^{11}$ are absent.

In a further preferred embodiment, the compound for use according to the present invention is a compound of Formula (II), wherein two double bonds are located between positions (1) and (6) and between positions (4) and (5), respectively (Formula IIc)

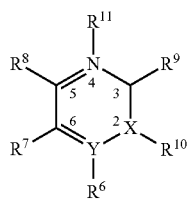

Formula (IIc)

wherein X is N, Y is C and wherein $R^6$ is selected from the group consisting of indazolyl, benzimidazolyl and benzodioxolyl connected via position (6) or (5), preferably via position (6) of the indazolyl and benzodioxolyl or position (5) of the benzimidazolyl; and/or $R^7$ and $R^8$ are independently selected from the group consisting of hydrogen and methyl; and/or $R^9$ is hydrogen; and/or $R^{10}$ is selected from the group consisting of
(i) hydrogen;
(ii) methyl; and
(iii) cyclopropyl and phenyl that is mono-substituted in para position by a substituent selected from the group consisting of H, Cl, F, Br, methyl, —($CF_3$) and cyclopropyl; and/or $R^{11}$ is absent.

In a further preferred embodiment, the compound for use according to the present invention is a compound, wherein $R^1$ is selected from the group consisting of hydrogen, methyl,

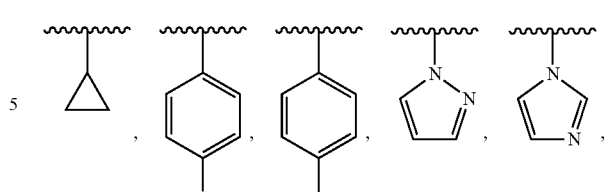

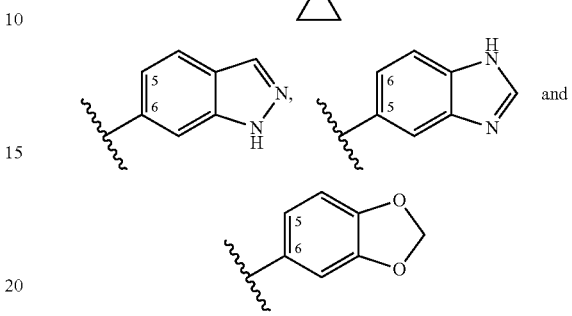

Z = H, Me, ($CF_3$), F, Cl, Br and/or $R^2$ is selected from the group consisting of hydrogen, oxo, methyl,

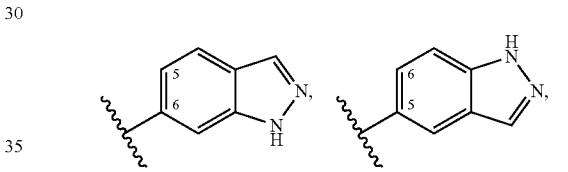

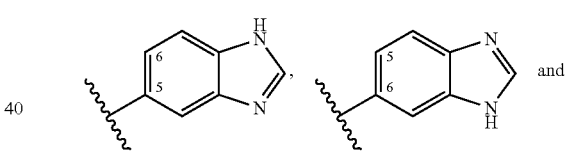

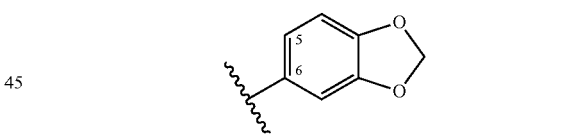

and/or $R^3$ is selected from the group consisting of hydrogen, methyl,

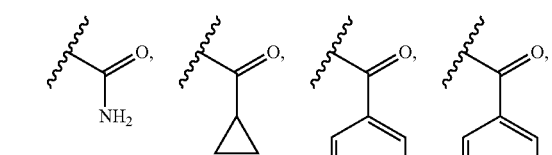

-continued

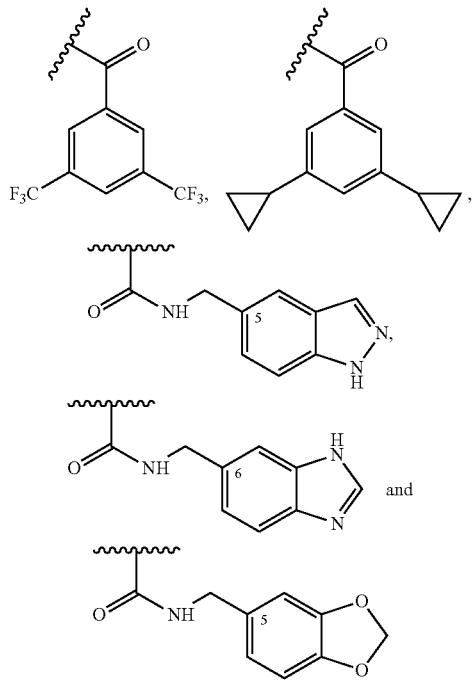

and/or

R⁴ is selected from the group consisting of hydrogen, hydroxyl, methyl,

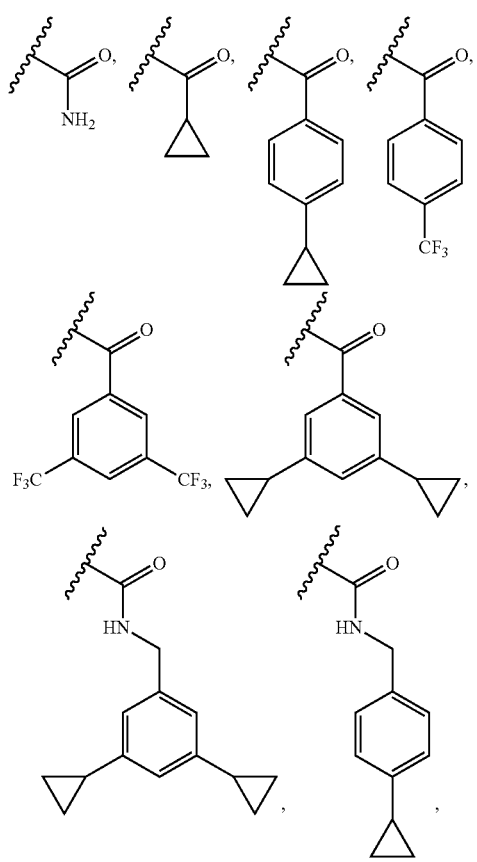

-continued

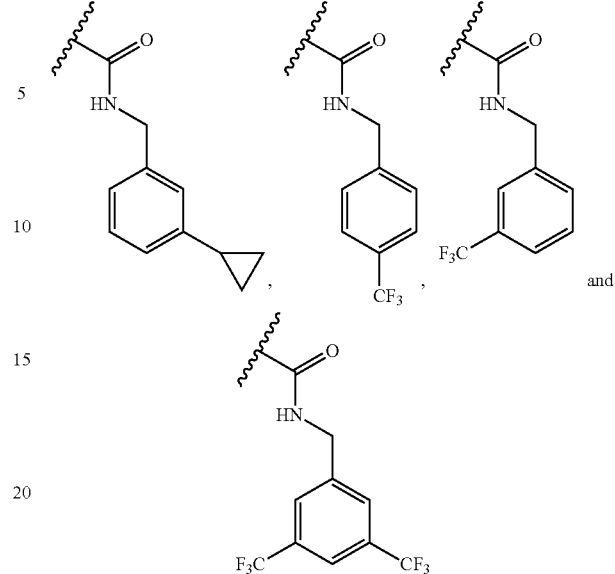

wherein, $R^4$ and/or $R^3$ and $R^4$ are preferably in cis or trans configuration to each other, more preferably in trans configuration, preferably, $R^2$ is (R)- or (S)-, $R^3$ is (R)- or (S)- and/or $R^4$ is (R)- or (S)-configured, more preferably, $R^2$ is (R)-, $R^3$ is (R)- and/or $R^4$ is (R)-configured, or $R^2$ is or (S)-, $R^3$ is (S)- and/or $R^4$ is (S)-configured, and/or $R^5$ and $R^9$ are selected from the group consisting of hydrogen, methyl, cyclopenta-2,4-dien-1-yl,

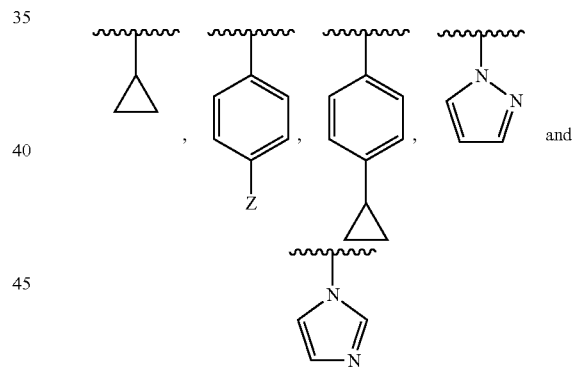

Z = H, Me, (CF₃), F, Cl, Br wherein $R^9$ is preferably not cyclopenta-2,4-dien-1-yl, wherein, if position (5) of the ring of Formula (I) is sp³-hybridized, $R^5$ is preferably (R)- or (S)-configured, more preferably (R)-configured, and wherein $R^9$ is preferably (R)- or (S)-configured, more preferably (R)-configured, and/or $R^6$ is not present if Y is S, and if Y is C, $R^6$ is selected from the group consisting of

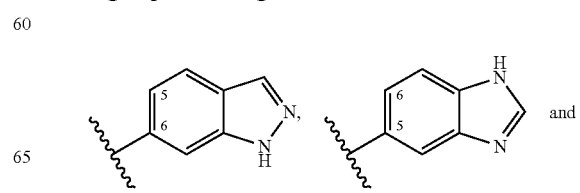

-continued

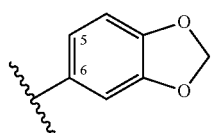

and/or
R⁷ and R⁸ are selected from the group consisting of hydrogen, methyl,

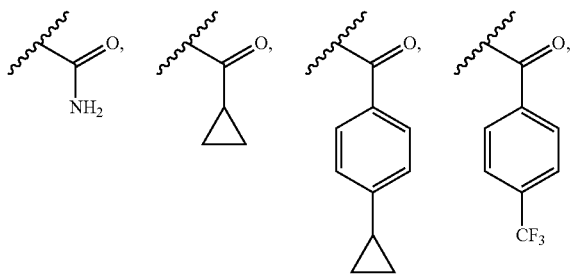

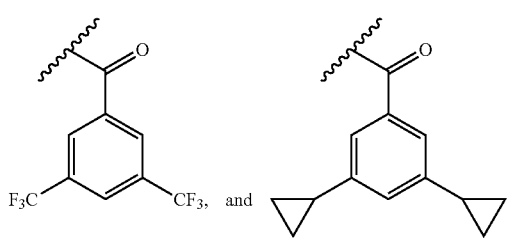

wherein R⁸ is additionally selected from the group consisting of

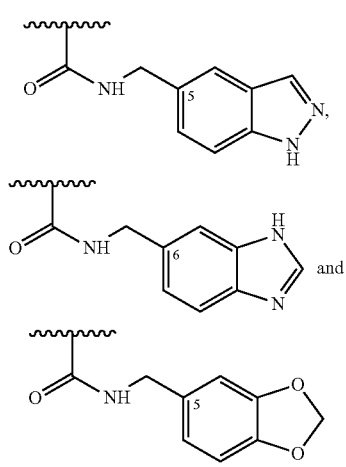

and wherein R⁸ is preferably (R)- or (S)-configured, more preferably (R)-configured; and/or
R¹⁰ is absent or selected from the group consisting of hydrogen, methyl,

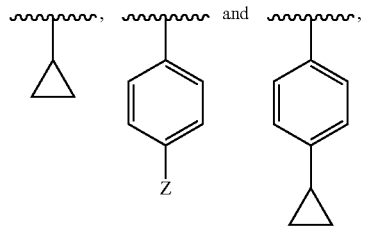

Z = H, Me, (CF₃), F, Cl, Br wherein R¹⁰ is absent if X is C and/or if the ring of Formula (II) has a double bond between positions (1) and (2) or between positions (2) and (3) of the ring of Formula (II), and/or
R¹¹ is absent or selected from the group consisting of hydrogen,

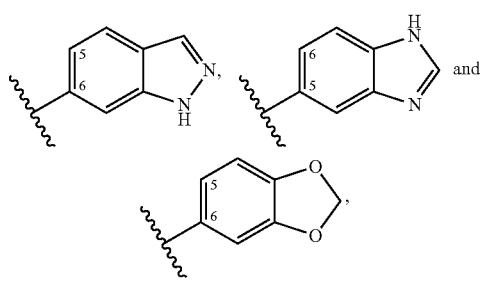

wherein R¹¹ is absent if the ring of Formula (II) has a double bond between positions (4) and (5) or between positions (3) and (4) of the ring of Formula (II).

In a further preferred embodiment, the compound for use according to the present invention is a compound selected from the group consisting of:
(i) a first residue selected from the group consisting of
1-(1,3-benzodioxol-5-yl)-3-hydroxy-5-oxo-2-methyl-2H-pyrrol-4-yl,
1-(1,3-benzodioxol-5-yl)-2-cyclopropyl-3-hydroxy-5-oxo-2H-pyrrol-4-yl,
1-(1,3-benzodioxol-5-yl)-3-hydroxy-5-oxo-2H-pyrrol-4-yl,
1-(1,3-benzodioxol-5-yl)-2-(cyclopenta-2,4-dien-1-yl)-5-oxo-3-hydroxy-2H-pyrrol-4-yl,
1-(1,3-benzodioxol-5-yl)-3-hydroxy-5-oxo-2-(pyrazol-1-yl)-2H-pyrrol-4-yl,
1-(1,3-benzodioxol-5-yl)-3-hydroxy-5-oxo-2-(imidazol-1-yl)-2H-pyrrol-4-yl,
1-(1,3-benzodioxol-5-yl)-3-hydroxy-5-oxo-2-phenyl-2H-pyrrol-4-yl,
1-(1,3-benzodioxol-5-yl)-3-hydroxy-5-oxo-2-(p-tolyl)-2H-pyrrol-4-yl,
1-(1,3-benzodioxol-5-yl)-2-(4-chlorophenyl)-3-hydroxy-5-oxo-2H-pyrrol-4-yl,
1-(1,3-benzodioxol-5-yl)-2-(4-fluorophenyl)-3-hydroxy-5-oxo-2H-pyrrol-4-yl,
1-(1,3-benzodioxol-5-yl)-2-(4-bromophenyl)-3-hydroxy-5-oxo-2H-pyrrol-4-yl,
1-(1,3-benzodioxol-5-yl)-2-(4-cyclopropylphenyl)-3-hydroxy-5-oxo-2H-pyrrol-4-yl,
1-(1,3-benzodioxol-5-yl)-3-hydroxy-5-oxo-2-[4-(trifluoromethyl)phenyl]-2H-pyrrol-4-yl,
3-hydroxy-1-(1H-indazol-6-yl)-5-oxo-2-[4-(trifluoromethyl)phenyl]-2H-pyrrol-4-yl, 3-hydroxy-1-(1H-indazol-6-yl)-5-oxo-2-phenyl-2H-pyrrol-4-yl,
3-hydroxy-1-(1H-indazol-6-yl)-5-oxo-2-(p-tolyl)-2H-pyrrol-4-yl,
2-(4-chlorophenyl)-3-hydroxy-1-(1H-indazol-6-yl)-5-oxo-2H-pyrrol-4-yl,
2-(4-fluorophenyl)-3-hydroxy-1-(1H-indazol-6-yl)-5-oxo-2H-pyrrol-4-yl,
2-(4-bromophenyl)-3-hydroxy-1-(1H-indazol-6-yl)-5-oxo-2H-pyrrol-4-yl,
2-(4-cyclopropylphenyl)-3-hydroxy-1-(1H-indazol-6-yl)-5-oxo-2H-pyrrol-4-yl,
2-cyclopropyl-3-hydroxy-1-(1H-indazol-6-yl)-5-oxo-2H-pyrrol-4-yl,
3-hydroxy-1-(1H-indazol-6-yl)-5-oxo-2-methyl-2H-pyrrol-4-yl,
3-hydroxy-1-(1H-indazol-6-yl)-5-oxo-2H-pyrrol-4-yl,
3-hydroxy-1-(1H-indazol-6-yl)-5-oxo-2-(pyrazol-1-yl)-2H-pyrrol-4-yl,
2-(cyclopenta-2,4-dien-1-yl)-3-hydroxy-1-(1H-indazol-6-yl)-5-oxo-2H-pyrrol-4-yl,
3-hydroxy-2-(imidazol-1-yl)-1-(1H-indazol-6-yl)-5-oxo-2H-pyrrol-4-yl,
1-(1H-benzimidazol-5-yl)-3-hydroxy-5-oxo-2-dimethyl-2H-pyrrol-4-yl,
1-(1H-benzimidazol-5-yl)-2-cyclopropyl-3-hydroxy-5-oxo-2H-pyrrol-4-yl,
1-(1H-benzimidazol-5-yl)-3-hydroxy-5-oxo-2-(pyrazol-1-yl)-2H-pyrrol-4-yl,
1-(1H-benzimidazol-5-yl)-3-hydroxy-5-oxo-2H-pyrrol-4-yl,
1-(1H-benzimidazol-5-yl)-3-hydroxy-5-oxo-2-(imidazol-1-yl)-2H-pyrrol-4-yl,
1-(1H-benzimidazol-5-yl)-2-(cyclopenta-2,4-dien-1-yl)-3-hydroxy-5-oxo-2H-pyrrol-4-yl,
1-(1H-benzimidazol-5-yl)-2-(4-fluorophenyl)-3-hydroxy-5-oxo-2H-pyrrol-4-yl,
1-(1H-benzimidazol-5-yl)-3-hydroxy-5-oxo-2-[4-(trifluoromethyl)phenyl]-2H-pyrrol-4-yl,
1-(1H-benzimidazol-5-yl)-3-hydroxy-5-oxo-2-phenyl-2H-pyrrol-4-yl,
1-(1H-benzimidazol-5-yl)-3-hydroxy-5-oxo-2-(p-tolyl)-2H-pyrrol-4-yl,
1-(1H-benzimidazol-5-yl)-2-(4-chlorophenyl)-3-hydroxy-5-oxo-2H-pyrrol-4-yl,
1-(1H-benzimidazol-5-yl)-2-(4-bromophenyl)-3-hydroxy-5-oxo-2H-pyrrol-4-yl,
1-(1H-benzimidazol-5-yl)-2-(4-cyclopropylphenyl)-3-hydroxy-5-oxo-2H-pyrrol-4-yl,
wherein the numbering of the 2H-pyrrole ring is as follows:

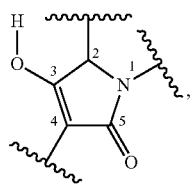 [SMILES: *C1=C(O)C(*)N(*)C1=O]

1-(1,3-benzodioxol-5-ylmethyl)-2-methyl-5-(p-tolyl)pyrrol-3-yl,
1-(1,3-benzodioxol-5-ylmethyl)-5-(4-chlorophenyl)-2-methyl-pyrrol-3-yl,
1-(1,3-benzodioxol-5-ylmethyl)-5-(4-fluorophenyl)-2-methyl-pyrrol-3-yl,
1-(1,3-benzodioxol-5-ylmethyl)-2-methyl-5-[4-(trifluoromethyl)phenyl]pyrrol-3-yl,
1-(1,3-benzodioxol-5-ylmethyl)-5-(4-bromophenyl)-2-methyl-pyrrol-3-yl,
1-(1,3-benzodioxol-5-ylmethyl)-5-(4-cyclopropylphenyl)-2-methyl-pyrrol-3-yl,
1-(1,3-benzodioxol-5-ylmethyl)-2-methyl-5-phenyl-pyrrol-3-yl,
1-(1,3-benzodioxol-5-ylmethyl)-5-phenyl-pyrrol-3-yl,
1-(1,3-benzodioxol-5-ylmethyl)-5-(p-tolyl)pyrrol-3-yl,
1-(1,3-benzodioxol-5-ylmethyl)-5-(4-fluorophenyl)pyrrol-3-yl,
1-(1,3-benzodioxol-5-ylmethyl)-5-[4-(trifluoromethyl)phenyl]pyrrol-3-yl,
1-(1,3-benzodioxol-5-ylmethyl)-5-(4-chlorophenyl)pyrrol-3-yl,
1-(1,3-benzodioxol-5-ylmethyl)-5-(4-bromophenyl)pyrrol-3-yl,
1-(1,3-benzodioxol-5-ylmethyl)-5-(4-cyclopropylphenyl)pyrrol-3-yl,
1-(1,3-benzodioxol-5-ylmethyl)-2,5-dimethyl-pyrrol-3-yl,
1-(1,3-benzodioxol-5-ylmethyl)-2-methyl-pyrrol-3-yl,
1-(1,3-benzodioxol-5-ylmethyl)-5-cyclopropyl-2-methyl-pyrrol-3-yl,
1-(1,3-benzodioxol-5-ylmethyl)pyrrol-3-yl,
1-(1,3-benzodioxol-5-ylmethyl)-5-methyl-pyrrol-3-yl,
1-(1,3-benzodioxol-5-ylmethyl)-5-cyclopropyl-pyrrol-3-yl,
1-(1H-indazol-6-ylmethyl)-2-methyl-5-phenyl-pyrrol-3-yl,
1-(1H-indazol-6-ylmethyl)-2-methyl-5-(p-tolyl)pyrrol-3-yl,
5-(4-chlorophenyl)-1-(1H-indazol-6-ylmethyl)-2-methyl-pyrrol-3-yl,
5-(4-fluorophenyl)-1-(1H-indazol-6-ylmethyl)-2-methyl-pyrrol-3-yl,
1-(1H-indazol-6-ylmethyl)-2-methyl-5-[4-(trifluoromethyl)phenyl]pyrrol-3-yl,
5-(4-bromophenyl)-1-(1H-indazol-6-ylmethyl)-2-methyl-pyrrol-3-yl,
5-(4-cyclopropylphenyl)-1-(1H-indazol-6-ylmethyl)-2-methyl-pyrrol-3-yl,
1-(1H-indazol-6-ylmethyl)-5-phenyl-pyrrol-3-yl,
1-(1H-indazol-6-ylmethyl)-5-(p-tolyl)pyrrol-3-yl,
5-(4-fluorophenyl)-1-(1H-indazol-6-ylmethyl)pyrrol-3-yl,
1-(1H-indazol-6-ylmethyl)-5-[4-(trifluoromethyl)phenyl]pyrrol-3-yl,
5-(4-chlorophenyl)-1-(1H-indazol-6-ylmethyl)pyrrol-3-yl,
5-(4-bromophenyl)-1-(1H-indazol-6-ylmethyl)pyrrol-3-yl,
5-(4-cyclopropylphenyl)-1-(1H-indazol-6-ylmethyl)pyrrol-3-yl,
5-cyclopropyl-1-(1H-indazol-6-ylmethyl)-2-methyl-pyrrol-3-yl,
1-(1H-indazol-6-ylmethyl)-2-methyl-pyrrol-3-yl,
1-(1H-indazol-6-ylmethyl)-2,5-dimethyl-pyrrol-3-yl,
1-(1H-indazol-6-ylmethyl)pyrrol-3-yl,
5-cyclopropyl-1-(1H-indazol-6-ylmethyl)pyrrol-3-yl,
1-(1H-indazol-6-ylmethyl)-5-methyl-pyrrol-3-yl,
1-(1H-benzimidazol-5-ylmethyl)-2-methyl-5-phenyl-pyrrol-3-yl,
1-(1H-benzimidazol-5-ylmethyl)-2-methyl-5-(p-tolyl)pyrrol-3-yl,
1-(1H-benzimidazol-5-ylmethyl)-2-methyl-5-(p-tolyl)pyrrol-3-yl,
1-(1H-benzimidazol-5-ylmethyl)-5-(4-fluorophenyl)-2-methyl-pyrrol-3-yl,
1-(1H-benzimidazol-5-ylmethyl)-5-(4-cyclopropylphenyl)-2-methyl-pyrrol-3-yl,
1-(1H-benzimidazol-5-ylmethyl)-5-(4-bromophenyl)-2-methyl-pyrrol-3-yl, 1-(1H-benzimidazol-5-ylmethyl)-2-methyl-5-[4-(trifluoromethyl)phenyl]pyrrol-3-yl,
1-(1H-benzimidazol-5-ylmethyl)-5-phenyl-pyrrol-3-yl,
1-(1H-benzimidazol-5-ylmethyl)-5-(p-tolyl)pyrrol-3-yl,
1-(1H-benzimidazol-5-ylmethyl)-5-[4-(trifluoromethyl)phenyl]pyrrol-3-yl,
1-(1H-benzimidazol-5-ylmethyl)-5-(4-chlorophenyl)pyrrol-3-yl,
1-(1H-benzimidazol-5-ylmethyl)-5-(4-fluorophenyl)pyrrol-3-yl,
1-(1H-benzimidazol-5-ylmethyl)-5-(4-bromophenyl)pyrrol-3-yl,
1-(1H-benzimidazol-5-ylmethyl)-5-(4-cyclopropylphenyl)pyrrol-3-yl,
1-(1H-benzimidazol-5-ylmethyl)-2,5-dimethyl-pyrrol-3-yl,
1-(1H-benzimidazol-5-ylmethyl)-2-methyl-pyrrol-3-yl,
1-(1H-benzimidazol-5-ylmethyl)-5-cyclopropyl-2-methyl-pyrrol-3-yl,
1-(1H-benzimidazol-5-ylmethyl)-5-methyl-pyrrol-3-yl,
1-(1H-benzimidazol-5-ylmethyl)pyrrol-3-yl,
1-(1H-benzimidazol-5-ylmethyl)-5-cyclopropyl-pyrrol-3-yl,
1-(1,3-benzodioxol-5-yl)-5-(p-tolyl)pyrrol-3-yl,
1-(1,3-benzodioxol-5-yl)-5-phenyl-pyrrol-3-yl,
1-(1,3-benzodioxol-5-yl)-5-(4-fluorophenyl)pyrrol-3-yl,
1-(1,3-benzodioxol-5-yl)-5-[4-(trifluoromethyl)phenyl]pyrrol-3-yl,
1-(1,3-benzodioxol-5-yl)-5-(4-bromophenyl)pyrrol-3-yl,
1-(1,3-benzodioxol-5-yl)-5-(4-chlorophenyl)pyrrol-3-yl,
1-(1,3-benzodioxol-5-yl)-5-(4-cyclopropylphenyl)pyrrol-3-yl,
1-(1,3-benzodioxol-5-yl)-2-methyl-5-(p-tolyl)pyrrol-3-yl,
1-(1,3-benzodioxol-5-yl)-2-methyl-5-phenyl-pyrrol-3-yl,
1-(1,3-benzodioxol-5-yl)-5-(4-fluorophenyl)-2-methyl-pyrrol-3-yl,
1-(1,3-benzodioxol-5-yl)-2-methyl-5-[4-(trifluoromethyl)phenyl]pyrrol-3-yl,
1-(1,3-benzodioxol-5-yl)-5-(4-chlorophenyl)-2-methyl-pyrrol-3-yl,
1-(1,3-benzodioxol-5-yl)-5-(4-bromophenyl)-2-methyl-pyrrol-3-yl,
1-(1,3-benzodioxol-5-yl)-5-(4-cyclopropylphenyl)-2-methyl-pyrrol-3-yl,
1-(1,3-benzodioxol-5-yl)-2,5-dimethyl-pyrrol-3-yl,
1-(1,3-benzodioxol-5-yl)-2-methyl-pyrrol-3-yl,
1-(1,3-benzodioxol-5-yl)-5-cyclopropyl-2-methyl-pyrrol-3-yl,
1-(1,3-benzodioxol-5-yl)-5-methyl-pyrrol-3-yl,
1-(1,3-benzodioxol-5-yl)pyrrol-3-yl,
1-(1,3-benzodioxol-5-yl)-5-cyclopropyl-pyrrol-3-yl,
1-(1H-indazol-6-yl)-5-(p-tolyl)pyrrol-3-yl,
5-(4-chlorophenyl)-1-(1H-indazol-6-yl)pyrrol-3-yl,
5-(4-bromophenyl)-1-(1H-indazol-6-yl)pyrrol-3-yl,
5-(4-fluorophenyl)-1-(1H-indazol-6-yl)pyrrol-3-yl,
1-(1H-indazol-6-yl)-5-phenyl-pyrrol-3-yl,
5-(4-cyclopropylphenyl)-1-(1H-indazol-6-yl)pyrrol-3-yl,
1-(1H-indazol-6-yl)-5-[4-(trifluoromethyl)phenyl]pyrrol-3-yl,
1-(1H-indazol-6-yl)-2-methyl-5-(p-tolyl)pyrrol-3-yl,
5-(4-chlorophenyl)-1-(1H-indazol-6-yl)-2-methyl-pyrrol-3-yl,
5-(4-bromophenyl)-1-(1H-indazol-6-yl)-2-methyl-pyrrol-3-yl,
5-(4-fluorophenyl)-1-(1H-indazol-6-yl)-2-methyl-pyrrol-3-yl,
1-(1H-indazol-6-yl)-2-methyl-5-phenyl-pyrrol-3-yl,
5-(4-cyclopropylphenyl)-1-(1H-indazol-6-yl)-2-methyl-pyrrol-3-yl,
1-(1H-indazol-6-yl)-2-methyl-5-[4-(trifluoromethyl)phenyl]pyrrol-3-yl,
1-(1H-indazol-6-yl)-2,5-dimethyl-pyrrol-3-yl,
1-(1H-indazol-6-yl)-2-methyl-pyrrol-3-yl,
5-cyclopropyl-1-(1H-indazol-6-yl)-2-methyl-pyrrol-3-yl,
1-(1H-indazol-6-yl)-5-methyl-pyrrol-3-yl,
1-(1H-indazol-6-yl)pyrrol-3-yl,
5-cyclopropyl-1-(1H-indazol-6-yl)pyrrol-3-yl,
1-(1H-benzimidazol-5-yl)-5-(p-tolyl)pyrrol-3-yl,
1-(1H-benzimidazol-5-yl)-5-(4-chlorophenyl)pyrrol-3-yl,
1-(1H-benzimidazol-5-yl)-5-(4-bromophenyl)pyrrol-3-yl,
1-(1H-benzimidazol-5-yl)-5-(4-fluorophenyl)pyrrol-3-yl,
1-(1H-benzimidazol-5-yl)-5-phenyl-pyrrol-3-yl,
1-(1H-benzimidazol-5-yl)-5-(4-cyclopropylphenyl)pyrrol-3-yl,
1-(1H-benzimidazol-5-yl)-5-[4-(trifluoromethyl)phenyl]pyrrol-3-yl,
1-(1H-benzimidazol-5-yl)-2-methyl-5-(p-tolyl)pyrrol-3-yl,
1-(1H-benzimidazol-5-yl)-5-(4-chlorophenyl)-2-methyl-pyrrol-3-yl,
1-(1H-benzimidazol-5-yl)-5-(4-bromophenyl)-2-methyl-pyrrol-3-yl,
1-(1H-benzimidazol-5-yl)-5-(4-fluorophenyl)-2-methyl-pyrrol-3-yl,
1-(1H-benzimidazol-5-yl)-2-methyl-5-phenyl-pyrrol-3-yl,
1-(1H-benzimidazol-5-yl)-5-(4-cyclopropylphenyl)-2-methyl-pyrrol-3-yl,
1-(1H-benzimidazol-5-yl)-2-methyl-5-[4-(trifluoromethyl)phenyl]pyrrol-3-yl,
1-(1H-benzimidazol-5-yl)-2,5-dimethyl-pyrrol-3-yl,
1-(1H-benzimidazol-5-yl)-2-methyl-pyrrol-3-yl,
1-(1H-benzimidazol-5-yl)-5-cyclopropyl-2-methyl-pyrrol-3-yl,
1-(1H-benzimidazol-5-yl)-5-methyl-pyrrol-3-yl,
1-(1H-benzimidazol-5-yl)pyrrol-3-yl,
1-(1H-benzimidazol-5-yl)-5-cyclopropyl-pyrrol-3-yl,
wherein the numbering of the pyrrole ring is as follows:

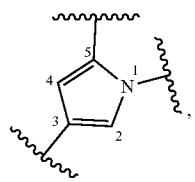

(3R)-3-(1,3-benzodioxol-5-ylmethylcarbamoyl)-5-phenyl-thiomorpholin-2-yl,
(3R)-3-(1,3-benzodioxol-5-ylmethylcarbamoyl)-5-(p-tolyl)thiomorpholin-2-yl,
(3R)-3-(1,3-benzodioxol-5-ylmethylcarbamoyl)-5-(4-fluorophenyl)thiomorpholin-2-yl,
(3R)-3-(1,3-benzodioxol-5-ylmethylcarbamoyl)-5-(4-bromophenyl)thiomorpholin-2-yl,
(3R)-3-(1,3-benzodioxol-5-ylmethylcarbamoyl)-5-(4-chlorophenyl)thiomorpholin-2-yl,
(3R)-3-(1,3-benzodioxol-5-ylmethylcarbamoyl)-5-(4-cyclopropylphenyl)thiomorpholin-2-yl,
(3R)-3-(1,3-benzodioxol-5-ylmethylcarbamoyl)-5-[4-(trifluoromethyl)phenyl]thio-morpholin-2-yl,
(3R)-3-(1H-indazol-5-ylmethylcarbamoyl)-5-phenyl-thiomorpholin-2-yl,
(3R)-3-(1H-indazol-5-ylmethylcarbamoyl)-5-(p-tolyl)thiomorpholin-2-yl, (3R)-5-(4-fluorophenyl)-3-(1H-indazol-5-ylmethylcarbamoyl)thiomorpholin-2-yl,
(3R)-5-(4-bromophenyl)-3-(1H-indazol-5-ylmethylcarbamoyl)thiomorpholin-2-yl,
(3R)-5-(4-chlorophenyl)-3-(1H-indazol-5-ylmethylcarbamoyl)thiomorpholin-2-yl,
(3R)-5-(4-cyclopropylphenyl)-3-(1H-indazol-5-ylmethylcarbamoyl)thiomorpholin-2-yl,
(3R)-3-(1H-indazol-5-ylmethylcarbamoyl)-5-[4-(trifluoromethyl)phenyl]thiomorpholin-2-yl,
(3R)-3-(3H-benzimidazol-5-ylmethylcarbamoyl)-5-phenyl-thiomorpholin-2-yl,
(3R)-3-(3H-benzimidazol-5-ylmethylcarbamoyl)-5-(p-tolyl)thiomorpholin-2-yl,
(3R)-3-(3H-benzimidazol-5-ylmethylcarbamoyl)-5-(4-fluorophenyl)thiomorpholin-2-yl,
(3R)-3-(3H-benzimidazol-5-ylmethylcarbamoyl)-5-[4-(trifluoromethyl)phenyl]thio-morpholin-2-yl,
(3R)-3-(3H-benzimidazol-5-ylmethylcarbamoyl)-5-(4-bromophenyl)thiomorpholin-2-yl,
(3R)-3-(3H-benzimidazol-5-ylmethylcarbamoyl)-5-(4-chlorophenyl)thiomorpholin-2-yl,
(3R)-3-(3H-benzimidazol-5-ylmethylcarbamoyl)-5-(4-cyclopropylphenyl)thio-morpholin-2-yl,
4-(1,3-benzodioxol-5-yl)-5-(4-fluorophenyl)thiomorpholin-2-yl,
4-(1,3-benzodioxol-5-yl)-5-(4-bromophenyl)thiomorpholin-2-yl,
4-(1,3-benzodioxol-5-yl)-5-(4-chlorophenyl)thiomorpholin-2-yl,
4-(1,3-benzodioxol-5-yl)-5-methyl-thiomorpholin-2-yl,
4-(1,3-benzodioxol-5-yl)-5-cyclopropyl-thiomorpholin-2-yl,
4-(1,3-benzodioxol-5-yl)-5-(4-cyclopropylphenyl)thiomorpholin-2-yl,
4-(1,3-benzodioxol-5-yl)-5-(p-tolyl)thiomorpholin-2-yl,
4-(1,3-benzodioxol-5-yl)-5-phenyl-thiomorpholin-2-yl,
4-(1,3-benzodioxol-5-yl)-5-[4-(trifluoromethyl)phenyl]thiomorpholin-2-yl,
4-(1,3-benzodioxol-5-yl)thiomorpholin-2-yl,
4-(1,3-benzodioxol-5-yl)-5-(4-fluorophenyl)-3-methyl-thiomorpholin-2-yl,
4-(1,3-benzodioxol-5-yl)-5-(4-bromophenyl)-3-methyl-thiomorpholin-2-yl,
4-(1,3-benzodioxol-5-yl)-5-(4-chlorophenyl)-3-methyl-thiomorpholin-2-yl,
4-(1,3-benzodioxol-5-yl)-3,5-dimethyl-thiomorpholin-2-yl,
4-(1,3-benzodioxol-5-yl)-5-cyclopropyl-3-methyl-thiomorpholin-2-yl,
4-(1,3-benzodioxol-5-yl)-5-(4-cyclopropylphenyl)-3-methyl-thiomorpholin-2-yl,
4-(1,3-benzodioxol-5-yl)-3-methyl-5-(p-tolyl)thiomorpholin-2-yl,
4-(1,3-benzodioxol-5-yl)-3-methyl-5-phenyl-thiomorpholin-2-yl,
4-(1,3-benzodioxol-5-yl)-3-methyl-5-[4-(trifluoromethyl)phenyl]thiomorpholin-2-yl,
4-(1,3-benzodioxol-5-yl)-3-methyl-thiomorpholin-2-yl,
5-(4-fluorophenyl)-4-(1H-indazol-6-yl)thiomorpholin-2-yl,
5-(4-bromophenyl)-4-(1H-indazol-6-yl)thiomorpholin-2-yl,
5-(4-chlorophenyl)-4-(1H-indazol-6-yl)thiomorpholin-2-yl,
4-(1H-indazol-6-yl)-5-methyl-thiomorpholin-2-yl,
5-cyclopropyl-4-(1H-indazol-6-yl)thiomorpholin-2-yl,
5-(4-cyclopropylphenyl)-4-(1H-indazol-6-yl)thiomorpholin-2-yl,
4-(1H-indazol-6-yl)-5-(p-tolyl)thiomorpholin-2-yl,
4-(1H-indazol-6-yl)-5-phenyl-thiomorpholin-2-yl,
4-(1H-indazol-6-yl)-5-[4-(trifluoromethyl)phenyl]thiomorpholin-2-yl,
4-(1H-indazol-6-yl)thiomorpholin-2-yl,
5-(4-fluorophenyl)-4-(1H-indazol-6-yl)-3-methyl-thiomorpholin-2-yl,
5-(4-bromophenyl)-4-(1H-indazol-6-yl)-3-methyl-thiomorpholin-2-yl,
5-(4-chlorophenyl)-4-(1H-indazol-6-yl)-3-methyl-thiomorpholin-2-yl,
4-(1H-indazol-6-yl)-3,5-dimethyl-thiomorpholin-2-yl,
5-(4-cyclopropylphenyl)-4-(1H-indazol-6-yl)-3-methyl-thiomorpholin-2-yl,
4-(1H-indazol-6-yl)-3-methyl-5-(p-tolyl)thiomorpholin-2-yl,
4-(1H-indazol-6-yl)-3-methyl-5-phenyl-thiomorpholin-2-yl,
5-cyclopropyl-4-(1H-indazol-6-yl)-3-methyl-thiomorpholin-2-yl,
4-(1H-indazol-6-yl)-3-methyl-thiomorpholin-2-yl,
4-(1H-indazol-6-yl)-3-methyl-5-[4-(trifluoromethyl)phenyl]thiomorpholin-2-yl,
4-(1H-benzimidazol-5-yl)-5-(4-fluorophenyl)thiomorpholin-2-yl,
4-(1H-benzimidazol-5-yl)-5-(4-bromophenyl)thiomorpholin-2-yl,
4-(1H-benzimidazol-5-yl)-5-(4-chlorophenyl)thiomorpholin-2-yl,
4-(1H-benzimidazol-5-yl)-5-methyl-thiomorpholin-2-yl,
4-(1H-benzimidazol-5-yl)-5-cyclopropyl-thiomorpholin-2-yl,
4-(1H-benzimidazol-5-yl)-5-(4-cyclopropylphenyl)thiomorpholin-2-yl,
4-(1H-benzimidazol-5-yl)-5-(p-tolyl)thiomorpholin-2-yl,
4-(1H-benzimidazol-5-yl)-5-phenyl-thiomorpholin-2-yl,
4-(1H-benzimidazol-5-yl)-5-[4-(trifluoromethyl)phenyl]thiomorpholin-2-yl,
4-(1H-benzimidazol-5-yl)thiomorpholin-2-yl,
4-(1H-benzimidazol-5-yl)-5-(4-fluorophenyl)-3-methyl-thiomorpholin-2-yl,
4-(1H-benzimidazol-5-yl)-5-(4-bromophenyl)-3-methyl-thiomorpholin-2-yl,
4-(1H-benzimidazol-5-yl)-5-(4-chlorophenyl)-3-methyl-thiomorpholin-2-yl,
4-(1H-benzimidazol-5-yl)-3,5-dimethyl-thiomorpholin-2-yl,
4-(1H-benzimidazol-5-yl)-5-cyclopropyl-3-methyl-thiomorpholin-2-yl,
4-(1H-benzimidazol-5-yl)-5-(4-cyclopropylphenyl)-3-methyl-thiomorpholin-2-yl,
4-(1H-benzimidazol-5-yl)-3-methyl-5-(p-tolyl)thiomorpholin-2-yl,
4-(1H-benzimidazol-5-yl)-3-methyl-5-phenyl-thiomorpholin-2-yl,
4-(1H-benzimidazol-5-yl)-3-methyl-5-[4-(trifluoromethyl)phenyl]thiomorpholin-2-yl,
4-(1H-benzimidazol-5-yl)-3-methyl-thiomorpholin-2-yl,
wherein the numbering of the thiomorpholine ring is as follow:

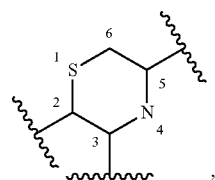

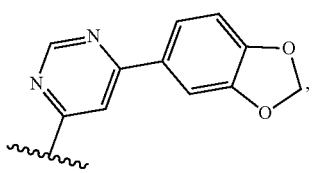
6-(1,3-benzodioxol-5-yl)pyrimidin-4-yl

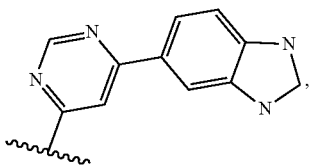
6-(1H-benzimidazol-5-yl)pyrimidin-4-yl

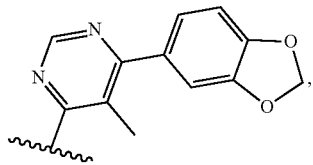
6-(1,3-benzodioxol-5-yl)-5-methyl-pyrimidin-4-yl

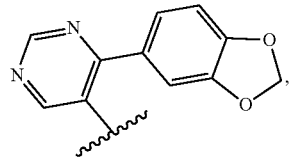
4-(1,3-benzodioxol-5-yl)pyrimidin-5-yl

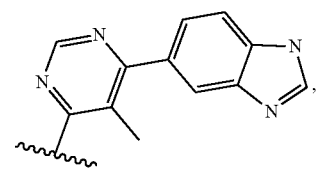
6-(1H-benzimidazol-5-yl)-5methyl-pyrimidin-4-yl

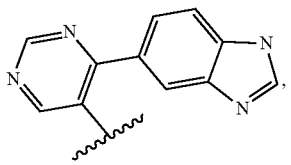
4-(1H-benzimidazol-5-yl)pyrimidin-5-yl

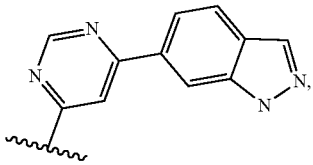
6-(1H-indazol-6-yl)pyrimidin-4-yl

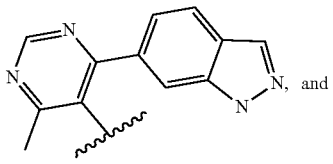
6-(1H-indazol-6-yl)-4-methyl-pyrimidin-5-yl

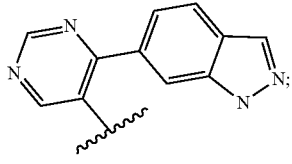
6-(1H-indazol-6-yl)pyrimidin-5-yl covalently bound to a second residue selected from the group consisting of hydrogen, methyl,

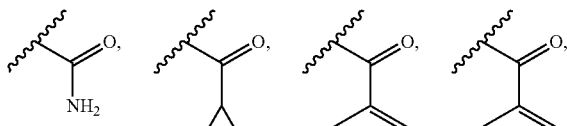

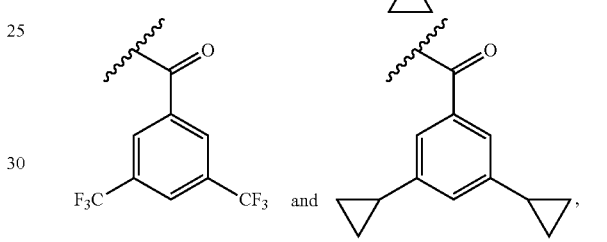

and (ii) a first residue selected from the group consisting of
6-(1,3-benzodioxol-5-yl)-2H-pyrimidin-1-yl,
6-(1,3-benzodioxol-5-yl)-4-methyl-2H-pyrimidin-1-yl,
6-(1H-benzimidazol-5-yl)-2H-pyrimidin-1-yl,
6-(1H-benzimidazol-5-yl)-4-methyl-2H-pyrimidin-1-yl,
6-(1,3-benzodioxol-5-yl)-4,5-dimethyl-2H-pyrimidin-1-yl,
6-(1,3-benzodioxol-5-yl)-5-methyl-2H-pyrimidin-1-yl,
6-(1H-benzimidazol-5-yl)-4,5-dimethyl-2H-pyrimidin-1-yl,
6-(1H-indazol-6-yl)-2H-pyrimidin-1-yl,
6-(1H-indazol-6-yl)-4-methyl-2H-pyrimidin-1-yl,
6-(1H-benzimidazol-5-yl)-5-methyl-2H-pyrimidin-1-yl,
6-(1H-indazol-6-yl)-4,5-dimethyl-2H-pyrimidin-1-yl,
6-(1H-indazol-6-yl)-5-methyl-2H-pyrimidin-1-yl,
wherein the 2H-pyrimidine ring is numbered as follows:

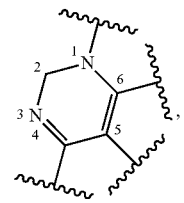 [SMILES: *C1=NCN(*)C(*)=C1*]

(4R)-3-(1,3-benzodioxol-5-ylmethylcarbamoyl)-4-[[3-(trifluoromethyl)phenyl]methyl-carbamoyl]pyrrolidin-1-yl,
(4R)-3-(1,3-benzodioxol-5-ylmethylcarbamoyl)-4-[[3,5-bis(trifluoromethyl)phenyl]-methylcarbamoyl]pyrrolidin-1-yl,
(4R)-3-(1,3-benzodioxol-5-ylmethylcarbamoyl)-4-[[4-(trifluoromethyl)phenyl]methyl-carbamoyl]pyrrolidin-1-yl, (4R)-3-(1,3-benzodioxol-5-ylmethylcarbamoyl)-4-[[3-(cyclopropylphenyl)phenyl]-methylcarbamoyl]pyrrolidin-1-yl,
(4R)-3-(1,3-benzodioxol-5-ylmethylcarbamoyl)-4-[[3,5-bis(cyclopropylphenyl)phenyl]-methylcarbamoyl]pyrrolidin-1-yl,
(4R)-3-(1,3-benzodioxol-5-ylmethylcarbamoyl)-4-[[4-(cyclopropylphenyl)phenyl]-methylcarbamoyl]pyrrolidin-1-yl,
(4R)-3-(1H-indazol-5-ylmethylcarbamoyl)-4-[[3-(trifluoromethyl)phenyl]methyl-carbamoyl]pyrrolidin-1-yl,
(4R)-3-(1H-indazol-5-ylmethylcarbamoyl)-4-[[3,5-bis(trifluoromethyl)phenyl]methyl-carbamoyl]pyrrolidin-1-yl,
(4R)-3-(1H-indazol-5-ylmethylcarbamoyl)-4-[[4-(trifluoromethyl)phenyl]methyl-carbamoyl]pyrrolidin-1-yl,
(4R)-3-(1H-indazol-5-ylmethylcarbamoyl)-4-[[3-(cyclopropyl)phenyl]methyl-carbamoyl]pyrrolidin-1-yl,
(4R)-3-(1H-indazol-5-ylmethylcarbamoyl)-4-[[3,5-bis(cyclopropyl)phenyl]methyl-carbamoyl]pyrrolidin-1-yl,
(4R)-3-(1H-indazol-5-ylmethylcarbamoyl)-4-[[4-(cyclopropyl)phenyl]methyl-carbamoyl]pyrrolidin-1-yl,
(4R)-3-(3H-benzimidazol-5-ylmethylcarbamoyl)-4-[[3-(trifluoromethyl)phenyl]methyl-carbamoyl]pyrrolidin-1-yl,
(4R)-3-(3H-benzimidazol-5-ylmethylcarbamoyl)-4-[[3,5-bis(trifluoromethyl)phenyl]-methylcarbamoyl]pyrrolidin-1-yl,
(4R)-3-(3H-benzimidazol-5-ylmethylcarbamoyl)-4-[[4-(trifluoromethyl)phenyl]methyl-carbamoyl]pyrrolidin-1-yl,
(4R)-3-(3H-benzimidazol-5-ylmethylcarbamoyl)-4-[[3-(cyclopropyl)phenyl]methyl-carbamoyl]pyrrolidin-1-yl,
(4R)-3-(3H-benzimidazol-5-ylmethylcarbamoyl)-4-[[3,5-bis(cyclopropyl)phenyl]methyl-carbamoyl]pyrrolidin-1-yl,
(4R)-3-(3H-benzimidazol-5-ylmethylcarbamoyl)-4-[[4-(cyclopropyl)phenyl]methyl-carbamoyl]pyrrolidin-1-yl,
(4R)-2-(1,3-benzodioxol-5-yl)-4-[[3-(trifluoromethyl)phenyl]methyl-carbamoyl]pyrrolidin-1-yl,
(4R)-2-(1,3-benzodioxol-5-yl)-4-[[3,5-bis(trifluoromethyl)phenyl]methylcarbamoyl]-pyrrolidin-1-yl,
(4R)-2-(1,3-benzodioxol-5-yl)-4-[[4-(trifluoromethyl)phenyl]methyl-carbamoyl]pyrrolidin-1-yl,
(4R)-2-(1,3-benzodioxol-5-yl)-4-methyl-pyrrolidin-1-yl,
(4R)-2-(1,3-benzodioxol-5-yl)-4-[[3-(cyclopropyl)phenyl]methylcarbamoyl]pyrrolidin-1-yl,
(4R)-2-(1,3-benzodioxol-5-yl)-4-[[3,5-bis(cyclopropyl)phenyl]methylcarbamoyl]pyrrolidin-1-yl,
(4R)-2-(1,3-benzodioxol-5-yl)-4-[[4-(cyclopropyl)phenyl]methylcarbamoyl]pyrrolidin-1-yl,
(4R)-2-(1H-indazol-5-yl)-4-[[3-(trifluoromethyl)phenyl]methyl-carbamoyl]pyrrolidin-1-yl,
(4R)-2-(1H-indazol-5-yl)-4-[[3,5-bis(trifluoromethyl)phenyl]methylcarbamoyl]pyrrolidin-1-yl,
(4R)-2-(1H-indazol-5-yl)-4-[[4-(trifluoromethyl)phenyl]methyl-carbamoyl]pyrrolidin-1-yl,
(4R)-2-(1H-indazol-5-yl)-3-methyl-pyrrolidin-1-yl,
(4R)-2-(1H-indazol-5-yl)-4-[[3-(cyclopropyl)phenyl]methylcarbamoyl]pyrrolidin-1-yl,
(4R)-2-(1H-indazol-5-yl)-4-[[3,5-bis(cyclopropyl)phenyl]methyl-carbamoyl]pyrrolidin-1-yl,
(4R)-2-(1H-indazol-5-yl)-4-[[4-(cyclopropyl)phenyl]methylcarbamoyl]pyrrolidin-1-yl,
(4R)-2-(3H-benzimidazol-5-yl)-4-[[3-(trifluoromethyl)phenyl]methyl-carbamoyl]pyrrolidin-1-yl,
(4R)-2-(3H-benzimidazol-5-yl)-4-[[3,5-bis(trifluoromethyl)phenyl]methylcarbamoyl]-pyrrolidin-1-yl,
(4R)-2-(3H-benzimidazol-5-yl)-4-[[4-(trifluoromethyl)phenyl]methyl-carbamoyl]pyrrolidin-1-yl,
(4R)-2-(3H-benzimidazol-5-yl)-3-methyl-pyrrolidin-1-yl,
(4R)-2-(3H-benzimidazol-5-yl)-4-[[3-(cyclopropyl)phenyl]methylcarbamoyl]pyrrolidin-1-yl,
(4R)-2-(3H-benzimidazol-5-yl)-4-[[3,5-bis(cyclopropyl)phenyl]methyl-carbamoyl]pyrrolidin-1-yl,
(4R)-2-(3H-benzimidazol-5-yl)-4-[[4-(cyclopropyl)phenyl]methylcarbamoyl]pyrrolidin-1-yl,
(4R)-2-(1,3-benzodioxol-5-yl)-3-methyl-4-[[3-(trifluoromethyl)phenyl]methyl-carbamoyl]pyrrolidin-1-yl,
(4R)-2-(1,3-benzodioxol-5-yl)-3-methyl-4-[[3,5-bis(trifluoromethyl)phenyl]methyl-carbamoyl]pyrrolidin-1-yl,
(4R)-2-(1,3-benzodioxol-5-yl)-3-methyl-4-[[4-(trifluoromethyl)phenyl]methyl-carbamoyl]pyrrolidin-1-yl],
(4R)-2-(1,3-benzodioxol-5-yl)-3-methyl-pyrrolidin-1-yl,
(4R)-2-(1,3-benzodioxol-5-yl)-3-methyl-4-[[3-(cyclopropyl)phenyl]methyl-carbamoyl]pyrrolidin-1-yl,
(4R)-2-(1,3-benzodioxol-5-yl)-3-methyl-4-[[3,5-bis(cyclopropyl)phenyl]methyl-carbamoyl]pyrrolidin-1-yl,
(4R)-2-(1,3-benzodioxol-5-yl)-3-methyl-4-[[4-(cyclopropyl)phenyl]methyl-carbamoyl]pyrrolidin-1-yl,
(4R)-2-(1H-indazol-6-yl)-3-methyl-4-[[3-(trifluoromethyl)phenyl]methyl-carbamoyl]pyrrolidin-1-yl,
(4R)-2-(1H-indazol-6-yl)-3-methyl-4-[[3,5-bis(trifluoromethyl)phenyl]methyl-carbamoyl]pyrrolidin-1-yl,
(4R)-2-(1H-indazol-6-yl)-3-methyl-4-[[4-(trifluoromethyl)phenyl]methyl-carbamoyl]pyrrolidin-1-yl,
(4R)-2-(1H-indazol-6-yl)-3-methyl-pyrrolidin-1-yl
(4R)-2-(1H-indazol-6-yl)-3-methyl-4-[[3-(cyclopropyl)phenyl]methyl-carbamoyl]pyrrolidin-1-yl,
(4R)-2-(1H-indazol-6-yl)-3-methyl-4-[[3,5-bis(cyclopropyl)phenyl]methyl-carbamoyl]pyrrolidin-1-yl,
(4R)-2-(1H-indazol-6-yl)-3-methyl-4-[[4-(cyclopropyl)phenyl]methyl-carbamoyl]pyrrolidin-1-yl,
(4R)-2-(1H-benzimidazol-5-yl)-4-[[3-(trifluoromethyl)phenyl]methyl-carbamoyl]pyrrolidin-1-yl,
(4R)-2-(1H-benzimidazol-5-yl)-4-[[3,5-bis(trifluoromethyl)phenyl]methyl-carbamoyl]pyrrolidin-1-yl,
(4R)-2-(1H-benzimidazol-5-yl)-4-[[4-(trifluoromethyl)phenyl]methyl-carbamoyl]pyrrolidin-1-yl,
(4R)-2-(1H-benzimidazol-5-yl)-3-methyl-pyrrolidin-1-yl,
(4R)-2-(1H-benzimidazol-5-yl)-4-[[3-(cyclopropyl)phenyl]methylcarbamoyl]pyrrolidin-1-yl,
(4R)-2-(1H-benzimidazol-5-yl)-4-[[3,5-bis(cyclopropyl)phenyl]methyl-carbamoyl]pyrrolidin-1-yl, and
(4R)-2-(1H-benzimidazol-5-yl)-4-[[4-(cyclopropyl)phenyl]methylcarbamoyl]pyrrolidin-1-yl, wherein the pyrrolidine ring is numbered as follows:

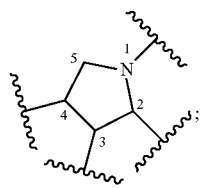 [SMILES: *C1CN(*)C(*)C1*]

covalently bound to a second residue selected from the group consisting of hydrogen, methyl,

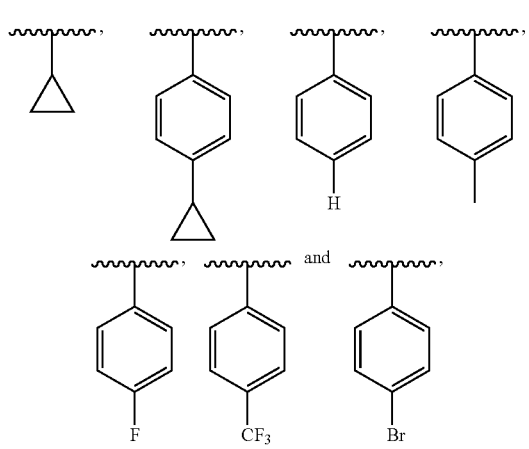

wherein the first residue is covalently bound to the second residue at the -yl position of the first residue;
preferably a compound selected from the group consisting of

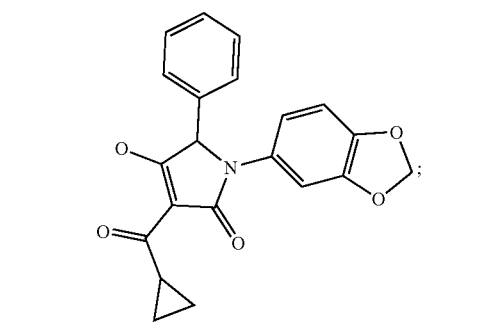

1-(1,3-benzodioxol-5-yl)-4-(cyclopropanecarbonyl)-3-hydroxy-2-phenyl-2H-pyrrol-5-one

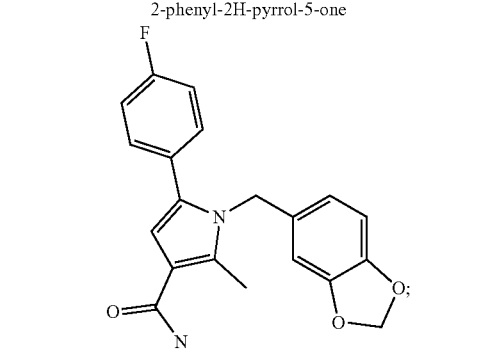

1-(1,3-benzodioxol-5-ylmethyl)-5-(4-fluorophenyl)-2-methyl-pyrrole-3-carboxamide

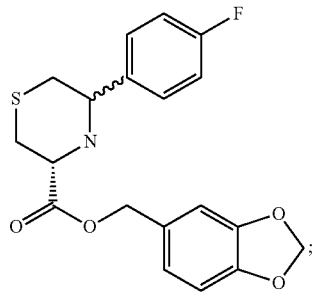

(3R)-N-(1,3-benzodioxol-5-ylmethyl)-5-(4-fluorophenyl)thiomorpholine-3-carboxamide

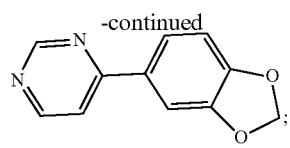

4-(1,3-benzodioxol-5-yl)pyrimidine

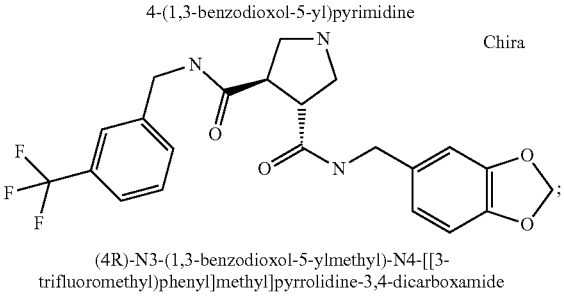

(4R)-N3-(1,3-benzodioxol-5-ylmethyl)-N4-[[3-(trifluoromethyl)phenyl]methyl]pyrrolidine-3,4-dicarboxamide

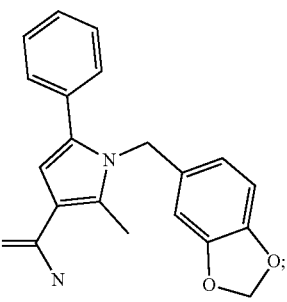

1-(1,3-benzodioxol-5-ylmethyl)-2-methyl-5-phenyl-pyrrole-3-carboxamide

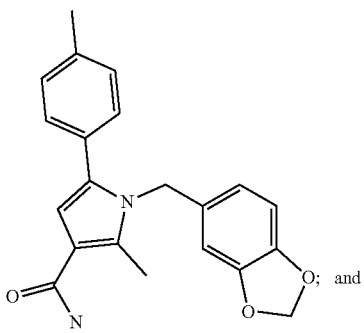

1-(1,3-benzodioxol-5-ylmethyl)-2-methyl-5-(p-tolyl)pyrrole-3-carboxamide

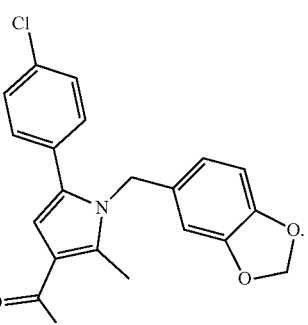

1-(1,3-benzodioxol-5-ylmethyl)-5-(4-chlorophenyl)-2-methyl-pyrrole-3-carboxamide In a further aspect, the present invention is directed to a compound selected from the group consisting of

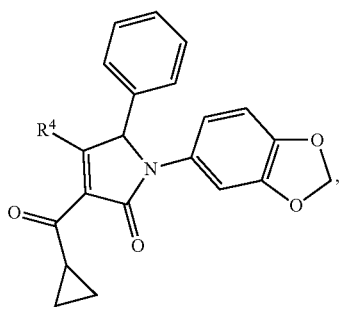

wherein R⁴ is selected from the group consisting of hydroxyl, —O—R¹⁴, and —O—C(=O)—R¹⁴, wherein R¹⁴ is selected from the group consisting of (aa) linear or branched, substituted or non-substituted ($C_{1-10}$)alkyl, preferably ($C_{1-5}$)alkyl, more preferably methyl, ethyl and propyl, most preferably methyl, ($C_{2-10}$)alkenyl, and ($C_{2-10}$)alkynyl;

(bb) substituted or non-substituted aromatic or non-aromatic ($C_{3-10}$)carbocycle, preferably ($C_{3-6}$)cycloalkyl, more preferably ($C_3$)carbocycle and ($C_6$)carbocycle, preferably ($C_6$)carbocycle, more preferably phenyl that is mono-substituted in para position by ($C_3$)carbocycle or —CF₃) or di-substituted in meta position by ($C_3$)carbocycle or —CF₃); and (cc) substituted or non-substituted aromatic or non-aromatic, preferably aromatic, ($C_{3-6}$)heterocycle having 1 to 3 heteroatoms each independently selected from N, O and S;

preferably a compound selected from the group consisting of

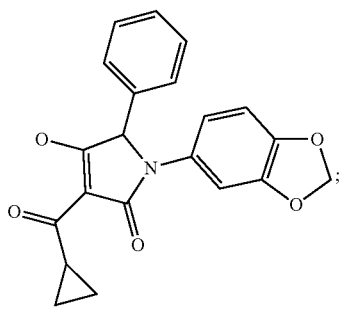

1-(1,3-benzodioxol-5-yl)-4-(cyclopropanecarbonyl)-3-hydroxy-2-phenyl-2H-pyrrol-5-one

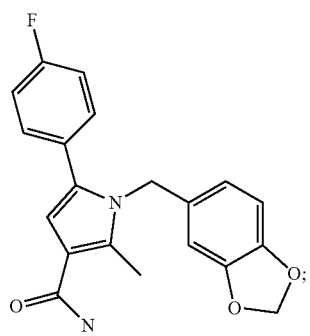

1-(1,3-benzodioxol-5-ylmethyl)-5-(4-fluorophenyl)-2-methyl-pyrrole-3-carboxamide

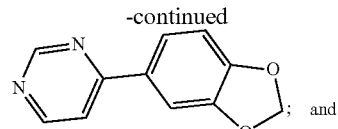

4-(1,3-benzodioxl-5-yl)pyrimidine

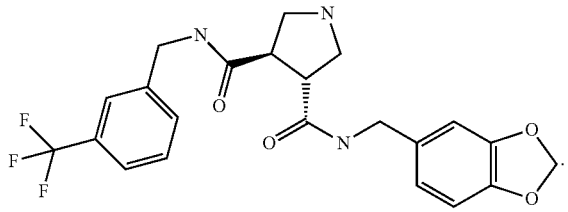

(4R)-N3-(1,3-benzodioxol-5-ylmethyl)-N4-[[3-trifluoromethyl)phenyl]methyl]pyrrolidine-3,4-dicarboxamide The compounds described herein are generally named by using the nomenclature that was computed based on the structural drawings by the software ACD/Chemsketch 2015 provided by Advanced Chemistry Development, Inc., Canada and BIOVIA Draw 2016 provided by BIOVIA, USA. For each molecule described herein, the description provides a structural formula that unambiguously numbers the residues of the rings of Formula I and II for the purposes of nomenclature. It is further noted that the structural formulae are binding and not the computed chemical names; in other words, if the name and the structural formula contradict each other, the structural formula prevails.

For compounds having asymmetric centers, it is understood that, unless otherwise specified, all of the optical isomers and mixtures thereof are encompassed. Each stereogenic carbon may be in the (R)- or (S)-configuration or a combination of configurations if not indicated differently. Also, compounds with two or more asymmetric elements can be present as mixtures of diastereomers. Furthermore, the compounds of the present invention preferably have a diastereomeric purity of at least 50%, preferably at least 60%, 70%, 80%, 85%, more preferably at least 90%, 95%, 96%, 97%, most preferably at least 98%, 99% or 100%. In addition, compounds with carbon-carbon double bonds may occur in Z- and E-forms, with all isomeric forms of the compounds being included in the present invention unless otherwise specified. Where a compound exists in various tautomeric forms, a recited compound is not limited to any one specific tautomer, but rather is intended to encompass all tautomeric forms.

For example, the compound depicted as follows:

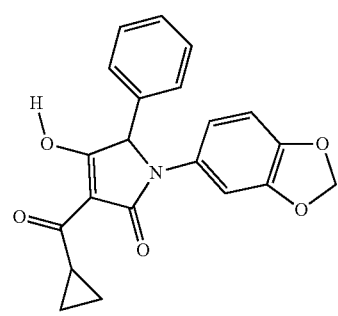 [SMILES: O=C(C1=C(O)C(c2ccccc2)N(c2ccc3c(c2)OCO3)C1=O)C1CC1]

encompasses the tautomeric form:

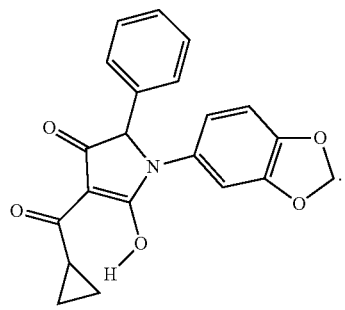 [SMILES: O=C(C1=C(O)N(c2ccc3c(c2)OCO3)C(c2ccccc2)C1=O)C1CC1]

Recited compounds are further intended to encompass compounds in which one or more atoms are replaced with an isotope, i.e., an atom having the same atomic number but a different mass number. By way of general example, and without limitation, isotopes of hydrogen include tritium and deuterium and isotopes of carbon include $^{11}C$, $^{13}C$, and $^{14}C$.

Compounds according to the formulas provided herein, which have one or more stereogenic center(s), have an enantiomeric excess of at least 50%. For example, such compounds may have an enantiomeric excess of at least 60%, 70%, 80%, 85%, preferably at least 90%, 95%, or 98%. Some embodiments of the compounds have an enantiomeric excess of at least 99%. It will be apparent that single enantiomers (optically active forms) can be obtained by asymmetric synthesis, synthesis from optically pure precursors, biosynthesis, e.g. using modified CYP102 (CYP BM-3) or by resolution of the racemates, e.g. enzymatic resolution or resolution by conventional methods such as crystallization in the presence of a resolving agent, or chromatography, using, for example, a chiral HPLC column.

As used herein, a "substituent" or "residue" or "R", refers to a molecular moiety that is covalently bound to an atom within a molecule of interest. For example, a "substituent", "R" or "residue" may be a moiety such as a halogen, alkyl group, haloalkyl group or any other substituent described herein that is covalently bonded to an atom, preferably a carbon or nitrogen atom, that that forms part of a molecule of interest. The term "substituted" as used herein, means that any one or more hydrogens on the designated atom is replaced with a selection from the indicated substituents, provided that the designated atom's normal valence is not exceeded, and that the substitution results in a stable compound, i.e., a compound that can be isolated and characterized using conventional means. For example, substitution can be in the form of an oxygen bound to any other chemical atom than carbon, e.g. hydroxyl group, or an oxygen anion. When a substituent is oxo, i.e., =O, then 2 hydrogens on the atom are replaced. An oxo group that is a substituent of an aromatic carbon atom results in a conversion of —CH— to —C(=O)— and a loss of aromaticity. For example, a pyridyl group substituted by oxo is a pyridone.

The term "heteroatom" as used herein shall be understood to mean atoms other than carbon and hydrogen such as and preferably O, N, S and P.

If a first compound, a substituent or a residue ends, e.g., in the name "-3-yl", this ending indicates that the first compound, substituent or residue is covalently bound to a second compound, substituent or residue at the atom number 3 position of the first compound. Of course, this definition holds true for any given integer before the "-yl" terminus of the compound's, substituent's or residue's name. For example, if 1-(1,3-benzodioxol-5-ylmethyl)pyrrol-3-yl is selected as a first residue to be covalently bound to the second residue

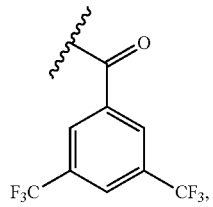

the following compound is formed:

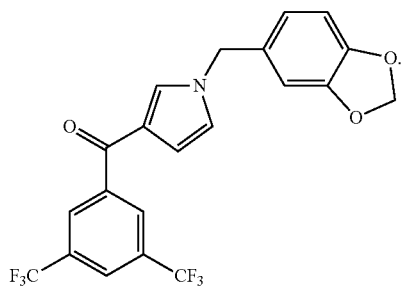 [SMILES: O=C(c1cc(C(F)(F)F)cc(C(F)(F)F)c1)c1ccn(Cc2ccc3c(c2)OCO3)c1]

In the context of the present invention it is understood that antecedent terms such as "linear or branched", "substituted or non-substituted" indicate that each one of the subsequent terms is to be interpreted as being modified by said antecedent term. For example, the scope of the term "linear or branched, substituted or non-substituted alkyl, alkenyl, alkynyl, carbocycle" encompasses linear or branched, substituted or non-substituted alkyl; linear or branched, substituted or non-substituted alkenyl; linear or branched, substituted or non-substituted alkynyl; linear or branched, substituted or non-substituted alkylidene; and linear or branched, substituted or non-substituted carbocycle. For example, the term "$(C_{2-10})$ alkenyl, alkynyl or alkylidene" indicates the group of compounds having 2 to 10 carbons and alkenyl, alkynyl or alkylidene functionality.

The expression "alkyl" refers to a saturated, straight-chain or branched hydrocarbon group that contains the number of carbon items indicated, e.g. "$(C_{1-10})$alkyl" denotes a hydrocarbon residue containing from 1 to 10 carbon atoms, e.g. a methyl, ethyl, propyl, iso-propyl, n-butyl, iso-butyl, sec-butyl, tert-butyl, n-pentyl, iso-pentyl, n-hexyl, 2,2-dimethylbutyl, etc.

The expression "alkenyl" refers to an at least partially unsaturated, substituted or non-substituted straight-chain or branched hydrocarbon group that contains the number of carbon atoms indicated, e.g. "$(C_{2-10})$alkenyl" denotes a hydrocarbon residue containing from 2 to 10 carbon atoms, for example an ethenyl (vinyl), propenyl (allyl), iso-propenyl, butenyl, isoprenyl or hex-2-enyl group, or, for example, a hydrocarbon group comprising a methylene chain interrupted by one double bond as, for example, found in monounsaturated fatty acids or a hydrocarbon group comprising methylene-interrupted polyenes, e.g. hydrocarbon groups comprising two or more of the following structural unit —[CH=CH—CH$_2$]—, as, for example, found in polyunsaturated fatty acids. Alkenyl groups have one or more, preferably 1, 2, 3, 4, 5, or 6 double bond(s).

The expression "alkynyl" refers to at least partially unsaturated, substituted or non-substituted straight-chain or branched hydrocarbon groups that contain the number of carbon items indicated, e.g. "$(C_{2-10})$alkynyl" denotes a hydrocarbon residue containing from 2 to 10 carbon atoms, for example an ethinyl, propinyl, butinyl, acetylenyl, or propargyl group. Preferably, alkynyl groups have one or two (especially preferably one) triple bond(s).

Furthermore, the terms "alkyl", "alkenyl" and "alkynyl" refer to groups in which one or more hydrogen atom(s) have been replaced, e.g. by a halogen atom, preferably F or $C_1$, such as, for example, a 2,2,2-trichloroethyl or a trifluoromethyl group.

The term "carbocycle" shall be understood to mean a substituted or non-substituted aliphatic hydrocarbon cycle containing the number of carbon items indicated, e.g. "$(C_{3-10})$carbocycle" or from 3 to 20, preferably from 3 to 12 carbon atoms, more preferably 5 or 6 carbon atoms. These carbocycles may be either aromatic or non-aromatic systems. The non-aromatic ring systems may be mono- or polyunsaturated.

The term "carbobicycle" refers to a carbocycle as defined above comprising more than 1 ring, preferably two rings. Preferred carbocycles and carbobicycles include but are not limited to cyclopropyl, cyclobutyl, cyclopentyl, cyclopentenyl, cyclohexyl, cyclohexenyl, cycloheptanyl, cycloheptenyl, phenyl, indanyl, indenyl, benzocyclobutanyl, dihydronaphthyl, tetrahydro-naphthyl, naphthyl, decahydronaphthyl, benzocycloheptanyl, benzocycloheptenyl, spiro[4,5]de-canyl, norbornyl, decalinyl, bicyclo[4.3.0]nonyl, tetraline, or cyclopentylcyclohexyl. The carbo- and/or carbobicyclic residue may be bound to the remaining structure of the complete molecule by any atom of the cycle, which results in a stable structure The term "carbocycle" shall also include "cycloalkyl" which is to be understood to mean aliphatic hydrocarbon-containing rings preferably having from 3 to 12 carbon atoms. These non-aromatic ring systems may be mono- or polyunsaturated, i.e. the term encompasses cycloalkenyl and cycloalkynyl.

The term "heterocycle" refers to a stable substituted or non-substituted, aromatic or non-aromatic, preferably 3 to 20 membered, more preferably 3-12 membered, most preferably 5 or 6 membered, monocyclic, heteroatom-containing cycle. Each heterocycle consists of carbon atoms and one or more, preferably 1 to 4, more preferably 1 to 3 heteroatoms preferably chosen from nitrogen, oxygen and sulphur. A heterocycle may contain the number of carbon atoms in addition to the non-carbon atoms as indicated: a "$(C_{3-6})$heterocycle" is meant to have 3 to 6 carbon atoms in addition to a given number of heteroatoms.

The term "heterobicycle" refers to a heterocycle as defined above comprising more than 1 ring, preferably two rings.

The hetero- and/or heterobicyclic residue may be bound to the remaining structure of the complete molecule by any atom of the cycle, which results in a stable structure. Exemplary hete-rocycles and heterobicycles include, but are not limited to pyrrolidinyl, pyrrolinyl, morpholinyl, thiomorpholinyl, thiomorpholinyl sulfoxide, thiomorpholinyl sulfone, dioxalanyl, piperidinyl, piperazinyl, tetrahydrofuranyl, 1-oxo-A4-thiomorpholinyl, 13-oxa-11-aza-tricyclo[7.3.1.0-2,7]-tridecy-2,4,6-triene, tetrahydropyranyl, 2-oxo-2H-pyranyl, tetrahydrofuranyl, 1,3-dioxolanone, 1,3-dioxanone, 1,4-dioxanyl, 8-oxa-3-aza-bicyclo[3.2.1]octanyl, 2-oxa-5-aza-bicyclo[2.2.1]heptanyl, 2-thia-5-aza-bicyclo[2.2.1]heptanyl, piperidinonyl, tetrahydropyrimidonyl, pentamethylene sulphide, pentamethylene sulfoxide, pentamethylene sulfone, tetramethylene sulphide, tetramethylene sulfoxide and tetramethylene sulfone, indazolyl, benzimidazolyl, benzodioxolyl, imidazolyl, 1,3-benzodioxolyl and pyrazolyl.

The expressions "alkyl/alkenyl/alkynyl ether" refer to a saturated or non-saturated, straight-chain or branched hydrocarbon group that contains the number of carbon items indicated. For example, "$(C_{1-10})$alkyl ether" denotes a hydrocarbon residue containing from 1 to 10 carbon atoms, and any suitable number of oxygen atoms that will result in an ether structure. Alkyl/alkenyl/alkynyl ether groups as used herein shall be understood to mean any linear or branched, substituted or non-substituted alkyl/alkenyl/alkynyl chain comprising an oxygen atom either as an ether motif, i.e. an oxygen bound by two carbons. The ether residue can be attached to the Formulas provided in the present invention either via the carbon atom or via the oxygen atom of the ether residue.

The "substituent" or "residue" or "R" as used herein, preferably $R^2$, $R^3$, $R^4$, $R^5$, $R^6$, $R^7$, $R^8$, $R^9$, $R^{10}$ and/or $R^{11}$ can be attached directly to the Formulas provided in the present invention or by means of a linker. Said linker can also be in the form of polyethyleneglycol. The term polyethyleneglycol as used herein refers to a chain of substituted or non-substituted ethylene oxide monomers.

As used herein, the terms "nitrogen" or "N" and "sulphur" or "S" include any oxidized form of nitrogen and sulphur and the quaternized form of any basic nitrogen as long as the resulting compound is chemically stable. For example, for an —S—$C_{1-6}$ alkyl radical shall be understood to include —S(O)—$C_{1-6}$ alkyl and —S(O)$_2$-$C_{1-6}$ alkyl.

A residue connected via a given position to a second compound of interest is to be understood as a residue that is covalently bound to the second compound at the atom position indicated. For example, indazolyl connected via position (5) of the indazolyl denotes the following residue:

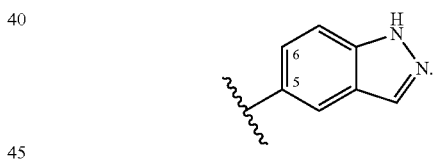

In this case, the numbering starts—as customary in the art—on the 1H-nitrogen. However, it is noted that some nomenclature may provide a different starting point for the numbering. For example, a 1H-benzimidazol-6-yl residue is identical to a 3H-benzimidazol-5-yl residue, as is understood by the skilled person.

As used herein, a wording defining the limits of a range of length such as, e. g., "from 1 to 5" or "(Cm)" means any integer from 1 to 5, i. e. 1, 2, 3, 4 and 5. In other words, any range defined by two integers explicitly mentioned is meant to comprise and disclose any integer defining said limits and any integer comprised in said range.

By way of example, the term "mono- or di-substituted in meta position or mono-substituted in para position", as used herein, means that a compound is either substituted by at least one given substituent in para position to the position where the compound is attached to another compound or residue, or substituted in two of its meta positions by at least one substituent. For example, the term "di-substituted in meta position by $(C_3)$carbocycle or —$(CF_3)$" denotes that a compound is substituted by one $(C_3)$carbocycle or —$(CF_3)$ in each meta position or by a (C₃)carbocycle in one meta position and by —(CF₃) in the other meta position. Preferably, the term denotes that a compound is substituted by one (C₃)carbocycle in each meta position or by one —(CF₃) in each meta position, i.e. is substituted in both meta positions by the same substituent. As denoted above for the para position, the meta position denotes the position meta to the position where the compound is attached to another compound or residue.

As an example, the term "phenyl, preferably mono-substituted in para or meta position by cyclopropyl or —(CF₃), or di-substituted in meta position by cyclopropyl or —(CF₃) in each meta position" preferably denotes the following structures:

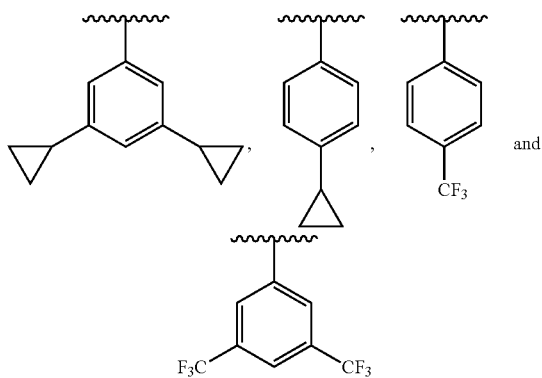

The residues $R^1$, $R^5$ and/or $R^9$ for use in the present invention are preferably phenyl that is mono-substituted in para position by a group consisting of Cl, F, Br, substituted or non-substituted methyl, preferably —(CF₃), ethyl, propyl and cyclopropyl. The residues $R^{12}$ and $R^{13}$ for use in the present invention are preferably (C₆)carbocycle, more preferably phenyl that is mono-substituted in para position by a (C₃)carbocycle, preferably cyclopropyl, or —(CF₃), or di-substituted in meta position by (C₃)carbocycle, preferably cyclopropyl, or (—CF₃). It is further preferred that $R^1$, $R^5$, $R^9$, $R^{12}$ and/or $R^{13}$ are phenyl that is mono-, di- or tri-substituted in ortho, meta and/or para position by a group consisting of Cl, F, Br, substituted or non-substituted methyl, preferably —(CF₃), ethyl, propyl and cyclopropyl. The di- or tri-substituted phenyl representing $R^1$, $R^5$, $R^9$, $R^{12}$ and/or $R^{13}$ can be di- or tri-substituted phenyl that is substituted with the same substituent in the respective ortho, meta and para position or by different substituents in the respective ortho, meta and/or para position, wherein the substituents are selected from the group consisting of Cl, F, Br, substituted or non-substituted methyl, preferably —(CF₃), ethyl, propyl and cyclopropyl. Each combination and number of substituents selected from the group consisting of Cl, F, Br, substituted or non-substituted methyl, preferably —(CF₃), ethyl, propyl and cyclopropyl in ortho, meta and/or para position of the phenyl representing $R^1$, $R^5$, $R^9$, $R^{12}$ and/or $R^{13}$ is explicitly disclosed herein.

The scope of the present invention includes those analogs of the compounds as described above and in the claims that, e.g. for reasons of metabolic stability, feature the exchange of one or more carbon-bonded hydrogens, preferably one or more aromatic carbon-bonded hydrogens, with halogen atoms such as F, Cl, or Br, preferably F. For example, Compound-1 can feature one or more halogen atoms, preferably F, instead of the aromatic carbon-bonded hydrogens in the phenyl ring or instead of the aromatic or non-aromatic carbon-bonded hydrogens in the 1,3-benzodioxol-5-yl-moiety. Also, for example, Compound-4 can feature one or more halogen atoms, preferably F, instead of the aromatic carbon-bonded hydrogens in the pyrimidine ring or instead of the aromatic or non-aromatic carbon-bonded hydrogens in the benzodioxole moiety.

In a preferred embodiment, the present invention is directed to a compound for use or to a compound as such as described above, wherein the compound inhibits phosphorylation of serine/arginine-rich splicing factor 1 (SRSF1, ASF-1, SF2) or phosducin, preferably by G-protein-coupled receptor kinase 2 (GRK2, ADRBK1).

In another aspect, the present invention is directed to a pharmaceutical composition, comprising as active substance a compound for use or a compound as such as described above or a pharmaceutically acceptable derivative thereof, optionally combined with excipients and/or carriers.

The invention includes pharmaceutically acceptable salts or solvates of the compounds of Formula (I) and (II) of the present invention. A "pharmaceutically acceptable salt or solvate" refers to any pharmaceutically acceptable salt, solvate or ester or any other compound which, upon administration to a patient, is capable of providing (directly or indirectly) a compound of the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the present invention.

Pharmaceutically acceptable salts include those derived from pharmaceutically acceptable inorganic and organic acids and bases. Examples of suitable acids include hydrochloric, hydro-bromic, sulphuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphtha-lene-2-sulfuric and benzenesulfonic acids. Other acids, such as oxalic acid, while not themselves pharmaceutically acceptable, may be employed in the preparation of salts useful as interme-diates in obtaining the compounds and their pharmaceutically acceptable acid addition salts. Salts derived from appropriate bases include alkali metal (e.g., sodium), alkaline earth metal (e.g. magnesium), ammonium and N—(C₁-C₄alkyl)₄⁺ salts.

In addition, the scope of the invention also encompasses prodrugs of compounds of the present invention. Prodrugs include those compounds that, upon simple chemical trans-for-mation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

In a preferred embodiment, the compounds for use according to the present invention are for use in a cardioprotective treatment selected from the group consisting of
(i) risk reduction of cardiovascular mortality and/or morbidity under conditions of essential hypertension and/or chronic hypertension;
(ii) risk reduction of cardiovascular disease-induced ageing;
(iii) risk reduction of cardiovascular mortality and/or morbidity under conditions of left ventricular dysfunction and signs of heart failure after recent myocardial infarction;
(iv) risk reduction of cardiovascular mortality and/or morbidity under conditions of chronic heart failure and left ventricular dysfunction;

(v) risk reduction of cardiovascular mortality and/or morbidity under conditions of dilated cardiomyopathy;
(vi) risk reduction of cardiovascular mortality and/or morbidity under conditions of left ventricular dysfunction;
(vii) risk reduction of cardiovascular mortality and/or morbidity under conditions of cardiomyocyte necrosis;
(viii) risk reduction of cardiovascular mortality and/or morbidity under conditions of cardiac fibrosis;
(ix) prevention, preferably primary prevention, of cardiomyocyte necrosis and/or dilated cardiomyopathy, preferably under conditions with increased risk for ischemic cardiac diseases and ischemic heart damage, preferably as a consequence of cardiovascular risk factors selected from the group consisting of hypertension, atherosclerosis, chronic and acute stress, depression, diabetes mellitus, chronic heart failure, angina pectoris, atrial fibrillation, chronic renal failure and aging;
(x) prevention, preferably secondary prevention, of cardiomyocyte necrosis and/or dilated cardiomyopathy in patients with previous events selected from the group consisting of acute cardiovascular disease, myocardial infarction, ischemic heart disease, angina pectoris, atrial fibrillation, decompensated and chronic heart failure, and cerebrovascular stroke; and
(xi) treatment of acute disease states of cardiovascular disease, preferably selected from the group consisting of myocardial infarction, angina pectoris, ischemic heart disease, cerebrovascular disease and decompensated heart failure;
wherein the compound or pharmaceutical composition as described above is for use in the treatment of animals or humans, preferably mammalians, more preferably humans.

Also, the compounds of the present invention inhibit cell-damaging SRSF1 phosphorylation in human kidney cells causing, e.g. a pro-survival activity on human kidney cells. Therefore, in a preferred embodiment, the compounds of the present invention are fore use in the treatment of patients with various forms of kidney disease and nephropathies, e.g. nephropathies caused by hypertension, renal artery stenosis, heart failure, ischemia, diabetes and/or toxic agents.

For therapeutic use, the compounds of the invention may be administered in any conventional dosage form in any conventional manner. Routes of administration include, oral, intravenous, intramuscular and subcutaneous injections. The preferred modes of administration are oral, intravenous or subcutaneous.

The compounds may be administered alone or in combination with adjuvants that enhance stability of the compounds, facilitate administration of pharmaceutical compositions containing them in certain embodiments, provide increased dissolution or dispersion, increase activity, provide adjunct therapy (e.g. a beta-adrenoceptor antagonists, an ACE inhibitor, an angiotensin receptor antagonist, a mineral corticoid receptor antagonist, ivabradin, a calcium channel antagonist and/or diuretic), and the like, including other active ingredients. Advantageously such combination therapies utilize lower dosages of the conventional therapeutics, thus avoiding possible toxicity and adverse side effects incurred when those agents are used as monotherapies. The above described compounds may be physically combined with conventional therapeutics or other adjuvants into a single pharmaceutical composition. Reference in this regard may be made to Cappola et al.: U.S. patent application Ser. No. 09/902,822, PCT/US 01/21860 and U.S. provisional application No. 60/313,527, each incorporated by reference herein in their entirety. Advantageously, the compounds may then be administered together in a single dosage form. In some embodiments, the pharmaceutical compositions comprising such combinations of compounds contain at least about 5%, but more preferably at least about 20%, of a compound of the present invention (w/w). The optimum percentage (w/w) of a compound of the invention may vary and is within the purview of those skilled in the art. Alternatively, the compounds may be administered separately (either serially or in parallel). Separate dosing allows for greater flexibility in the dosing regime.

As mentioned above, dosage forms of the compounds described herein include pharmaceutically acceptable carriers and adjuvants known to those of ordinary skill in the art. Methods for preparing such dosage forms are known (see, for example, H. C. Ansel and N. G. Popovish, *Pharmaceutical Dosage Forms and Drug Delivery Systems*, $5^{th}$ ed., Lea and Febiger (1990)). Dosage levels and requirements are well-recognized in the art and may be selected by those of ordinary skill in the art from available methods and techniques suitable for a particular patient. In some embodiments, dosage levels range from 1-300 mg/dose for a 70 kg patient. Although one dose per day may be sufficient, up to 5 doses per day may be given. For oral doses, up to 2000 mg/day may be required. Reference in this regard may also be made to U.S. provisional application No. 60/339,249. As the skilled artisan will appreciate, lower or higher doses may be required depending on particular factors. For instance, specific doses and treatment regimens will depend on factors such as the patient's general health profile, the severity and course of the patient's disorder or disposition thereto, and the judgment of the treating physician.

In another aspect, the present invention is directed to a method for cell-protective, preferably cardio- or renal-protective treatment in a patient, preferably in a mammalian patient, more preferably in a human patient, the method comprising the step of administering a therapeutically effective amount of a compound according to the present invention or an effective amount of the pharmaceutical composition according to the present invention to a patient in need of such treatment.

In another aspect, the present invention is directed to a method for the identification of inhibitors of the G-protein-coupled receptor kinase 2 (GRK2), preferably by determination of the GRK2-mediated phosphorylation of serine/arginine-rich splicing factor 1 (SRSF1) and/or phosducin comprising the steps of
(i) providing and incubating GRK2 and SRSF1 or phosducin under physiological conditions suitable for the phosphorylation of SRSF1 or phosducin in the presence and in the absence of a compound of interest;
(ii) determining the phosphorylation of SRSF1 or phosducin in the presence and in the absence of the compound of interest;
(iii) identifying the compound of interest as an inhibitor or non-inhibitor based on the phosphorylation of SRSF1 or phosducin in the presence of the compound of interest relative to the phosphorylation of SRSF1 or phosducin in the absence of the compound of interest.

In a preferred embodiment, the method for the identification as described above is a method wherein
(a) in step (i), the incubation is performed in the presence of radioactively labeled ATP, preferably [gamma-$^{32}$P]ATP, preferably at about 25 to 40° C. for about 30 to 90 min; and/or
(b) the incubation of step (i) is stopped by dilution at temperatures below 30° C., preferably at temperatures of about 0 to 10° C.; and/or (c) the determination of the phosphorylation of SRSF1 or phosducin in step (ii) is performed by (A) filtering the product of (i) through a filter, preferably a glass fiber filter; (B) washing the filter; and (C) determining the filter-bound radioactivity, preferably with a β-counter.

A non-limiting and representative example for a method for the identification of inhibitors of the (GRK2)-mediated phosphorylation of (SRSF1) and (phosducin) is provided in Example 13 and Example 5 below. For example, for the identification of small molecule inhibitors of the (GRK2)-mediated phosphorylation of (SRSF1) and (phosducin), the phosphorylation assay can be performed in a reaction buffer (e.g. 20 mM Tris, 2 mM EDTA, 5 mM MgCl2, 0.05% BSA, pH 7.5, or 20 mM Hepes, 2 mM MgCl2, 0.025% DDM (=n-Dodecyl beta-D-maltoside), pH 7.4) supplemented with ATP, preferably about 5 microM, [gamma-32P]-ATP (e.g. 1×10 6 DPM, specific activity of about 3000 Ci/mmol)) and about 300-500 nM of SRSF1 (or phosducin). The reaction mixture is added to GRK2 or GRK2-5670A (e.g. about 60 nM in reaction buffer, without or with increasing concentrations of the small molecule compound) to give a final reaction volume of, e.g. about 50 microL. After an incubation for e.g. about 30-60 min at about 30° C., the phosphorylation can be stopped by the addition of ice-cold reaction buffer, preferably about 5 volumes. The reaction mixture is immediately applied to filters, preferably glass fiber filters. After three washing steps, e.g. with about 5 ml of reaction buffer, filter-bound radioactivity can be determined in a β-counter.

Also, the compounds of the present invention can be used as markers for altered GRK2 activity.

The following Figures and Examples serve to illustrate the invention and are not intended to limit the scope of the invention as described in the appended claims.

In the Figures and Examples, the following names are attributed to the respective compounds of the present invention and control compounds:

Compound-1: 1-(1,3-benzodioxol-5-yl)-4-(cyclopropanecarbonyl)-3-hydroxy-2-phenyl-2H-pyrrol-5-one;

Compound-2: 1-(1,3-benzodioxol-5-ylmethyl)-5-(4-fluorophenyl)-2-methyl-pyrrole-3-carboxamide;

Compound-3: (3R)—N-(1,3-benzodioxol-5-ylmethyl)-5-(4-fluorophenyl)thiomorpholine-3-carboxamide;

Compound-4: 4-(1,3-benzodioxol-5-yl)pyrimidine;

Compound-5: (4R)-N3-(1,3-benzodioxol-5-ylmethyl)-N4-[[3-(trifluoromethyl)phenyl]-methyl]pyrrolidine-3,4-dicarboxamide;

Compound-22: 1-(1,3-benzodioxol-5-ylmethyl)-2-methyl-5-phenyl-pyrrole-3-carboxamide;

Compound-23: 1-(1,3-benzodioxol-5-ylmethyl)-2-methyl-5-(p-tolyl)pyrrole-3-carboxamide;

Compound-24: 1-(1,3-benzodioxol-5-ylmethyl)-5-(4-chlorophenyl)-2-methyl-pyrrole-3-carboxamide;

Compound-6: Ibuprofen ((±)-2-(4-isobutylphenyl)propanoic acid) (reference compound, Sigma-Aldrich, St. Louis, USA);

FIGS. 1A-E: Identification of SRSF1 as Novel Non-Receptor GRK2 Substrate

A, Left panel: Enrichment of GRK2 by immunoaffinity chromatography from heart biopsy specimens from heart failure patients, and detection of enriched GRK2 and co-enriched SRSF1 in immunoblot. Right panel: Nano-LC-ESI-MS/MS analysis identified SRSF1 (Serine/arginine-rich splicing factor 1, ASF/SF2, SEQ ID NO: 7) as a previously unrecognized GRK2-interacting protein in heart biopsy specimens from heart failure patients. B, GRK2 phosphorylates SRSF1 in an in vitro kinase assay. Nano-LC-ESI-MS/MS analysis Identification of phospho-containing peptides with serine199/201 as GRK2 phosphorylation site(s) (SEQ ID NO: 8 and SEQ ID NO: 9). C, Paroxetine inhibits the GRK2-mediated phosphorylation of SRSF1 with a half maximum inhibitory concentration (IC50 value) of 2.38 μM (n=4). D, Inhibition of GRK2-mediated SRSF1 phosporylation by GRKInh, another cardio-protective GRK2 inhibitor. E, Immunoblot detection of the activating phosphorylation of SRSF1 by GRK2 with phospho-specific SR antibody 1H4 (p-SRSF1).

FIGS. 2A-2L: GRK2 Induces Activating Srsf1 Phosphorylation In Vivo

A, B, Generation of Tg-GRK2 mice with myocardium-specific expression of GRK2 under control of the alpha-MHC promoter (A) and immunoblot detection of increased GRK2 protein in heart lysates from Tg-GRK2 mice relative to non-transgenic B6 controls (B, C; n=4 hearts/group). D, Tg-GRK2 mice have a decreased left ventricular ejection fraction as determined by echocardiography (±s.d., n=6). E-G, Immunoblot detection of increased p-Srsf1 (right) and Camk2d isoforms B and C contents in heart lysates from Tg-GRK2 mice relative to non-transgenic controls (n=4/group). H, Myocardial necrosis in Tg-GRK2 hearts was determined by von Kossa stain (n=6; ±s.d.), bar: 100 micron. I, J, Immunoblot detection of pSrsf1 (I) and Camk2d isoforms B/C (J) in Tg-GRK2 hearts transduced with a control lentivirus or a lentivirus targeting Srsf1 by a miRNA (+miSrsf1). K, Down-regulation of Srsf1 by miSrsf1 retards the development of cardiac dysfunction in Tg-GRK2 mice (n=4, ±s.d.). L, Myocardial necrosis was determined with von Kossa stain (n=6; ±s.d.).

FIGS. 3A-F: Transgenic Overexpression of SRSF1 Induces Enhanced Camk2d Splicing and Signs of Heart Failure A, Generation of transgenic mice with myocardium-specific SRSF1 expression under control of the myocardium-specific alpha-MHC Promoter. B, Increased cardiac SRSF1/Srsf1 protein of Tg-SRSF1 mice was detected in immunoblot (n=4 hearts/group). C, Enhanced cardiac splicing of Camk2d protein isoforms B and C in Tg-SRSF1 mice (n=4 hearts/group). D, Myocardial necrosis in Tg-SRSF1 hearts was determined with von Kossa stain (n=5, ±s.d.). E, Histological assessment of a Tg-SRSF1 heart shows cardiac hypertrophy with dilation relative to the non-transgenic B6 control. Cardiac sections were stained with hematoxylin-eosin (HE) and are representative of 4 mice/group. F, Cardiac dysfunction of Tg-SRSF1 mice relative to non-transgenic B6 controls was determined by echocardiography (n=5; ±s.d.).

FIGS. 4A-D: Inhibition of GRK2 In Vivo Retards Activating Srsf1 Phosphorylation, and Signs of Heart Failure in a Chronic Pressure Overload Model of Cardiac Dysfunction A, Generation of transgenic mice with myocardium-specific expression of dominant-negative GRK2-K220R and immunoblot detection of GRK2-K220R in Tg-GRK2-K220R hearts (n=3 (B6 controls) and n=5 (Tg-GRK2-K220R hearts). B, Immunoblot detection of cardiac pSrsf1 and Camk2d isoforms B/C in hearts from 4 month-old B6 controls (B6), Tg-GRK2-K220R and Tg-GRKInh mice with 8 weeks of chronic pressure overload imposed by abdominal aortic constriction (AAC); n=4 mice/group. C, Myocardial necrosis was determined by von Kossa stain (n=6/group; ±s.d.).D, Cardiac dysfunction in B6 mice with 8 weeks of AAC was retarded by GRK2 inhibition with GRK2-K220R or GRKInh (n=6/group; ±s.d.).

FIGS. 5A-G: The GRK2 Inhibitor RKIP does not Inhibit Activating Srsf1 Phosphorylation and Induces Signs of Heart Failure In Vivo A, Human RKIP does not inhibit the phosphorylation of SRSF1 by GRK2 in vitro. In contrast, human RKIP inhibited the phosphorylation of phosducin by GRK2 (IC50=950 nM, n=6-7). B, C, Immunoblot detection of cardiac RKIP in Tg-RKIP2 and Tg-RKIP3 line with myocardium-specific expression of human RKIP (B; n=3 mice/group), and reduced left ventricular ejection fraction of Tg-RKIP2 and Tg-RKIP3 line (n=5/group; ±s.d.). D, Histological assessment of an 8 month-old Tg-RKIP2 heart relative to B6 and Tg-GRK2-K220R hearts (left) and heart-weight to body-weight determination (n=6, ±s.d). Histological sections are representative of 4 hearts/group. E, F, Cardiac fibrosis was determined with picrosirius red staining (E) and necrosis was determined by von Kossa stain (F) in Tg-RKIP2 hearts, B6 and Tg-GRK2-K220R hearts (n=6; ±s.d.). G, Immunoblot detection of cardiac Srsf1 (total Srsf1) and activated phosphorylated p-Srsf1 in heart lysates from the different groups of mice (n=3/group).

FIGS. 6A-G: Tg-RKIP Mouse Lines in the FVB Background Also Develop Signs of Heart Failure A, Immunoblot detection of human/mouse RKIP in Tg-RKIP mouse lines generated in the FVB background (n=8/group, ±s.d.). B, Immunohistological detection of the RKIP protein in a Tg-RKIP1 heart relative to a non-transgenic FVB control. Immunohistology is representative of 4 hearts/group. C, D, Left ventricular ejection fraction (C; n=5) and heart-weight to body-weight ratio of Tg-RKIP1 and Tg-RKIP2 mice relative to non-transgenic FVB controls (n=6; ±s.d.). E, Histological analysis of Tg-RKIP hearts relative to a non-transgenic FVB control. The histological sections are representative of four mice/group. F, G, Left ventricular ejection fraction of Tg-RKIP1 and TgRKIP2 mice relative to non-transgenic FVB controls, and RNAi-mediated down-regulation of human RKIP by lentiviral transduction of miRKIP (F; n=5; ±s.d.). Down-regulation of human RKIP was confirmed by real-time qRT-PCR (G; n=5; ±s.d.)

FIGS. 7A-F: Transgenic RKIP Expression Induces a GRK2 Inhibition-Related Gene Expression Signature A, Immunoblot detection of serine-153 phosphorylation of RKIP (pS153) in Tg-RKIP and B6 control hearts (n=5 mice/group). B, Removal of RKIP by affinity purification (AP) with immobilized RKIP-specific antibodies depletes the GRK2 protein from Tg-RKIP heart lysates. A control affinity purification with unrelated antibodies did neither deplete RKIP nor GRK2. Upper panels show representative experiments and lower panels show quantitative data evaluation (±s.d., n=4; *, p=0.0286; Mann Whitney Test). C, Isoproterenol-stimulated cAMP response in neonatal cardiomyocytes from Tg-RKIP and Tg-GRK2-K220R mice (n=6; ±s.d.). D, Significantly increased expression of the cAMP inducible gene, Ttc14, in Tg-RKIP and Tg-GRK2-K220R hearts relative to the B6 control (n=3; ±s.d.). E, F, Whole genome gene expression profiling revealed concordant regulation of 45% of significantly altered probe sets between Tg-RKIP and Tg-GRK2-K220R hearts. Panel F shows concordantly regulated probe sets in Tg-RKIP and Tg-GRK2-K220R hearts (two gene chips/group; , p<0.01 and *, p<0.001, t-test relative to B6 control).

FIGS. 8A-8F: The Cardio-Protective GRK2 Inhibitor Paroxetine Retards the Heart Failure Phenotype of Tg-RKIP Mice A-C, Treatment with paroxetine (5 mg/kg body weight in drinking water per day) for 8 weeks decreased the cardiac content of Srsf1 and activating Srsf1 phosphorylation (A), and the splicing of Camk2d isoforms B/C (B) in 5 month-old Tg-RKIP hearts as determined in immunoblot (B, n=5 hearts/group) and real-time qRT-PCR (C, n=6; ±s.d). C, Myocardial necrosis with calcium overload was determined on cardiac sections by von Kossa stain (n=6 hearts/group; ±s.d.). D, The left ventricular ejection fraction was determined by echocardiography (n=6 mice/group; ±s.d.). D-F, the development of myocardial necrosis and signs of heart failure were retarded.

Figure 9:
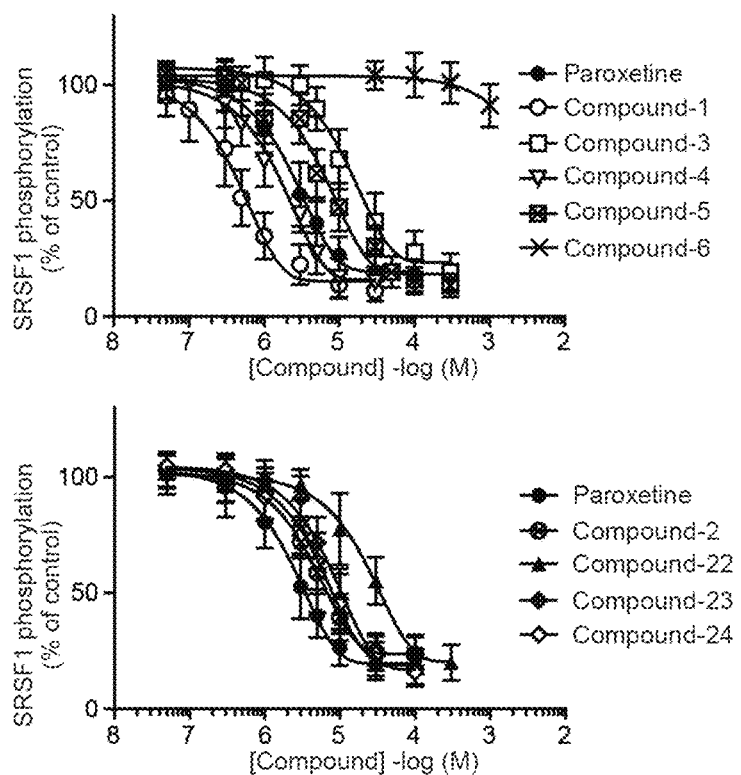
Figure 10:
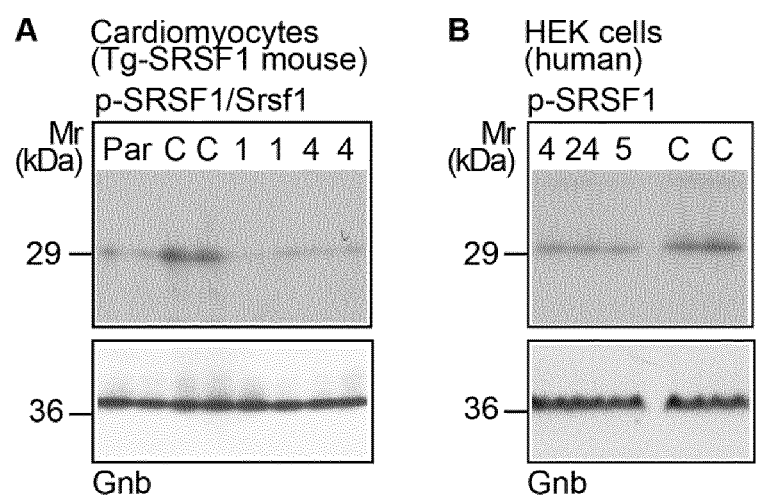

FIG. 9: Development of Small Molecule Compounds, which Inhibit GRK2-Mediated Srsf1 Phosphorylation.

The GRK2-mediated phosphorylation of SRSF1 was determined with purified proteins in the presence of increasing concentrations of paroxetine or different small molecule compounds. SRSF1 phosphorylation is presented as % of control, which is the SRSF1 phosphorylation in the absence of inhibitor. The IC50 value of 0.45 µM of 1-(1,3-benzodioxol-5-yl)-4-(cyclopropane-carbonyl)-3-hydroxy-2-phenyl-2H-pyrrol-5-one ("Compound-1") is more than 5-fold lower than that of paroxetine (±s.d., n=4).

FIGS. 10A-B: Small Molecule Compounds Inhibit the GRK2-Mediated SRSF1 Phosphorylation in Intact Tg-SRSF1 Cardiomyocytes and Human HEK Cells.

A, The GRK2-mediated phosphorylation of SRSF1/Srsf1 was determined by immunoblot in lysates from isolated neonatal cardiomyocytes from Tg-SRSF1 mice after incubation for 60 h with 10 microM of paroxetine, 1-(1,3-benzodioxol-5-yl)-4-(cyclopropane-carbonyl)-3-hydroxy-2-phenyl-2H-pyrrol-5-one ("Compound-1") or 4-(1,3-benzodioxol-5-yl)pyrimidine ("Compound-4") relative to vehicle-treated control ("C") cardiomyocytes. B, Immunoblot detection of GRK2-mediated phosphorylation of SRSF1 (pSRSF1) was performed with lysates from HEK (human embryonic kidney) cells incubated for 60 h with 10 microM of 4-(1,3-benzodioxol-5-yl)pyrimidine ("Compound-4"), 1-(1,3-benzodioxol-5-ylmethyl)-5-(4-chlorophenyl)-2-methyl-pyrrole-3-carboxamide ("Compound-24") or (4R)-N3-(1,3-benzodioxol-5-ylmethyl)-N4-[[3-(trifluoromethyl)phenyl]-methyl]pyrrolidine-3,4-dicarboxamide ("Compound-5") relative to vehicle-treated controls ("C").

FIGS. 11A-B: Cardio-Protective Effects of Small Molecule Compounds In Vivo.

A, The GRK2-mediated phosphorylation of Srsf1 was determined by immunoblot in cardiac lysates prepared from hearts of non-transgenic B6 mice after treatment (i.p.) for 5 h with 10 mg/kg of 1-(1,3-benzodioxol-5-yl)-4-(cyclopropane-carbonyl)-3-hydroxy-2-phenyl-2H-pyrrol-5-one ("Compound-1"), 4-(1,3-benzodioxol-5-yl)pyrimidine ("Compound-4"), 1-(1,3-benzodioxol-5-ylmethyl)-5-(4-fluorophenyl)-2-methyl-pyrrole-3-carboxamide ("Compound-2"), or (4R)-N3-(1,3-benzodioxol-5-ylmethyl)-N4-[[3-(trifluoromethyl)phenyl]-methyl]pyrrolidine-3,4-dicarboxamide ("Compound-5") relative to vehicle-treated B6 controls ("con"). The right panel shows quantitative immunoblot evaluation. B, Left panel: The AAC-induced cardiac p-Srsf1 content was determined in cardiac lysates from B6 mice with AAC after treatment for 7 days with 5 mg/kg/d of 1-(1,3-benzodioxol-5-yl)-4-(cyclopropane-carbonyl)-3-hydroxy-2-phenyl-2H-pyrrol-5-one ("Compound-1") or (4R)-N3-(1,3-benzodioxol-5-ylmethyl)-N4-[[3-(trifluoromethyl)phenyl]-methyl]pyrrolidine-3,4-dicarboxamide ("Compound-5") relative to vehicle-treated B6 controls with AAC ("AAC-con"). The middle panel shows quantitative immunoblot evaluation. Right and lower panels: Cardiac function parameters were determined by echocardiography in B6 mice with AAC after treatment for 7 days with "Compound-1" or "Compound-5" relative to vehicle-treated B6 controls with AAC ((±s.d.; n=5 (A) and n=3 (B); Dunnett's Multiple Comparison Test vs. con (A) or AAC-con (B)).

FIGS. 12A-D: Oral Treatment with Compound-1 and Compound-4 Counteracts Heart Failure and Ageing Induced by Cardiovascular Disease.

A, The left ventricular ejection fraction was determined in 6 month-old male B6 mice with chronic pressure overload imposed by 3 months of AAC and oral treatment with Compound-1 (AAC+compd-1) and Compound-4 (AAC+compd-4) relative to untreated AAC controls. Treatment was started one month after AAC induction and was continued for 2 months. Only mice with heart failure (ejection fraction <34% after one month of AAC) were included in the study (±s.d., n=5/group, *p=0.0006, p=0.0051 vs. untreated AAC; Dunnett's multiple comparison test). B, Histological assessment of hearts with 3 months of AAC without (controls, upper panels) or with 2 months of treatment with Compound-1 (lower panels) reveals that Compound-1 retards the chronic pressure overload-induced cardiac hypertrophy (n=4 hearts/group). C,D, Treatment with Compound-1 also retards cardiovascular disease-induced ageing, e.g. induced by chronic pressure overload, i.e. the grey coloring of the hair was substantially retarded after 2 months of treatment with Compound-1 (left (D) and right (D) panels, n=5 different mice).

FIGS. 13A-J: Identification of Tested Compounds According to the Present Invention Molecule and Exemplary Chemical Synthesis Route A-H, Compounds-1 to -5 and -22 to -24 were analyzed by electrospray mass spectrometry and HPLC analysis. I, J, exemplary chemical synthesis routes of Compound-1 and Compound-4.

EXAMPLE 1: IDENTIFICATION OF SRSF1 AS NOVEL NON-RECEPTOR GRK2 SUBSTRATE

In view of the pathophysiological importance of GRK2 and its yet unknown targets novel GRK2-interacting proteins were searched for. GRK2-specific antibodies were covalently coupled to an affinity matrix. A protein lysate from biopsy specimens from heart failure patients was applied, bound proteins were eluted, and enriched GRK2 and co-enriched proteins were separated by SDS-PAGE. Stained protein bands were cut out and Nano-LC-ESI-MS/MS analysis identified SRSF1 (Serine/arginine-rich splicing factor 1) ASF/SF2) as a previously unrecognized GRK2-interacting protein (FIG. 1A, right panel). As a control, immunoblot detection confirmed the protein enrichment of GRK2 and the co-enrichment of SRSF1 (FIG. 1A, left panels). It was found that SRSF1 is a kinase substrate of GRK2. In an in vitro kinase assay, GRK2 phosphorylated the recombinant SRSF1 protein (FIG. 1B). Nano-LC-ESI-MS/MS analysis identified phospho-containing peptides with serine199/201 as GRK2 phosphorylation site(s) (FIG. 1B). The phosphorylation of SRSF1 on serine 199/201 by GRK2 is of relevance because these residues and phosphorylation of these residues are essentially involved in the splicing function of SRSF1 (Zuo P and Manley J L, EMBO J 12, 4727-4737 (1993); Xiao S H and Manley J L, Genes Dev 11, 334-344 (1997)). As a control for GRK2-specificity of the in vitro phosphorylation assay, the cardio-protective ATP-site-directed GRK2 inhibitor, paroxetine (Thal D M, et al., ACS Chem Biol 7, 1830-1839 (2012); Schumacher S M, et al., Sci. Transl. Med. 7, 277ra31 (2015)) was applied. Paroxetine inhibited the GRK2-mediated phosphorylation of SRSF1 with a half maximum inhibitory concentration (IC50 value) of 2.38 µM (FIG. 1C). This value is comparable to the paroxetine-mediated inhibition of other GRK2 substrates (Thal D M, et al., ACS Chem Biol 7, 1830-1839 (2012); Schumacher S M, et al., Sci. Transl. Med. 7, 277ra31 (2015)). In addition, GRKInh, another cardio-protective GRK2 inhibitor (6,7), also inhibited the in vitro phosphorylation of SRSF1 by GRK2 (FIG. 1D). The activating phosphorylation of SRSF1 by GRK2 was also confirmed in immune-blot with the phospho-specific SR antibody 1H4 (FIG. 1E), which detects phosphorylated RS repeats in the carboxyl terminal domain of SRSF1 (Neugebauer K M, et al., Genes Dev. 11, 1148-1159 (1997)).

EXAMPLE 2: GRK2 INDUCES ACTIVATING SRSF1 PHOSPHORYLATION IN VIVO

It was investigated whether GRK2 phosphorylates Srsf1 in vivo and Tg-GRK2 mice were generated with myocardium-specific human GRK2 (ADRBK1) expression under control of the myocardium-specific alpha-MHC promoter (FIG. 2A). The hearts of Tg-GRK2 mice had an increased GRK2 protein level (2-fold over the non-transgenic B6 control, FIGS. 2B and 2C). In agreement with the pathophysiological role of an increased cardiac GRK2 protein level (Hullmann J, et al., Pharmacol. Res. 110, 52-64 (2016)), Tg-GRK2 mice developed cardiac dysfunction with increased age as documented by a significantly reduced cardiac ejection fraction in 8 month-old Tg-GRK2 mice (FIG. 2D). The cardiac content of activated phospo-Srsf1 was determined to analyze whether the increased GRK2 protein level in transgenic Tg-GRK2 mice resulted in increased Srsf1 phosphorylation and activation. Immunoblot detection revealed that Tg-GRK2 hearts had an increased level of activating Srsf1 phosphorylation (FIG. 2E). The splicing factor activity of activated Srsf1 is required for Camk2d (calcium calmodulin-dependent kinase II isoform 6) isoform B and C splicing (Xu X, et al., Cell 120, 59-72 (2005)). In agreement with the enhanced activation of Srsf1, Tg-GRK2 hearts had an increase in heart-specific Camk2d isoforms B and C as detected in immunoblot (FIG. 2G). An increase in Camk2d isoforms B and C is sufficient to promote cardiac dysfunction and heart failure (Zhang T, et al., Circ. Res. 92, 912-919 (2003); Zhang T, et al., J. Biol. Chem. 277, 1261-1267 (2002)).

Moreover, Camk2d promotes cardiac necrosis (Zhang T, et al., Nat. Med. 22, 175-182 (2016)). Tg-GRK2 hearts showed an increase in necrotic areas with calcium overload as determined with von Kossa stain (FIG. 2H). The causal relationship between GRK2-mediated Srsf1 activation and the cardiac phenotype of Tg-GRK2 hearts was also demonstrated by down-regulation of Srsf1 by lentiviral transduction of an miRNA targeting Srsf1 by RNAi (FIG. 2I). The down-regulation of Srsf1 retarded the induction of Camk2d isoforms B and C, the development of signs of heart failure and cardiac necrosis with calcium overload in Tg-GRK2 hearts (FIG. 2J-2L).

EXAMPLE 3: TRANSGENIC OVEREXPRESSION OF SRSF1 INDUCES ENHANCED CAMK2D SPLICING AND SIGNS OF HEART FAILURE

Tg-SRSF1 mice with increased cardiac SRSF1 protein due to myocardium-specific SRSF1 expression were generated under control of the myocardium-specific alpha-MHC Promoter (FIG. 3A). Tg-SRSF1 mice had an increased cardiac SRSF1 protein (FIG. 3B) and showed enhanced splicing of Camk2d isoforms B and C (FIG. 3C). Concomitantly, Tg-SRSF1 mice developed myocardial necrosis with calcium overload, cardiac hypertrophy with dilation (indicative of cardiomyocyte loss) and cardiac dysfunction (FIG. 3D-F).

EXAMPLE 4: INHIBITION OF GRK2 IN VIVO RETARDS ACTIVATING SRSF1 PHOSPHORYLATION, AND SIGNS OF HEART FAILURE IN A CHRONIC PRESSURE OVERLOAD MODEL OF CARDIAC DYSFUNCTION

Figure 4:
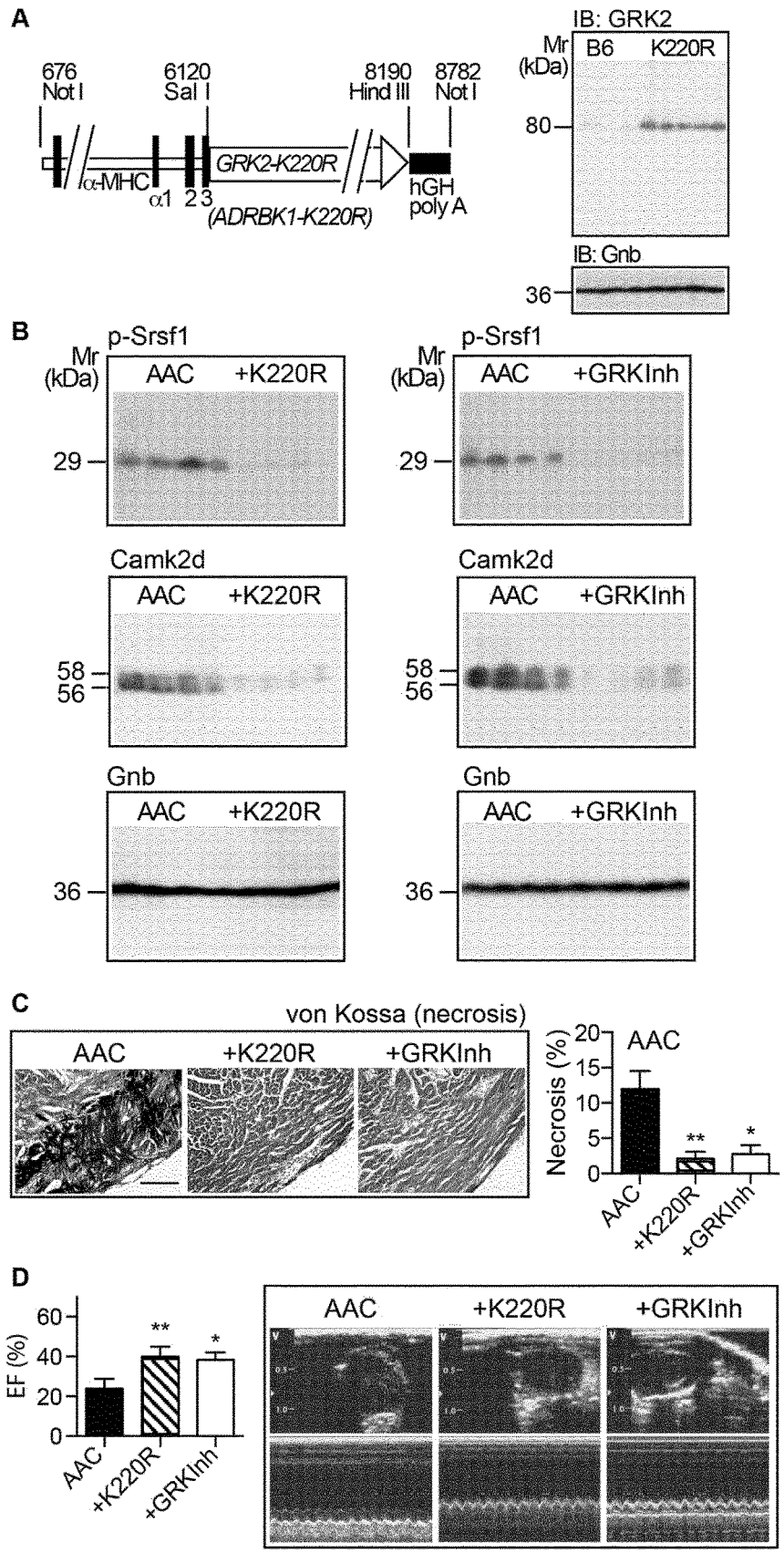

Srsf1 and GRK2 are up-regulated in experimental models of pressure overload-induced cardiac dysfunction (Hullmann J, et al., Pharmacol. Res. 110, 52-64 (2016); Kim T, et al., Mol Cells 37, 81-87 (2014)). The pressure overload-triggered induction of activating Srsf1 phosphorylation was retarded by GRK2 inhibition with transgenic expression of the dominant-negative GRK2-K220R mutant (FIG. 4B). The transgenic Tg-GRK2-K220R mice with myocardium-specific expression of GRK2-K220R were generated (FIG. 4A). The cardio-protective GRK2 inhibitor, GRKInh (Abd Alla, J, et al., J. Biol. Chem. 291, 2583-2600 (2016); Fu X, et al., J. Biol. Chem. 288, 7738-7755 (2013)), which inhibits SRSF1 phosphorylation in vitro (cf. FIG. 1), also retarded the pressure overload-induced activating Srsf1 phosphorylation by GRK2. Concomitantly, the two different modes of GRK2 inhibition retarded Camk2d isoform B/C splicing, myocardial necrosis with calcium overload and signs of heart failure (FIG. 4C,D). Thus, cardio-protective GRK2 inhibition blunts pressure overload-induced Srsf1 activation, cardiomyocyte death and signs of heart failure.

EXAMPLE 5: THE GRK2 INHIBITOR RKIP DOES NOT INHIBIT ACTIVATING SRSF1 PHOSPHORYLATION AND INDUCES SIGNS OF HEART FAILURE IN VIVO

Figure 5:
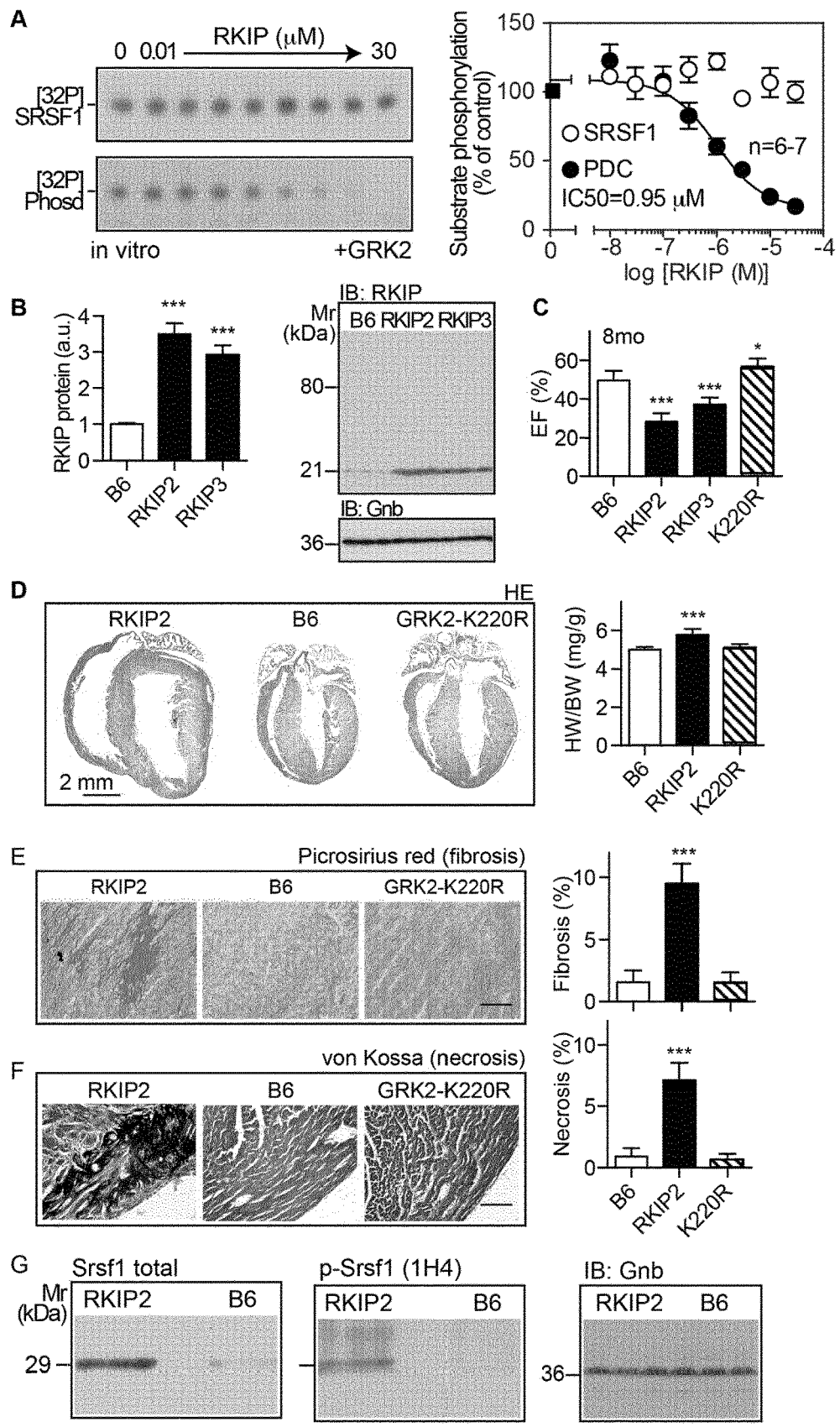
Figure 6:
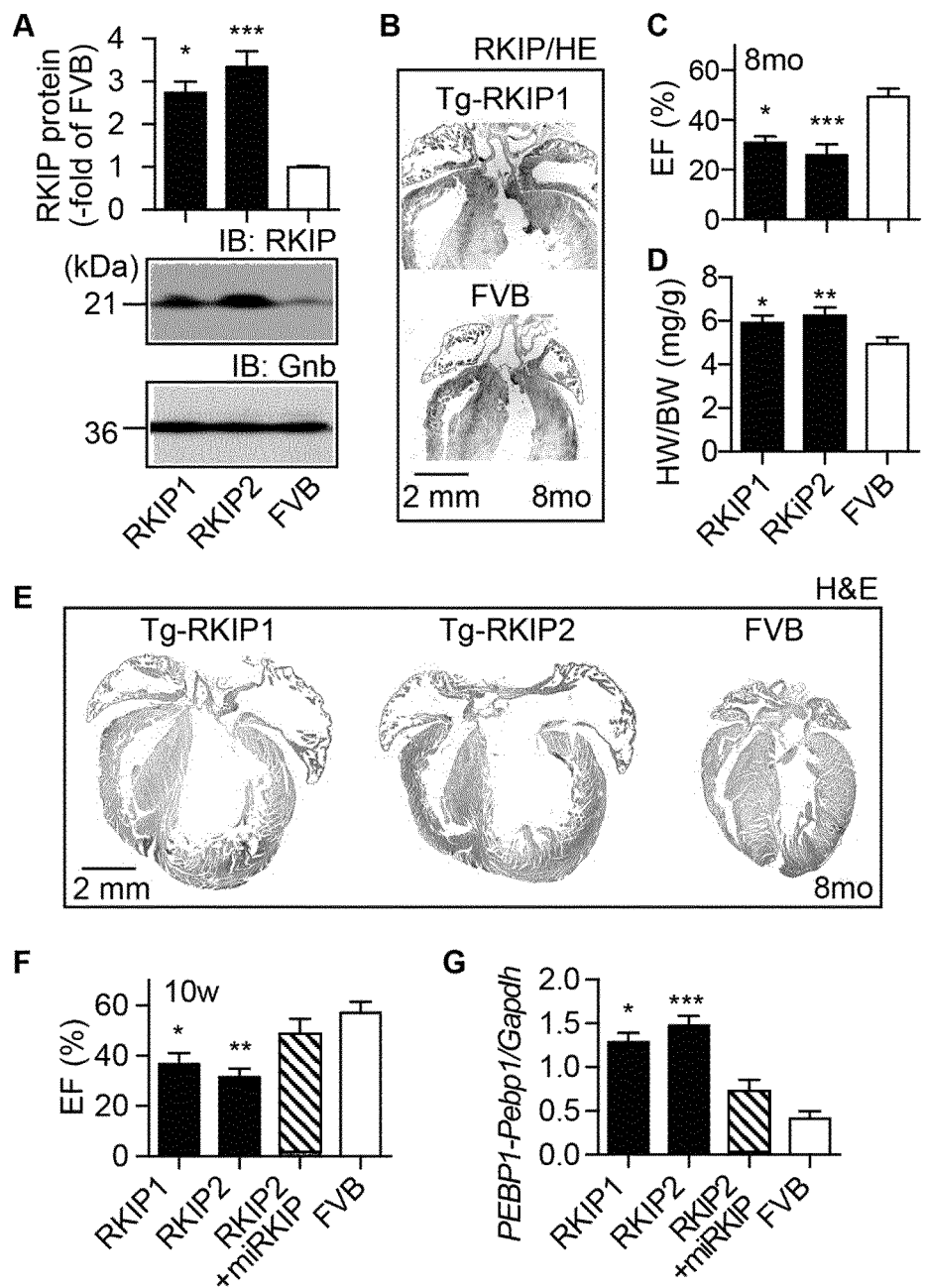

The role of another GRK2 inhibitor, i.e. the raf kinase inhibitor protein, RKIP (Lorenz K, et al., Nature 426, 574-579 (2003)) was analyzed, which is a dual-specific GRK2 and Raf kinase inhibitor. RKIP shows up-regulation in cardiac biopsy specimens of patients with heart failure (Schmid E, et al., Nat. Med. 21, 1298-1306 (2015)). Human RKIP did not inhibit the phosphorylation of SRSF1 by GRK2 in vitro (FIG. 5A). As a control, human RKIP is an efficient GRK2 inhibitor and inhibited the phosphorylation of phosducin (FIG. 5A), which is another non-receptor substrate of GRK2 (Ruiz-Gomez A, et al., J. Biol. Chem. 275, 29724-29730 (2000)). The IC50 value for human RKIP-mediated inhibition of GRK2-induced phosducin phosphorylation was 950 nM (FIG. 5A), which is comparable to the reported IC50 value of 460 nM for RKIP-mediated inhibition of GPCR phosphorylation (Lorenz K, et al., Nature 426, 574-579 (2003)). Tg-RKIP mice with myocar-dium-specific expression of human RKIP developed signs of heart failure in a dose-dependent manner (FIG. 5B,C). Concomitantly, cardiac hypertrophy with dilation, cardiac fibrosis and necrosis were evident (FIG. 5D-F). In agreement with the in vitro experiments, which documented the inability of human RKIP to inhibit activating SRSF1 phosphorylation by GRK2 (cf. FIG. 5A), the cardiac content of activating Srsf1 phosphorylation was higher in Tg-RKIP hearts than that in non-transgenic B6 controls (FIG. 5G).

EXAMPLE 6: TG-RKIP MOUSE LINES IN THE FVB BACKGROUND ALSO DEVELOP SIGNS OF HEART FAILURE

The heart failure phenotype induced by transgenic human RKIP expression was similarly detected in a dose-dependent manner in human RKIP-expressing transgenic mouse lines generated in the FVB background (FIG. 6A-D). Histology analysis revealed that Tg-RKIP mice in the FVB background developed a strong cardiac hypertrophy with dilation and cardiomyocyte loss (FIG. 6E). The cardiac dysfunction of Tg-RKIP mice was partially reversed by down-regulation of transgenic RKIP (PEBP1) by lentiviral transduction of an miRNA targeting RKIP (PEBP1) by RNAi (FIG. 6F,G). Thus, the heart failure phenotype in Tg-RKIP mice was attributed to transgenic RKIP expression.

EXAMPLE 7: TRANSGENIC RKIP INTERACTS WITH GRK2 AND INDUCES A GRK2 INHIBITION-RELATED GENE EXPRESSION SIGNATURE

The GRK2-inhibitory activity of transgenic RKIP (human RKIP~PEBP1) was controlled in vivo. The phosphorylation of RKIP on serine-153 switches RKIP from Raf1 inhibition to GRK2 inhibition (Lorenz K, et al., Nature 426, 574-579 (2003)). Substantial serine-153 phosphorylation of RKIP was documented by immunoblot detection in Tg-RKIP hearts (FIG. 7A). The serine-153 phosphorylated RKIP was sufficient to bind and neutralize 90.4% (±3.6%, n=4) of the GRK2 protein in Tg-RKIP hearts (FIG. 7B). We determined the GRK2 inhibition-mediated resensitization of the isoproterenol-stimulated cAMP response in neonatal cardiomyocytes as readout for GRK2 inhibition by RKIP and GRK2-K220R, respectively (Abd Alla, J, et al., J. Biol. Chem. 291, 2583-2600 (2016); Kong K C, et al., Biochemistry 47, 9279-9288 (2008)). Neonatal cardiomyocytes from Tg-RKIP and Tg-GRK2-K220R mice showed comparable signs of GRK2 inhibition as documented by the significantly enhanced β-adrenoceptor-mediated cAMP response (FIG. 7C). Resensitized cAMP signaling was confirmed in vivo by the significantly increased expression of the cAMP inducible gene, Ttc14, in Tg-RKIP and Tg-GRK2-K220R hearts (FIG. 7D). Whole genome microarray gene expression profiling further revealed a GRK2 inhibition-related gene expression signature in Tg-RKIP hearts (FIGS. 7E,F). Notably, there was concordant regulation of 45% of significantly altered probe sets between Tg-RKIP and Tg-GRK2-K220R hearts (FIGS. 7E,F).

EXAMPLE 8: THE CARDIO-PROTECTIVE GRK2 INHIBITOR PAROXETINE RETARDS THE HEART FAILURE PHENOTYPE IN TG-RKIP MICE

It was analyzed, whether the incapability of RKIP to inhibit the activating Srsf1 phosphorylation by GRK2 contributed to the heart failure phenotype in Tg-RKIP mice. Tg-RKIP mice were treated with the GRK2 inhibitor, paroxetine, which is cardio-protective in an experimental model of myocardial infarction (Schumacher S M, et al., Sci. Transl. Med. 7, 277ra31 (2015)). Paroxetine also inhibits SRSF1 phosphorylation in vitro (cf. FIG. 1C). Treatment with paroxetine for 8 weeks decreased the cardiac content of activating Srsf1 phosphorylation and the splicing of Camk2d isoforms B/C in Tg-RKIP hearts (FIG. 8A-C). Concomitantly, the development of myocardial necrosis and signs of heart failure were retarded (FIG. 8D-F). Taken together, data with transgenic mice and different GRK2 inhibitors show that cardio-protective GRK2 inhibition relies on inhibition of the activating Srsf1 phosphorylation by GRK2.

EXAMPLE 9: DEVELOPMENT OF SMALL MOLECULE COMPOUNDS, WHICH INHIBIT GRK2-MEDIATED SRSF1 PHOSPHORYLATION

Small molecule compounds were developed, which inhibit GRK2-mediated SRSF1 phosphorylation (FIG. 9). 1-(1,3-benzodioxol-5-yl)-4-(cyclopropane-carbonyl)-3-hydroxy-2-phenyl-2H-pyrrol-5-one ("Compound-1") inhibits the GRK2-mediated SRSF1 phosphorylation with an IC50 value of 0.45 microM. The IC50 value of 1-(1,3-benzodioxol-5-yl)-4-(cyclopropane-carbonyl)-3-hydroxy-2-phenyl-2H-pyrrol-5-one ("Compound-1") is more than 5-fold lower than that of paroxetine (FIG. 9), which is the only available small molecule GRK2 inhibitor with documented cardio-protective activity under experimental conditions in vivo (Schumacher S M, et al., Sci. Transl. Med. 7, 277ra31 (2015)). The four compounds 1-(1,3-benzodioxol-5-ylmethyl)-5-(4-fluorophenyl)-2-methyl-pyrrol-3-carboxamide, (3R)—N-(1,3-benzodioxol-5-ylmethyl)-5-(4-fluorophenyl) thiomorpholine-3-carboxamide, 4-(1,3-benzodioxol-5-yl) pyrimidine, and (4R)-N3-(1,3-benzodioxol-5-ylmethyl)-N4-[[3-(trifluoromethyl)phenyl]-methyl]pyrrolidine-3,4-dicarboxamide ("Compounds 2-5") inhibited the SRSF1 phosphorylation with IC50 values ranging between 1.87 microM (4-(1,3-benzodioxol-5-yl)pyrimidine, "Compound-4") and 12.87 microM ((3R)—N-(1,3-benzodioxol-5-ylmethyl)-5-(4-fluorophenyl)thiomorpholine-3-carboxamide, "Compound-3") (FIG. 9). An unrelated control compound, Ibuprofen ((±)-2-(4-Isobutylphenyl)propanoic acid ("Compound-6", Sigma-Aldrich, St. Louis, USA) had no inhibitory effect up to 1 mM (FIG. 9).

EXAMPLE 10: SMALL MOLECULE COMPOUNDS INHIBIT THE GRK2-MEDIATED SRSF1/SRSF1 PHOSPHORYLATION IN INTACT CARDIOMYOCYTES AND HUMAN KIDNEY CELLS 1-(1,3-benzodioxol-5-yl)-4-(cyclopropane-carbonyl)-3-hydroxy-2-phenyl-2H-pyrrol-5-one ("Compound-1") and 4-(1,3-benzodioxol-5-yl)pyrimidine ("Compound-4") also decreased the heart failure-promoting SRSF1/Srsf1 phosphorylation in isolated Tg-SRSF1 cardiomyocytes (FIG. 10A). GRK2 inhibition promotes survival of human kidney cells (Fu X, et al., J. Biol. Chem. 288, 7738-7755 (2013)). 4-(1,3-benzodioxol-5-yl)pyrimidine ("Compound-4"), 1-(1, 3-benzodioxol-5-ylmethyl)-5-(4-chlorophenyl)-2-methyl-pyrrole-3-carboxamide ("Compound-24") and (4R)-N3-(1, 3-benzodioxol-5-ylmethyl)-N4-[[3-(trifluoromethyl) phenyl]-methyl]pyrrolidine-3,4-dicarboxamide ("Compound-5") inhibited the cell-damaging SRSF1 phosphorylation in human kidney cells (FIG. 10B).

EXAMPLE 11: CARDIO-PROTECTIVE EFFECTS OF SMALL MOLECULE COMPOUNDS IN VIVO

Short-term treatment for 5 h with small molecule compounds (1-((1,3-benzodioxol-5-yl)-4-(cyclopropane-carbonyl)-3-hydroxy-2-phenyl-2H-pyrrol-5-one ("Compound-1"), 4-(1,3-benzo-dioxol-5-yl)pyrimidine ("Compound-4"), 1-(1,3-benzodioxol-5-ylmethyl)-5-(4-fluorophenyl)-2-methyl-pyrrol-3-carboxamide ("Compound-2") and (4R)-N3-(1,3-benzodioxol-5-ylmethyl)-N4-[[3-(trifluoromethyl) phenyl]methyl]pyrrolidine-3,4-dicarboxamide ("Compound-5") decreased the heart failure promoting GRK2-mediated Srsf1 phosphorylation under basal conditions in vivo, in the hearts of non-transgenic B6 mice (FIG. 11A). Treatment with "Compound-1" or "Compound-5" also retarded the chronic pressure overload-induced cardiac p-Srsf1 content and improved the cardiac performance of B6 mice after chronic pressure overload imposed by AAC (FIG. 11B).

EXAMPLE 12: ORAL TREATMENT WITH COMPOUND-1 AND COMPOUND-4 COUNTERACTS HEART FAILURE AND AGEING INDUCED BY CARDIOVASCULAR DISEASE

We investigated whether the new small molecule GRK2 inhibitors, Compound-1 (1-(1,3-benzodioxol-5-yl)-4-(cyclopropanecarbonyl)-3-hydroxy-2-phenyl-2H-pyrrol-5-one)) and Compound-4 (4-(1,3-benzodioxol-5-yl)pyrimidine) could retard symptoms of heart failure in a chronic pressure overload model of heart failure imposed by abdominal aortic constriction (AAC). Compound-1 (3 mg/kg/d) and Compound-4 (5 mg/kg/d) were applied orally in the AAC-induced model of heart failure. Oral treatment with Compound-1 and Compound-4 was initiated in B6 mice with symptoms of heart failure (left ventricular ejection fraction <34%) induced by four weeks of AAC. Two months of treatment with Compound-1 and Compound-4, respectively, counteracted the AAC-induced cardiac dysfunction as documented by a significantly improved left ventricular ejection fraction of 41.4±4.8% and 38.2±3.7% after treatment with Compound-1 and Compound-4, respectively, compared to the ejection fraction of the untreated AAC controls of 28.6%±3.5% (FIG. 12A). In addition to the improved cardiac function, histological analysis showed a decrease in the AAC-induced cardiac hypertrophy after oral treatment with Compound-1 (FIG. 12B). Concomitantly, as a consequence of the improved cardiac function, cardiovascular disease-induced ageing of the mice was visibly retarded, i.e. the grey coloring of the black hair was substantially retarded after 8 weeks of treatment with Compound-1 compared to untreated B6 control animals (FIG. 12C, D).

EXAMPLE 13: MATERIAL AND METHODS

Generation of Transgenic Mice

The study used the following transgenic mouse lines, which were generated by our group: Tg-RKIP (PEBP1) mice in the B6 (C57BL/6J) and FVB background, Tg-GRK2 (ADRBK1) mice in the B6 background, Tg-SRSF1 mice in the B6 background, Tg-GRK2-K220R and Tg-GRKInh mice in the B6 background. All the transgenes were expressed under control of the myocardium-specific alpha-MHC promoter (the MyHC plasmid was kindly provided by James Gulick, Gulick J, et al., J. Biol. Chem. 266, 9180-9185 (1991)). Transgenic mice were generated according to standard procedures. Briefly, the DNAs encoding the indicated proteins/peptides were inserted into the alpha-MHC (MyHC) plasmid, plasmid sequences were removed by Not I digestion and the purified DNA (2 ng/microL) was injected into fertilized oocytes of superovulated B6 (C57BL/6J) and FVB (FVB/N) mice. Oviduct transfer of injected embryos into pseudopregnant CD-1 mice was performed according to standard procedures. Genomic DNA of the F0 generation was isolated from ear punch biopsies taken at an age of 3-4 weeks and analyzed by PCR for integration of the transgene (Fu X, et al., J. Biol. Chem. 288, 7738-7755 (2013)).

Chronic Pressure Overload-Induced Model of Experimental Heart Failure and Transthoracic Echocardiography Chronic pressure overload imposed by abdominal aortic constriction (AAC) was used as an experimental model to induce cardiac hypertrophy and signs of heart failure. Aortic constriction of the abdominal aorta was performed in tribromoethanol-anesthetized 8-12 week-old transgenic mice or non-transgenic B6 controls as described (AbdAlla S, et al., Cardiovasc. Hematological Agents Med. Chem. 9, 190-206 (2011)). The abdominal aorta was constricted above the suprarenal artery by tying a 7-0 silk suture ligature against a blunt 26-gauge needle. Age-matched controls underwent identical surgical procedure except for ligation of the aorta (sham-operated mice).

Cardiac function parameters were determined by transthoracic echocardiography, which was performed on anesthetized mice with a Vivid 7 echocardiograph equipment (GE Healthcare, Glattbrugg, Schweiz) and a 12 MHz linear array transducer. The left ventricular ejection fraction was calculated in the M-mode of the parasternal long-axis view using the formula of Teichholz. M-mode imaging was performed according to the recommendations of the American Society of Cardiology (Sahn D J, et al., Circulation 58, 1072-1083 (1978)) adapted to mice. Recordings were interpreted offline using EchoPac Pc 3.0 software (GE Healthcare, Glattbrugg, Schweiz).

Animal experiments were performed in accordance with the NIH guidelines, and reviewed and approved by the local committee on animal care and use (University of Zurich).

Nano-LC-ESI-MS/MS

To enrich proteins interacting with human heart GRK2 protein, a protein lysate was prepared from small myocardial biopsy specimens from patients with signs of heart failure undergoing mitral valve replacement. Informed consent was obtained from all participants. The study was conducted in conformity with the principles of the declaration of Helsinki, with approval of the protocol by the ethical committee of Ain Shams University. Patient characterization of study participants was published previously (AbdAlla S, et al., Cardiovasc. Hematological Agents Med. Chem. 9, 190-206 (2011)). The enrichment of GRK2 and co-enrichment of GRK2-interacting proteins was performed similarly as described (Fu X, et al., J. Biol. Chem. 288, 7738-7755 (2013)). Briefly, myocardial proteins were solubilized for 30 min at 4° C. with solubilization buffer (1% sodium deoxycholate, 0.05% SDS, 0.05% Tween 20 in PBS, pH 7.4 supplemented with protease inhibitors), insoluble material was removed by centrifugation, the supernatant was diluted 1:5 in PBS supplemented with protease inhibitors and subjected to affinity chromatography with anti-GRK2 antibodies (6 mg of affinity-purified IgG coupled to 1 ml of Affigel 10, Bio-Rad Gmbh, München, Germany; polyclonal anti-GRK2 antibodies were raised in rabbit against full-length recombinant GRK2 protein expressed in Sf9 insect cells). After overnight incubation at 4° C., unbound proteins were removed by washing with PBS (20 column volumes), and bound proteins were eluted with 0.25 M NH$_4$OH, 10% dioxane, pH 11. The pH of the eluate was immediately adjusted to pH 7.4, eluted proteins were concentrated by acetone precipitation, dissolved in 8 M urea, and subjected to 8% urea-containing SDS-PAGE under reducing conditions. After Coomassie Brilliant Blue staining, enriched protein bands were cut and subjected to nano-LC-ESI-MS/MS. The SRSF1 protein was identified in the gel slice encompassing the 30-40 kDa protein range. Protein identification was performed by nano-LC-ES-MS/MS (Proteome Factory AG, Berlin). The MS system consisted of an Agilent 1100 nano-LC system (Agilent, Boeblingen, Germany), a PicoTip emitter (New Objective, Woburn, Mass.) and an Esquire 3000 plus ion trap MS (Bruker, Bremen, Germany). The cut protein band was in-gel digested by trypsin (Promega, Mannheim, Germany) and applied to non-LC-MS/MS. After trapping and desalting the peptides on an enrichment column (Zorbax SB C18, 0.3×5 mm, Agilent Boeblingen, Germany) using 1% acetonitrile, 0.5% formic acid solution for 5 min, peptides were separated on a Zorbax 300 SB C18, 75 microm×150 mm column (Agilent Boeblingen, Germany) using an acetonitrile, 0.1% formic acid gradient from 5% to 40% acetonitrile within 40 min. MS spectra were automatically taken by Esquire 3000 plus according to the manufacturer's instrument settings for nan-LC-MS/MS analyses. Proteins were identified using MS/MS ion search of the Mascot search engine (Matrix Science, London, England) and nr protein database (National Center for Biotechnology Information, Bethesda, Md.). Ion charge in search parameters for ions form ESI-MS/MS data acquisition were set to "1+, 2+ or 3+" according to the common charge state distribution for the instrument and the method (Fu X, et al., J. Biol. Chem. 288, 7738-7755 (2013)).

For identification of residues in SRSF1, which were phosphorylated by GRK2, the nano-LC-ES-MS/MS analysis was performed with purified recombinant SRSF1 after the in vitro phosphorylation assay. The procedure was performed as detailed above but the MS system consisted of an Agilent 1100 nanoLC system (AGILENT®, Waldbronn, Germany), a Nanomate 100 electrospray system (AD-VION®, Ithaca, USA) and a Finnigan LTQ-FT mass spectrometer (THERMO FISHER®, Bremen, Germany). Settings of the Mascot search engine were adjusted to identify variable modifications, i.e. deamidated (NQ), Oxidation (M), Phospho (ST) and Phospho (Y).

Expression and Purification of Recombinant Proteins.

Recombinant human GRK2 protein and GRK2-S670A protein was expressed in and purified from *Spodoptera frugiperda* (Sf9) cells by the baculoviral expression system. The cDNAs encoding hexahistidine-tagged human GRK2 (ADRBK1) GRK2-S670A were subcloned into the pFast-Bac1 expression plasmid (INVITROGEN™, THERMO FISHER SCIENTIFIC®, Waltham, Mass., USA) using the Sal I/Hind III restriction sites, recombinant baculovirus was generated by the Bac-To-Bac Baculovirus expression system (THERMO FISHER SCIENTIFIC®, Waltham, Mass., USA). Sf9 cells were infected with recombinant baculoviruses at an MOI of 2-3, 48 h after infection cells were harvested by centrifugation, lysed with lysis buffer (300 mM NaCl, 50 mM HEPES, pH 7.5 supplemented with 1% NP40, 1 mM PMSF and protease inhibitor cocktail) and applied to Ni-NTA chromatography. After overnight incubation at 4° C., unbound proteins were removed by washing with lysis buffer (20× column volumes) followed by 1× column volume of 30 mM imidazole-containing lysis buffer. Bound GRK2 was eluted by 300 mM imidazole in lysis buffer, desalted by PD10 column chromatograpy, supplemented with 20% glycerol and stored at −80° C. for further use.

The cDNAs encoding human His6-SRSF1 and phosducin-His6, and the carboxyl terminal domain of GRK2 (SEQ ID NO: 10, His-6 tagged) respectively, were subcloned into the PET-3d expression plasmid (NOVAGEN®, EMD MIL- LIPORE®, Merck KGaA, Darmstadt, Germany) under control of the T7 promoter, which allows protein expression by T7 RNA polymerase induction with IPTG in BL21(DE3) pLysS bacteria. Protein-expressing bacteria were collected by centrifugation, frozen in liquid nitrogen and thawed on ice in lysis buffer (8 M urea, 300 mM NaCl, 50 mM HEPES, 10 mM imidazole, pH 7.5), which was supplemented with 2-mercaptoethanol (0.7 ml/L) freshly before use (10 ml of lysis buffer for a bacterial pellet from 200 ml of culture medium). The bacterial lysate was incubated for 1 h at room temperature, sonicated and centrifuged for 15 min at 4000×g at 4° C. The supernatant was applied to the Ni-NTA column matrix prewashed with 20 ml of lysis buffer. After overnight incubation at 4° C., the flow-through was discarded, the Ni-NTA affinity matrix was subjected to 3 different washing steps (30 min of incubation at 4° C. with 20 ml of each washing buffer for 1 ml of 5% Ni-NTA matrix) with wash buffer-1 (4 M urea, 300 mM NaCl, 50 mM HEPES, 20 mM imidazole, pH 7.5, supplemented freshly with 0.7 ml/I 2-mercaptoethanol), wash buffer-2 (2 M urea, 300 mM NaCl, 50 mM Hepes, 20 mM imidazole, pH 7.5, supplemented freshly with 0.7 ml/L 2-mercaptoethanol) and wash buffer-3 (300 mM NaCl, 50 mM HEPES, 20 mM imidazole, pH 7.5, supplemented freshly with 0.7 ml/I 2-mercaptoethanol). Finally, proteins were eluted with elution buffer (300 mM NaCl, 50 mM HEPES, 500 mM imidazole, pH 7.5, supplemented freshly with 0.7 ml/L 2-mercaptoethanol). Buffer of eluted proteins was exchanged to 150 mM NaCl, 50 mM HEPES (pH 7.5) by PD10 column chromatography.

In Vitro Phosphorylation Assay

Recombinant proteins were used for an in vitro phosphorylation assay with GRK2 and GRK2-S670A. GRK2 and GRK2-5670A were expressed in and purified from *Spodoptera frugiperda* (Sf9) cells by the baculoviral expression system. Substrate phosphorylation was performed in reaction buffer (50 microL of 20 mM Tris, 2 mM EDTA, 5 mM MgCl2 pH 7.5; or 20 mM Hepes, 2 mM MgCl2, 0.025% DDM (n-Dodecyl beta-D-maltoside), pH 7.4) supplemented with 50 microM or 5 microM of ATP, respectively, and [gamma-32P]-ATP, 1×10 6 DPM, specific activity 3000 Ci/mmol)) with 300-500 nM of substrate (SRSF1, phosducin) in the presence of increasing concentrations of GRK2 inhibitor as indicated. The reaction was started by the addition of GRK2-5670A or GRK2 (50 nM or 130 nM). After an incubation for 30 min at 30° C., the reaction was stopped by the addition of 5×SDS-Laemmli buffer. Proteins were separated by SDS-PAGE and subjected to autoradiography. For the analysis of small molecule inhibitors, the phosphorylation assay was performed in reaction buffer (20 mM Tris, 2 mM EDTA, 5 mM MgCl2, 0.05% BSA, pH 7.5; or 20 mM Hepes, 2 mM MgCl2, 0.025% DDM (n-Dodecyl beta-D-maltoside), pH 7.4) supplemented with 5 microM ATP, [gamma-32P]-ATP (1×10 6 DPM, specific activity 3000 $C_1$/mmol)) and 300-500 nM of substrate (SRSF1, phosducin) (=reaction mixture). The reaction mixture was added to GRK2-S670A or GRK2 (50 nM or 60 nM in reaction buffer, without or with increasing concentrations of the small molecule compound) to give a final reaction volume of 50 microL. After an incubation for 30-60 min at 30° C., the phosphorylation was stopped by the addition of 5 volumes of ice-cold reaction buffer. The reaction mixtures were immediately applied to glass fiber filters (GF/C, WHATMAN™, GE Healthcare Life Sciences, Glattbrugg, Switzerland). After three washing steps with 5 ml of reaction buffer, filter-bound radioactivity was determined in a β-counter.

Immunoblot Detection of Proteins

For immunoblot detection of proteins, cardiac tissue was pulverized in liquid nitrogen and extracted with RIPA buffer supplemented with protease/phosphatase inhibitor cocktail, as previously described (Fu X, et al., J. Biol. Chem. 288, 7738-7755 (2013)) with minor modifications. Particulate material was removed by centrifugation at 20,000×g for 15 min at 4° C. Solubilized proteins were precipitated and delipidated by acetone/methanol (12:2; final concentration 83%) for 90 min at 4° C. The precipitate was collected by centrifugation (5000×g, 10 min, 4° C.), which was followed by three washing steps with 0.2 ml of cold acetone. The pellet was dissolved in SDS-sample buffer containing 2% SDS, 0.1 M DTT, and 6 M urea for 90 min at room temperature. After the addition of iodoacetamide (10 mM), samples were stored for further use at −70° C. Detection of proteins was performed with affinity-purified antibodies or F(ab)2 fragments of the respective antibodies after separation of proteins by SDS-PAGE (10% gel for proteins <100 kDa; 7.5% gel for proteins >100 kDa) and subsequent electrophoretic protein transfer to PVDF membranes by semidry blotting (TRANS-BLOT® SD Semi-Dry Transfer Cell, Bio-Rad GmbH, Munchen, Germany). For the electrophoretic transfer of the Fasn protein, a tank transfer cell (Mini TRANS-BLOT® cell, BIO-RAD® GmbH, Munchen, Germany) was used. Bound antibody was visualised with F(ab)2 fragments of enzyme-coupled secondary antibodies (Dianova GmbH, Hamburg, Germany), or by enzyme-coupled protein A (Calbiochem, EMD MILLIPORE®, Merck KGaA, Darmstadt, Germany) as applicable, and was followed by enhanced chemiluminescent detection (ECL Prime, AMERSHAM®, GE Healthcare Life Sciences, Glattbrugg, Switzerland).

Antibodies

The following antibodies were used for immunoblot detection of proteins: anti-Gnb antibodies were raised in rabbit against purified Gnb (Abd Alla, J, et al., J. Biol. Chem. 291, 2583-2600 (2016)); anti-GRK2 antibodies were raised in rabbit against recombinant GRK2 expressed in Sf9 cells (Abd Alla, J, et al., J. Biol. Chem. 291, 2583-2600 (2016)); anti-pRKIP antibodies were raised in rabbit against a short amino acid sequence from human RKIP containing phosphorylated serine-153 (sc-32623, Santa Cruz Biotechnology Inc., Dallas, Tex., USA); anti SRSF1 antibody is a mouse monoclonal antibody epitope mapping near the N-terminus of the SF2/ASF protein (sc-33652, Santa Cruz Biotechnology Inc. USA); SR (1H4) antibody is a mouse monoclonal antibody raised against full length SR of *Xenopus* origin (sc-13509 from Santa Cruz Biotechnology Inc. USA); anti-CAMK2D polyclonal antibodies were raised in rabbit against full-length human protein (purified polyclonal antibody, no. H00000817-D01P; Abnova, Taipei, Taiwan) and monoclonal anti-CAMK2D antibody, which was produced in mouse against CAMK2D (amino acids 301-410) partial recombinant protein with GST-tag (WH0000817M2; Sigma-Aldrich, St. Louis, Mo., USA) were used for detection of CAMK2D/Camk2d isoforms B/C.

Compound Synthesis.

Chemicals were synthesized by EMC microcollections GmbH, Tubingen, Germany and CHIROBLOCK® GmbH, Wolfen, Germany. The synthesis of compounds was performed in a small scale by solid phase chemical synthesis methods, which were adapted from established protocols (For "Compound-1": Poncet J, et al., J. Chem. Soc. Perkin Trans I., 611-616 (1990); for "Compound-2", "Compound-22", "Compound-23", and "Compound-24": Trautwein A W, et al., Bioorg. Med. Chem. Lett. 8, 2381-2384 (1998); for Compound-3: Sakai K, et al., Chem. Pharm. Bull. 29(6)

1554-1560 (1981); for "Compound-4": Coombs T C, et al., Bioorg. Med. Chem. Lett. 23, 3654-3661 (2013); and for "Compound-5": Baber J C, et al., Bioorg. Med. Chem. 20, 3565-3574 (2012)). In addition, Compound-1 and Compound-4 were synthesized in a larger scale as detailed below.

Synthesis of Compound-1

Synthesis of Compound-1 (1-(1,3-Benzodioxol-5-yl)-4-(cyclopropanecarbonyl)-3-hydroxy-2-phenyl-2H-pyrrol-5-one) was performed by a 6-step chemical reaction process (CHIROBLOCK® GmbH, Wolfen, Germany). Step-1 encompassed the synthesis of methyl 2-(1,3-benzodioxol-5-ylamino)-2-phenyl-acetate. A mixture of methyl 2-oxo-2-phenyl-acetate (96 g, 584 mmol, 4.0 equivalents), 1,3-benzodioxol-5-amine (20 g, 146 mmol, 1.0 equivalents), and $Na_2SO_4$ in cyclohexane (800 ml) was refluxed under $N_2$ for 21 h. 5% Pd/C (7.8 g) was added, and the obtained suspension was hydrogenated at 20 bar and 20° C. for 48 h. The resulting heteroge-neous mixture was diluted with EtOAc (ca. 800 ml) and filtered through Celite. The filtrate was concentrated in vacuo (40° C., 100 mbar) to yield a brown oil (135 g) that was purified by flash chromatography (silica gel, ethyl acetate—petroleum ether 12:88 to 30:70) to yield target 3, which was an off-white solid (18.46 g; purity 95%, yield 44%).

Step-2 was the synthesis of S-tert-butyl ethanethioate. A solution of pyridine (87.0 g, 1.1 mol, 1.1 equivalents) in chloroform (800 ml) was cooled in an ice bath and treated with acetyl chloride (86.4 g, 1.1. mol, 1.1 equivalents), with the reaction temperature not exceeding 11° C. To the resulting orange suspension, 2-methylpropane-2-thiol (90.2 g, 1.0 mol, 1.0 equivalents) was dropwise added over 40 min., and the mixture was stirred for 48 h and subsequently quenched with water (500 ml). The phases were separated and the aqueous phase was extracted with chloroform (400 ml). The combined organic extracts were washed with 400 ml each of water, 10% H2SO4, sat. NaHCO3, and water being subsequently dried over $Na_2SO_4$. The obtained chloroformic solution was subjected to fractional distillation, which afforded target S-tert-butyl ethanethioate as a clear liquid (55.8 g, purity 95%, yield 45%).

In Step-3 the synthesis of S-(2-pyridyl) cyclopropanecarbothioate was performed. Cyclopropanecarbonyl chloride (23.5 g, 225 mmol, 1.0 equiv.) was dropwise added to solution of pyridine-2-thiol (25.0 g, 225 mmol, 1.0 equiv.) in THF (250 ml) at 20° C. The mixture was stirred for 10 min, filtered, and the filter cake was washed with 1:4 $Et_2O$/petrol ether (250 ml). The thus obtained solid was dissolved in water (250 ml) and treated with NaHCO3 (19 g, 225 mmol, 1.0 equiv.), and the aqueous solution was extracted with 2*250 ml EtOAc. The combined organic fractions were dried over $Na_2SO_4$ and concentrated in vacuo to afford S-(2-pyridyl) cyclopropanecarbothioate as a yellow oil (37 g, purity 95%; yield 92%).

Step-4 was the synthesis of S-tert-butyl 3-cyclopropyl-3-oxo-propanethioate. A 2-L 3-neck round-bottom flask was charged with HMDS (83.3 g, 516 mmol, 2.5 equiv) and freshly distilled THF (800 ml). The obtained mixture was cooled in an acetone/dry ice bath, and 1.6 M nBuLi in hexanes (323 ml, 516 mmol, 2.5 equiv.) was dropwise added while keeping the temperature below −50° C. Subsequently, the obtained mixture was sequentially treated with solutions of S-(2-pyridyl) cyclopropanecarbothioate (37.0 g, 206 mmol, 1.0 equiv.) and S-tert-butyl ethanethioate (23.4 g, 214 mmol, 1.04 equiv.). The obtained solution was stirred for 1 h at −30° C., and the reaction was quenched (under TLC process control) by 1 N $H_2SO_4$ (800 ml). The resulting suspension was extracted with EtOAc (3*900 ml), and the organic fractions combined, washed with brine (2 L), dried over $Na_2SO_4$, and concentrated in vacuo. The crude product was purified by flash chromatography (silica gel, ethyl acetate—petroleum ether 25:75) to yield target S-tert-butyl 3-cyclopropyl-3-oxo-propanethioate as a brown oil (29.5 g, purity 83%, yield: 59%).

In Step-5, the synthesis of Methyl 2-[1,3-benzodioxol-5-yl-(3-cyclopropyl-3-oxo-propanoyl)amino]-2-phenyl-acetate was performed. A 1-L round-bottom flask was charged with Methyl 2-(1,3-benzodioxol-5-ylamino)-2-phenyl-acetate (18.5 g, 61 mmol, 1.0 equiv.), S-tert-butyl 3-cyclopropyl-3-oxo-propanethioate (15.9 g, 66 mmol, 1.073 equiv.), $CF_3COOAg$ 814.6 g, 66 mmol, 1.073 equiv.), and distilled THF (400 ml), and the obtained mixture was stirred at 20° C. for 36 h (the process was controlled by TLC). The dark-brown reaction mixture was concentrated in vacuo and purified by flash chromatography (silica gel, ethyl acetate—petroleum ether 25:75 to 50:50) to yield target Methyl 2-[3-benzodioxol-5-yl-(3-cyclopropyl-3-oxo-propanoyl) amino]-2-phenyl-acetate as a brown oil (21.0 g, purity: 90%, yield: 78%).

The final Step-6 yielded the final target 1-(1,3-Benzodioxol-5-yl)-4-(cyclopropanecarbo-nyl)-3-hydroxy-2-phenyl-2H-pyrrol-5-one (Compound-1). A 500 ml round-bottom flask was charged with Methyl 2-[3-benzodioxol-5-yl-(3-cyclopropyl-3-oxo-propanoyl)amino]-2-phenyl-acetate (20.0 g; 45.5 mmol, 1.0 equiv.), CsF (6.9 g, 45.5. mmol, 1.0 equiv.), and DMF (140 ml), and the obtained mixture was stirred at 60° C. for 20 h (the process was controlled by TLC). The dark-brown reaction mixture was concentrated in vacuo and the residue was treated with 1N $H_2SO_4$ (400 ml). The obtained mixture was extracted with EtOAc (500 ml), and the organic phase was washed with brine (2*300 ml), dried over $Na_2SO_4$, and concentrated in vacuo to afford crude 1-(1,3-Benzodioxol-5-yl)-4-(cyclopropanecarbonyl)-3-hydroxy-2-phenyl-2H-pyrrol-5-one as a brown solid (19 g). The above solid was washed on filter with EtOAc until becoming colorless, affording target Compound-1 (1-(1,3-Benzodioxol-5-yl)-4-(cyclopropanecarbonyl)-3-hydroxy-2-phenyl-2H-pyrrol-5-one) as an off-white solid (5.0 g, purity: 98%, yield: 30%).

Synthesis of Compound-4 Compound-4 (4-(1,3-Benzodioxol-5-yl)pyrimidine) was synthesized by the following procedure (ChiroBlock GmbH, Wolfen, Germany). A 250 ml round-bottom flask was loaded with 1-(1,3-Benzodioxol-5-yl)ethanone (10.0 g, 60.9 mmol, 1.0 equivalent), $(EtO)_3CH$ (27 g, 183 mmol, 3.0 equivalents), $ZnCl_2$ (0.83 g, 6.1 mmol, 0.1 equivalent), $NH_4CH_3COO$ (0.4 g, 122 mmol, 2.0 equivalents) and toluene (120 ml), and the obtained mixture was stirred at reflux for 48 g and subsequently at 20° C. for 48 h (the process was controlled by TLC). The reaction mixture was quenched with saturated NaHCO3 (400 ml) and extracted with chloroform (400 ml). The organic phase was dried over $Na_2SO_4$ and concentrated in vacuo, and the resulting crude product was purified by flash chromatography (silica gel, MeOH—$CHCl_3$ (0:100 to 5:95) to yield target Com-pound-4 (4-(1,3-Benzodioxol-5-yl)pyrimidine) as an off-white solid (3.0 g, purity 97%; yield 25%).

Isolation of Neonatal Cardiomyocytes and Cell Experiments

Neonatal mouse and rat cardiomyocytes were isolated as described (Fu X, et al., J. Biol. Chem. 288, 7738-7755 (2013); Lorenz K, et al., Nature 426, 574-579 (2003)). Briefly, the hearts were dissected out from 2-3 day-old mice, atria and aorta were removed, and the hearts were transferred into sterile buffer A (137 mM NaCl, 5.36 mM KCl, 0.81 mM MgSO4, 5.55 mM dextrose, 0.44 mM KH2PO4, 0.34 mM Na2HPO4, 20 mM HEPES, 100 U/ml penicillin, 100 microg/ml streptomycin, pH 7.4). The hearts were cut into small pieces and incubated (on a magnetic stirrer) for 15 min with buffer A supplemented with 150 mg/L trypsin (Becton&Dickinson, Franklin Lakes, N.J., USA). The supernatant was discarded, and the procedure was repeated once. Thereafter the heart tissue was digested by sequential 5 min incubations with trypsin-supplemented buffer A at room temperature until the heart tissue was completely digested. Cells in the supernatants were collected by centrifugation (10 min, 700×g, at room temperature), suspended in MEM with 5% FCS, and filtered through a nylon mesh (40 microm). Fibroblasts were removed by pre-plating for 1 h at 37° C. Non-adherent cardiomyocytes were collected and cultivated in MEM (supplemented with 5% FCS and 25 mg/I BrdU). Cellular cAMP levels of isolated cardiomyocytes were determined with cAMP Enzyme Immunoassay kit (CA200, Sigma Aldrich, St. Louis, Mo., USA) after beta-adrenoceptor stimulation with 100 nM isoproterenol similarly as described (Abd Alla, J, et al., J. Biol. Chem. 291, 2583-2600 (2016)). Human embryonic kidney cells were cultivated as described (Fu X, et al., J. Biol. Chem. 288, 7738-7755 (2013)).

Histology Techniques.

For histology analyses, paraffin sections of mouse heart specimens were used. Immunohistological detection of RKIP was performed with affinity-purified, polyclonal antibodies raised in rabbit against recombinant RKIP. After antigen retrieval, sections were incubated with primary antibodies (dilution 1:200) in blocking buffer [PBS, pH 7.4, supplemented with 5% (w/v) bovine serum albumin, 0.05% Tween-20] for 1 h at 37° C. Unbound antibody was removed by three washing steps with PBS supplemented with 0.05% Tween-20. After incubation with peroxidase-conjugated secondary antibody (Dianova, Dianova GmbH, Hamburg, Germany; dilution 1:500), followed by washing steps, an enzyme substrate reaction was performed (DAB Enhanced Liquid Substrate System, Sigma-Aldrich, St. Louis, Mo., USA). Immunohistology sections were imaged with a Leica DM16000 microscope equipped with a DFC420 camera. Myocardial necrosis was determined with von Kossa stain (Calcium stain kit, modified Von Kossa No. KT028 Diagnostic Biosystems Pleasanton, Calif., USA)

Lentiviral-Mediated Down Regulation of Srsf1 by RNAi In Vivo

For the down regulation of Srsf1 expression in vivo, Tg-GRK2 mice were transduced by i.p. administration of a replication-incompetent lentivirus ($1\times10^8$ copies/mouse in PBS), which down-regulates Srsf1 by polymerase II (Pol II)-dependent expression of a pre-miRNA targeting the Srsf1 RNA by RNAi. The lentiviral expression plasmid was generated by inserting the indicated double-stranded oligonucleotides that encoded an engineered pre-miRNA sequence targeting the murine Srsf1 gene by RNAi interference into the pLenti6/V5-DEST™ GATEWAY™ Vector (INVITROGEN™, THERMO FISHER SCIENTIFIC®, Waltham, Mass., USA): miSrsf top strand 5'-TGC TGT TTA AGT CCT GCC AGC TTC CAG TTT TGG CCA CTG ACT GAC TGG AAG CTC AGG ACT TAA A-3' (SEQ ID NO: 1); and miSrsf1 bottom strand 5'-CCT GTT TAA GTC CTG AGC TTC CAG TCA GTC AGT GGC CAA AAC TGG AAG CTG GCA GGA CTT AAA C-3' (SEQ ID NO: 2). A pseudotyped lentivirus was produced by cotransfection of 293FT cells with the lentiviral plasmid and a mixture of packaging plasmids pLP1, pLP2 and pLP/VSVG (INVITROGEN™, THERMO FISHER SCIENTIFIC®, Waltham, Mass., USA). Down regulation of Srsf1 protein expression was confirmed by immunblot detection after the transduction of mice with miSrsf1-lentivirus.

Whole Genome Microarray Gene Expression Analysis

Whole genome microarray gene expression analysis of cardiac tissue from Tg-RKIP and Tg-GRK2-K220R mice was performed using Affymetrix GeneChip Mouse genome MG430 2.0 Arrays essentially as described (Abd Alla, J, et al., J. Biol. Chem. 291, 2583-2600 (2016)). GO analyses of microarray data were performed with GCOS and/or RMA-processed data using GeneSpring GX software (Agilent, Santa Clara, Calif., USA). The data were compared between two groups using the unpaired two-tailed Student's t-test. Probe sets, which were significantly up-regulated (fold change 2 relative to the respective control group and P0.01) were used for GO classification. Real-time qRT-PCR of Camk2d isoform splicing was performed with a LightCycler 480 (Roche Molecular Diagnostics, Pleasanton, Calif., USA) as described (Abd Alla, J, et al., J. Biol. Chem. 291, 2583-2600 (2016); Fu X, et al., J. Biol. Chem. 288, 7738-7755 (2013)). The following primers were used: Camk2d-forward 5'-ACG AGA AAT TTT TCA GCA GCC-3' (SEQ ID NO: 3); Camk2d-reverse-A 5'-AC AGT AGT TTG GGG CTC CAG C-3' (SEQ ID NO: 4); Camk2d-reverse-B 5'-T CAT CTG AAC ACT CGA ACT GG-3' (SEQ ID NO: 5); Camk2d-reverse-C 5'-CTC AGT TGA CTC CTT TAC CCC-3' (SEQ ID NO: 6).

Statistical Analyses

The results are presented as the means±s.d. unless otherwise specified. The P values were calculated with Student's t-test. Analysis of variance was performed for comparisons between more than two groups followed by a post-test, and statistical significance was set at a P value of <0.05 unless otherwise stated.

The invention claimed is:
1. A method for treatment of heart failure in a patient, the method comprising:
administering to the patient in need of such treatment a therapeutically effective amount of a compound according to Formula (Ia):

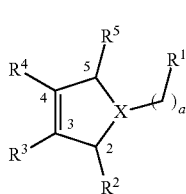

Formula (Ia)

wherein:
X is N;
a is an integer between 0 and 15;
$R^1$ is selected from the group consisting of
  (i) hydroxyl, F, Cl, Br and oxo;
  (ii) linear or branched, substituted or non-substituted $(C_{1-10})$alkyl ether, $(C_{2-10})$alkenyl ether, $(C_{2-10})$alkynyl ether and $(C_{4-10})$carbocyclic ether;
  (iii) linear or branched, substituted or non-substituted $(C_{2-10})$alkenyl and $(C_{2-10})$alkynyl;
  (iv) substituted or non-substituted $(C_{3-10})$carbocycle; and
  (v) non-substituted indazolyl, substituted or non-substituted benzimidazolyl, and substituted or non-substituted benzodioxolyl, $(C_7-C_{10})$carbo-bicycle, and substituted or non-substituted $(C_{3-6})$heterocycle having 1 to 3 heteroatoms each independently selected from N, O and S;
$R^2$ is selected from the group consisting of
  (i) hydrogen, hydroxyl, O—$R^{14}$, —O—C(=O)—$R^{14}$, F, $C_1$, Br and oxo wherein $R^{14}$ is selected from the group consisting of
    (aa) linear or branched, substituted or non-substituted $(C_{1-10})$alkyl, $(C_{2-10})$alkenyl, and $(C_{2-10})$alkynyl;
    (bb) substituted or non-substituted aromatic or non-aromatic $(C_{3-10})$carbocycle; and
    (cc) substituted or non-substituted aromatic or non-aromatic $(C_{3-6})$heterocycle having 1 to 3 heteroatoms each independently selected from N, O and S;
  (ii) linear or branched, substituted or non-substituted $(C_{1-10})$alkyl, $(C_{2-10})$alkenyl, $(C_{2-10})$alkynyl, and $(C_{3-10})$carbocycle;
  (iii) linear or branched, substituted or non-substituted $(C_{1-10})$alkyl ether, $(C_{2-10})$alkenyl ether, $(C_{2-10})$alkynyl ether and $(C_{4-10})$carbocyclic ether; and
  (iv) substituted or non-substituted $(C_{3-6})$heterocycle and $(C_7-C_{10})$carbo- or heterobicycle having 1 to 3 heteroatoms each independently selected from N, O and S;
$R^3$ is selected from the group consisting of
  (i) hydroxyl, —O—$R^{14}$, —O—C(=O)—$R^{14}$, F, $C_1$, Br and oxo, wherein $R^{14}$ is selected from the group consisting of
    (aa) linear or branched, substituted or non-substituted $(C_{1-10})$alkyl, $(C_{2-10})$alkenyl, and $(C_{2-10})$alkynyl;
    (bb) substituted or non-substituted aromatic or non-aromatic $(C_{3-10})$-carbocycle; and
    (cc) substituted or non-substituted aromatic or non-aromatic $(C_{3-6})$heterocycle having 1 to 3 heteroatoms each independently selected from N, O and S;
  (ii) linear or branched, substituted or non-substituted $(C_{1-10})$alkyl, $(C_{2-10})$alkenyl, $(C_{2-10})$alkynyl, $(C_{3-10})$carbocycle, and $(C_{3-6})$heterocycle having 1 to 3 heteroatoms each independently selected from N, O and S;
  (iii) linear or branched, substituted or non-substituted $(C_{1-10})$alkyl ether, $(C_{2-10})$alkenyl ether, $(C_{2-10})$alkynyl ether and $(C_{4-10})$carbocyclic ether;
  (iv)

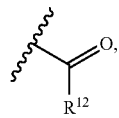

wherein $R^{12}$ is selected from the group consisting of
  (aa) hydrogen, hydroxyl, non-substituted N, F, Cl and Br;
  (bb) linear or branched, substituted or non-substituted $(C_{1-10})$alkyl, $(C_{2-10})$alkenyl, and $(C_{2-10})$alkynyl;
  (cc) substituted or non-substituted aromatic or non-aromatic $(C_{3-10})$carbocycle; and
  (dd) substituted or non-substituted aromatic or non-aromatic $(C_{3-6})$ heterocycle having 1 to 3 heteroatoms each independently selected from N, O and S; and (v)

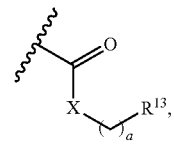

wherein X is N or C, a is an integer between 0 and 15, and $R^{13}$ is selected from the group consisting of
  (aa) hydrogen, hydroxyl, F, Cl and Br;
  (bb) linear or branched, substituted or non-substituted $(C_{1-10})$alkyl, $(C_{2-10})$alkenyl and $(C_{2-10})$alkynyl;
  (cc) substituted or non-substituted $(C_{3-6})$cycloalkyl, $(C_7-C_{10})$carbo- or heterobicycle and $(C_{3-6})$heterocycle having 1 to 3 heteroatoms each independently selected from N, O and S,
    optionally, for $R^3$, $R^{13}$ is $(C_7)$heterobicycle having 2 heteroatoms selected from N and S, substituted or non-substituted indazolyl, benzimidazolyl and benzodioxolyl, and indazolyl, benzimidazolyl and benzodioxolyl connected via position (5) or (6), via position (5) of the indazolyl and benzodioxolyl or position (6) of the benzimidazolyl; and
  (dd) linear or branched, substituted or non-substituted $(C_{1-10})$alkyl ether, $(C_{2-10})$alkenyl ether, $(C_{2-10})$alkynyl ether and $(C_{4-10})$carbocyclic ether;

wherein, if position (2) is sp³-hybridized, R² is optionally (R)- or (S)-configured;
R⁴ is hydroxyl;
R⁵ is selected from the group consisting of
  (i) hydrogen, hydroxyl, F, C₁, and Br;
  (ii) linear or branched, substituted or non-substituted (C₁₋₁₀)alkyl ether, (C₂₋₁₀)alkenyl ether, (C₂₋₁₀)alkynyl ether and (C₄₋₁₀)carbocyclic ether;
  (iii) linear or branched, substituted or non-substituted (C₁₋₁₀)alkyl, (C₂₋₁₀)alkenyl and (C₂₋₁₀)alkynyl;
  (iv) substituted or non-substituted (C₃₋₁₀)carbocycle; and
  (v) (C₃₋₆)heterocycle having 1 to 3 heteroatoms each independently selected from N, O and S, substituted or non-substituted imidazolyl and pyrazolyl, and imidazolyl and pyrazolyl connected via imidazolyl-/pyrazolyl-position-(1)-nitrogen to the rings of Formula (Ia);
wherein, if position (5) of the ring of Formula (Ia) is sp³-hybridized, R⁵ is optionally (S)- or (R)-configured;
wherein one or more of R², R³, R⁴, and R⁵ are either directly attached to the rings of Formulas (Ia) or are attached to a linker between R², R³, R⁴, and R⁵ and the rings of Formulas (Ia), wherein the linker is selected from the group consisting of linear or branched, substituted or non-substituted (C₁₋₁₀)alkyl ether, (C₂₋₁₀)alkenyl ether, (C₂₋₁₀)alkynyl ether, (C₄₋₁₀)carbocyclic ether, linear or branched, substituted or non-substituted (C₁₋₁₀)alkyl, (C₂₋₁₀)alkenyl and (C₂₋₁₀)alkynyl;
and pharmaceutically acceptable salts.

2. The method according to claim 1, wherein at least one of:
a is 0 or 1;
R¹ is selected from the group consisting of
  (i) substituted or non-substituted cyclopropyl, unsubstituted phenyl, and phenyl that is mono-substituted in para position by a substituent selected from the group consisting of H, Cl, F, Br, methyl, —(CF₃) and cyclopropyl; and
  (ii) non-substituted indazolyl, substituted or non-substituted benzimidazolyl and substituted or non-substituted benzodioxolyl, each connected via position (5) or (6); or
a combination thereof.

3. The method according to claim 1, wherein:
when R¹ is an indazolyl or benzodioxolyl, it is connected via position 6; or
when R¹ is a benzimidazolyl, it is connected via position 5.

4. The method according to claim 2, wherein:
when R¹ is an indazolyl or benzodioxolyl, it is connected via position 6; or
when R¹ is a benzimidazolyl, it is connected via position 5.

5. The method according to claim 1, wherein at least one of:
R² is selected from the group consisting of
  (i) hydrogen or oxo;
  (ii) linear or branched, substituted or non-substituted (C₁₋₅)alkyl; and
  (iii) substituted or non-substituted indazolyl, substituted or non-substituted benzimidazolyl, and substituted or non-substituted benzodioxolyl;
R³ is selected from the group consisting of
  (i) linear or branched, substituted or non-substituted (C₁₋₅)alkyl;
  (ii)

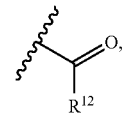

wherein R¹² is selected from the group consisting of
  (aa) N; and
  (bb) substituted or non-substituted cyclopropyl, unsubstituted phenyl, and phenyl that is mono-substituted in para position by cyclopropyl or —(CF₃) or di-substituted in meta position by cyclopropyl or —(CF₃) in each meta position; and
(iii)

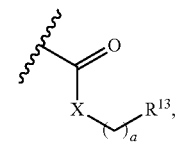

wherein X is N, a is 1 and R¹³ is selected from the group consisting of substituted or non-substituted indazolyl, benzimidazolyl and benzodioxolyl connected via position (6) or (5) of indazolyl, benzimidazolyl and benzodioxolyl, via position (5) of the indazolyl and benzodioxolyl or position (6) of the benzimidazolyl;
R⁴ is hydroxyl;
wherein R² is optionally (R)- or (S)-configured;
R⁵ is selected from the group consisting of
  (i) hydrogen;
  (ii) linear or branched, substituted or non-substituted (C₁₋₅)alkyl;
  (iii) substituted or non-substituted cyclopropyl, unsubstituted phenyl, and phenyl that is mono-substituted in para position by a substituent selected from the group consisting of H, C₁, F, Br, methyl, —(CF₃) and cyclopropyl;
  (iv) cyclopenta-2,4-dien-1-yl; and
  (v) substituted or non-substituted imidazolyl and pyrazolyl connected via the imidazolyl-/pyrazolyl-position-(1)-nitrogen to the ring of Formula (Ia);
wherein R⁵ is optionally (R)- or (S)-configured; or
a combination thereof.

6. The method according to claim 1, wherein when R² is a indazolyl, benzimidazolyl and benzodioxolyl, it is connected via position (5) or (6).

7. The method according to claim 5, wherein when R² is a indazolyl, benzimidazolyl and benzodioxolyl, it is connected via position (5) or (6).

8. The method according to claim 1, wherein the compound is a compound of Formula (Ia):

Formula (Ia)

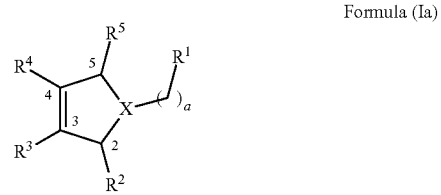

wherein X is N and a is 0, and wherein at least one of:
R¹ is selected from the group consisting of non-substituted indazolyl, substituted or non-substituted benzimidazolyl and substituted or non-substituted benzodioxolyl connected via position (6) or (5);
R² is oxo;
R³ is selected from the group consisting of
  (i) methyl; and
  (ii)

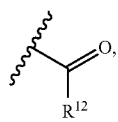

wherein R¹² is selected from the group consisting of
  (aa) N; and
  (bb) cyclopropyl and phenyl that is mono-substituted in para position by cyclopropyl or —(CF₃), or di-substituted in meta position by cyclopropyl or —(CF₃) in each meta position;
R⁴ is hydroxyl;
R⁵ is selected from the group consisting of
  (i) hydrogen;
  (ii) methyl;
  (iii) cyclopropyl and phenyl that is mono-substituted in para position by a substituent selected from the group consisting of H, Cl, F, Br, methyl, —(CF₃) and cyclopropyl;
  (iv) cyclopenta-2,4-dien-1-yl; and
  (v) imidazolyl and pyrazolyl connected via the imidazolyl-/pyrazolyl-position-(1)-nitrogen to the ring of Formula (Ia);
wherein R⁵ is optionally (R)- or (S)-configured; or
a combination thereof.

9. The method according to claim 8, wherein:
R¹ is selected from the group consisting of non-substituted indazolyl connected via position (6) of the indazolyl, substituted or non-substituted benzimidazolyl connected via position (5) of the benzimidazolyl and substituted or non-substituted benzodioxolyl connected via position (6) of the benzodioxolyl.

10. The method according to claim 1, wherein at least one of:
R¹ is selected from the group consisting of

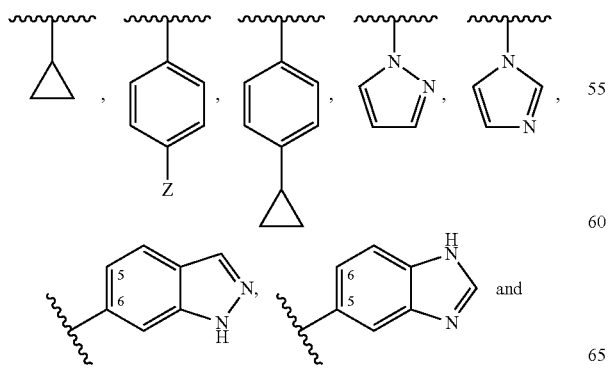

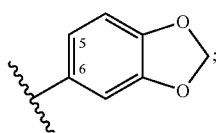

Z = H, Me, (CF₃), F, Cl, Br

R² is selected from the group consisting of hydrogen, oxo, methyl,

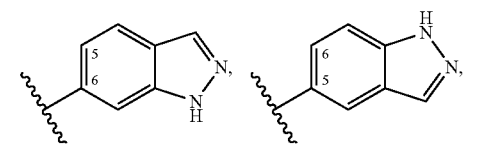

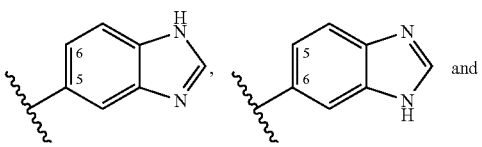

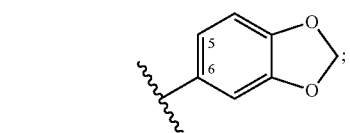

R³ is selected from the group consisting of methyl,

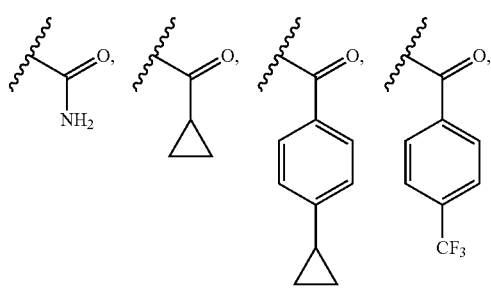

CF₃

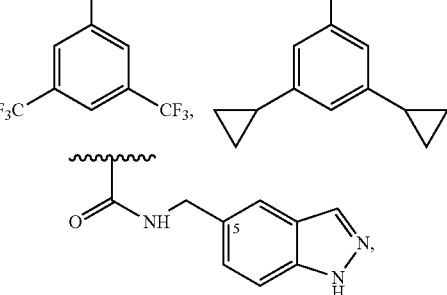

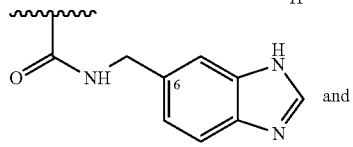

and

-continued

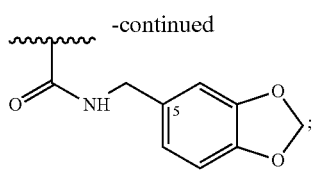

$R^4$ is hydroxyl;
a combination thereof;
wherein at least one of:
$R^2$ is optionally (R)- or (S)-configured
$R^5$ is selected from the group consisting of: hydrogen, methyl, cyclopenta-2,4-dien-1-yl,

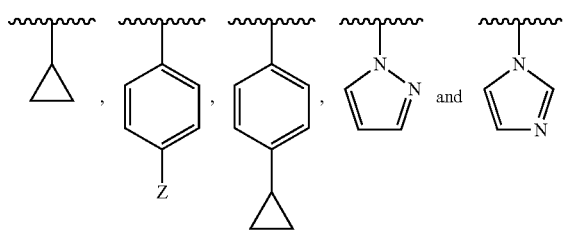

Z = H, Me, (CF$_3$), F, Cl, Br wherein $R^5$ is optionally (R)- or (S)-configured,
or a combination thereof.

11. The method according to claim 1, wherein the compound is selected from the group consisting of:
a first residue selected from the group consisting of
1-(1,3-benzodioxol-5-yl)-3-hydroxy-5-oxo-2-methyl-2H-pyrrol-4-yl,
1-(1,3-benzodioxol-5-yl)-2-cyclopropyl-3-hydroxy-5-oxo-2H-pyrrol-4-yl,
1-(1,3-benzodioxol-5-yl)-3-hydroxy-5-oxo-2H-pyrrol-4-yl,
1-(1,3-benzodioxol-5-yl)-2-(cyclopenta-2,4-dien-1-yl)-5-oxo-3-hydroxy-2H-pyrrol-4-yl,
1-(1,3-benzodioxol-5-yl)-3-hydroxy-5-oxo-2-(pyrazol-1-yl)-2H-pyrrol-4-yl,
1-(1,3-benzodioxol-5-yl)-3-hydroxy-5-oxo-2-(imidazol-1-yl)-2H-pyrrol-4-yl,
1-(1,3-benzodioxol-5-yl)-3-hydroxy-5-oxo-2-phenyl-2H-pyrrol-4-yl,
1-(1,3-benzodioxol-5-yl)-3-hydroxy-5-oxo-2-(p-tolyl)-2H-pyrrol-4-yl,
1-(1,3-benzodioxol-5-yl)-2-(4-chlorophenyl)-3-hydroxy-5-oxo-2H-pyrrol-4-yl,
1-(1,3-benzodioxol-5-yl)-2-(4-fluorophenyl)-3-hydroxy-5-oxo-2H-pyrrol-4-yl,
1-(1,3-benzodioxol-5-yl)-2-(4-bromophenyl)-3-hydroxy-5-oxo-2H-pyrrol-4-yl,
1-(1,3-benzodioxol-5-yl)-2-(4-cyclopropylphenyl)-3-hydroxy-5-oxo-2H-pyrrol-4-yl,
1-(1,3-benzodioxol-5-yl)-3-hydroxy-5-oxo-2-[4-(trifluoromethyl)phenyl]-2H-pyrrol-4-yl,
3-hydroxy-1-(1H-indazol-6-yl)-5-oxo-2-[4-(trifluoromethyl)phenyl]-2H-pyrrol-4-yl,
3-hydroxy-1-(1H-indazol-6-yl)-5-oxo-2-phenyl-2H-pyrrol-4-yl,
3-hydroxy-1-(1H-indazol-6-yl)-5-oxo-2-(p-tolyl)-2H-pyrrol-4-yl,
2-(4-chlorophenyl)-3-hydroxy-1-(1H-indazol-6-yl)-5-oxo-2H-pyrrol-4-yl,
2-(4-fluorophenyl)-3-hydroxy-1-(1H-indazol-6-yl)-5-oxo-2H-pyrrol-4-yl,
2-(4-bromophenyl)-3-hydroxy-1-(1H-indazol-6-yl)-5-oxo-2H-pyrrol-4-yl,
2-(4-cyclopropylphenyl)-3-hydroxy-1-(1H-indazol-6-yl)-5-oxo-2H-pyrrol-4-yl,
2-cyclopropyl-3-hydroxy-1-(1H-indazol-6-yl)-5-oxo-2H-pyrrol-4-yl,
3-hydroxy-1-(1H-indazol-6-yl)-5-oxo-2-methyl-2H-pyrrol-4-yl,
3-hydroxy-1-(1H-indazol-6-yl)-5-oxo-2H-pyrrol-4-yl,
3-hydroxy-1-(1H-indazol-6-yl)-5-oxo-2-(pyrazol-1-yl)-2H-pyrrol-4-yl,
2-(cyclopenta-2,4-dien-1-yl)-3-hydroxy-1-(1H-indazol-6-yl)-5-oxo-2H-pyrrol-4-yl,
3-hydroxy-2-(imidazol-1-yl)-1-(1H-indazol-6-yl)-5-oxo-2H-pyrrol-4-yl,
1-(1H-benzimidazol-5-yl)-3-hydroxy-5-oxo-2-dimethyl-2H-pyrrol-4-yl,
1-(1H-benzimidazol-5-yl)-2-cyclopropyl-3-hydroxy-5-oxo-2H-pyrrol-4-yl,
1-(1H-benzimidazol-5-yl)-3-hydroxy-5-oxo-2-(pyrazol-1-yl)-2H-pyrrol-4-yl,
1-(1H-benzimidazol-5-yl)-3-hydroxy-5-oxo-2H-pyrrol-4-yl,
1-(1H-benzimidazol-5-yl)-3-hydroxy-5-oxo-2-(imidazol-1-yl)-2H-pyrrol-4-yl,
1-(1H-benzimidazol-5-yl)-2-(cyclopenta-2,4-dien-1-yl)-3-hydroxy-5-oxo-2H-pyrrol-4-yl,
1-(1H-benzimidazol-5-yl)-2-(4-fluorophenyl)-3-hydroxy-5-oxo-2H-pyrrol-4-yl,
1-(1H-benzimidazol-5-yl)-3-hydroxy-5-oxo-2-[4-(trifluoromethyl)phenyl]-2H-pyrrol-4-yl,
1-(1H-benzimidazol-5-yl)-3-hydroxy-5-oxo-2-phenyl-2H-pyrrol-4-yl,
1-(1H-benzimidazol-5-yl)-3-hydroxy-5-oxo-2-(p-tolyl)-2H-pyrrol-4-yl,
1-(1H-benzimidazol-5-yl)-2-(4-chlorophenyl)-3-hydroxy-5-oxo-2H-pyrrol-4-yl,
1-(1H-benzimidazol-5-yl)-2-(4-bromophenyl)-3-hydroxy-5-oxo-2H-pyrrol-4-yl,
1-(1H-benzimidazol-5-yl)-2-(4-cyclopropylphenyl)-3-hydroxy-5-oxo-2H-pyrrol-4-yl,
wherein the numbering of the 2H-pyrrole ring is as follows:

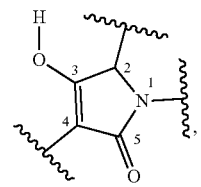 [SMILES: *C1=C(O)C(*)N(*)C1=O]

covalently bound to a second residue selected from the group consisting of methyl,

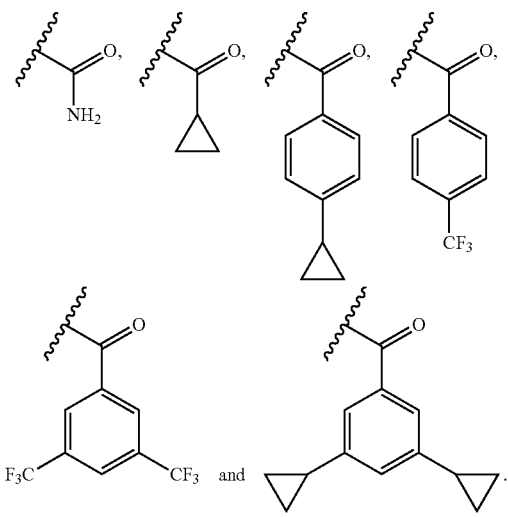

12. The method according to claim 1, wherein the compound is

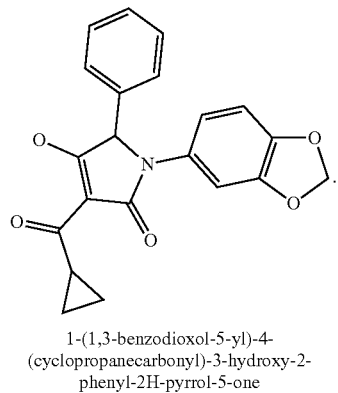 [SMILES: O=C(C1=C(O)C(c2ccccc2)N(c2ccc3c(c2)OCO3)C1=O)C1CC1]

1-(1,3-benzodioxol-5-yl)-4-
(cyclopropanecarbonyl)-3-hydroxy-2-
phenyl-2H-pyrrol-5-one

13. The method according to claim 1, wherein the compound is administered as a pharmaceutical composition comprising the compound.

14. The method according to claim 1, wherein the treatment of heart failure reduces the risk of one or more of the following
(i) cardiovascular mortality and/or morbidity under conditions of essential hypertension and/or chronic hypertension;
(ii) cardiovascular disease-induced ageing;
(iii) cardiovascular mortality and/or morbidity under conditions of left ventricular dysfunction and signs of heart failure after recent myocardial infarction;
(iv) cardiovascular mortality and/or morbidity under conditions of chronic heart failure and left ventricular dysfunction;
(v) cardiovascular mortality and/or morbidity under conditions of dilated cardiomyopathy;
(vi) cardiovascular mortality and/or morbidity under conditions of left ventricular dysfunction;
(vii) cardiovascular mortality and/or morbidity under conditions of cardiomyocyte necrosis;
(viii) cardiovascular mortality and/or morbidity under conditions of cardiac fibrosis;
(ix) cardiomyocyte necrosis and/or dilated cardiomyopathy, optionally under conditions with increased risk for ischemic cardiac diseases and ischemic heart damage, optionally as a consequence of cardiovascular risk factors selected from the group consisting of hypertension, atherosclerosis, chronic and acute stress, depression, diabetes mellitus, chronic heart failure, angina pectoris, atrial fibrillation, chronic renal failure and aging; and
(x) cardiomyocyte necrosis and/or dilated cardiomyopathy in patients with previous events selected from the group consisting of acute cardiovascular disease, myocardial infarction, ischemic heart disease, angina pectoris, atrial fibrillation, decompensated and chronic heart failure, and cerebrovascular stroke,
wherein the patient is a mammalian patient.

15. The method according to claim 1, wherein the treatment of heart failure reduces the risk of a nephropathy, a nephropathy caused by at least one of: hypertension, renal artery stenosis, ischemia, diabetes, toxic agents, or a combination thereof.

16. The method of claim 1, wherein the compound has the chemical structure:

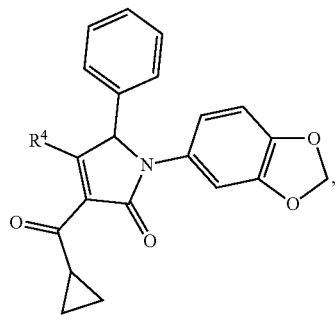

wherein:
$R^4$ is selected from the group consisting of hydroxyl, —O—$R^{14}$, and —O—C(=O)—$R^{14}$; and
$R^{14}$ is selected from the group consisting of:
(aa) linear or branched, substituted or non-substituted ($C_{1-10}$)alkyl, ($C_{1-5}$)alkyl, methyl, ethyl, propyl, ($C_{2-10}$)alkenyl, and ($C_{2-10}$)alkynyl;
(bb) substituted or non-substituted aromatic or non-aromatic ($C_{3-10}$)carbocycle, ($C_{3-6}$) Cycloalkyl, ($C_3$) carbocycle, ($C_6$)carbocycle, and phenyl that is mono-substituted in para position by ($C_3$)carbocycle or —($CF_3$) or di-substituted in meta position by ($C_3$)carbocycle or —($CF_3$); and
(cc) substituted or non-substituted aromatic or non-aromatic ($C_{3-6}$)heterocycle having 1 to 3 heteroatoms each independently selected from N, O and S.

17. The method of claim 1, wherein:
$R^1$ is selected from non-substituted indazolyl, substituted or non-substituted benzimidazolyl, and substituted or non-substituted benzodioxolyl;
$R^2$ is selected from non-substituted indazolyl, substituted or non-substituted benzimidazolyl, and substituted or non-substituted benzodioxolyl; or
a combination thereof.

\* \* \* \* \*

SEQUENCE LISTING

```
<160> NUMBER OF SEQ ID NOS: 10

<210> SEQ ID NO 1
<211> LENGTH: 64
<212> TYPE: DNA
<213> ORGANISM: Artificial Sequence
<220> FEATURE:
<223> OTHER INFORMATION: miSrsf top strand

<400> SEQUENCE: 1
tgctgtttaa gtcctgccag cttccagttt tggccactga ctgactggaa gctcaggact    60
```

```
taaa                                                                64
```

<210> SEQ ID NO 2
<211> LENGTH: 64
<212> TYPE: DNA
<213> ORGANISM: Artificial Sequence
<220> FEATURE:
<223> OTHER INFORMATION: miSrsf1 bottom strand

<400> SEQUENCE: 2

```
cctgtttaag tcctgagctt ccagtcagtc agtggccaaa actggaagct ggcaggactt    60
aaac                                                                64
```

<210> SEQ ID NO 3
<211> LENGTH: 21
<212> TYPE: DNA
<213> ORGANISM: Artificial Sequence
<220> FEATURE:
<223> OTHER INFORMATION: Camk2d-forward primer

<400> SEQUENCE: 3

```
acgagaaatt tttcagcagc c                                             21
```

<210> SEQ ID NO 4
<211> LENGTH: 21
<212> TYPE: DNA
<213> ORGANISM: Artificial Sequence
<220> FEATURE:
<223> OTHER INFORMATION: Camk2d-reverse-A primer

<400> SEQUENCE: 4

```
acagtagttt ggggctccag c                                             21
```

<210> SEQ ID NO 5
<211> LENGTH: 21
<212> TYPE: DNA
<213> ORGANISM: Artificial Sequence
<220> FEATURE:
<223> OTHER INFORMATION: Camk2d-reverse-B primer

<400> SEQUENCE: 5

```
tcatctgaac actcgaactg g                                             21
```

<210> SEQ ID NO 6
<211> LENGTH: 21
<212> TYPE: DNA
<213> ORGANISM: Artificial Sequence
<220> FEATURE:
<223> OTHER INFORMATION: Camk2d-reverse-C primer

<400> SEQUENCE: 6

```
ctcagttgac tcctttaccc c                                             21
```

<210> SEQ ID NO 7
<211> LENGTH: 248
<212> TYPE: PRT
<213> ORGANISM: Homo sapiens

<400> SEQUENCE: 7

```
Met Ser Gly Gly Gly Val Ile Arg Gly Pro Ala Gly Asn Asn Asp Cys
1               5                   10                  15

Arg Ile Tyr Val Gly Asn Leu Pro Pro Asp Ile Arg Thr Lys Asp Ile
            20                  25                  30

Glu Asp Val Phe Tyr Lys Tyr Gly Ala Ile Arg Asp Ile Asp Leu Lys
```

```
                35                  40                  45
Asn Arg Arg Gly Gly Pro Pro Phe Ala Phe Val Glu Phe Glu Asp Pro
 50                  55                  60

Arg Asp Ala Glu Asp Ala Val Tyr Gly Arg Asp Gly Tyr Asp Tyr Asp
 65                  70                  75                  80

Gly Tyr Arg Leu Arg Val Glu Phe Pro Arg Ser Gly Arg Gly Thr Gly
                 85                  90                  95

Arg Gly Gly Gly Gly Gly Gly Gly Ala Pro Arg Gly Arg Tyr
            100                 105                 110

Gly Pro Pro Ser Arg Arg Ser Glu Asn Arg Val Val Val Ser Gly Leu
            115                 120                 125

Pro Pro Ser Gly Ser Trp Gln Asp Leu Lys Asp His Met Arg Glu Ala
            130                 135                 140

Gly Asp Val Cys Tyr Ala Asp Val Tyr Arg Asp Gly Thr Gly Val Val
145                 150                 155                 160

Glu Phe Val Arg Lys Glu Asp Met Thr Tyr Ala Val Arg Lys Leu Asp
                165                 170                 175

Asn Thr Lys Phe Arg Ser His Glu Gly Glu Thr Ala Tyr Ile Arg Val
                180                 185                 190

Lys Val Asp Gly Pro Arg Ser Pro Ser Tyr Gly Arg Ser Arg Ser Arg
            195                 200                 205

Ser Arg Ser Arg Ser Arg Ser Arg Ser Asn Ser Arg Ser Arg
            210                 215                 220

Ser Tyr Ser Pro Arg Arg Ser Arg Gly Ser Pro Arg Tyr Ser Pro Arg
225                 230                 235                 240

His Ser Arg Ser Arg Ser Arg Thr
                245

<210> SEQ ID NO 8
<211> LENGTH: 15
<212> TYPE: PRT
<213> ORGANISM: Artificial Sequence
<220> FEATURE:
<223> OTHER INFORMATION: phospho-containing peptide of SRSF1 identfied
      in Nano-LC-ESI-MS/MS analysis
<220> FEATURE:
<221> NAME/KEY: MOD_RES
<222> LOCATION: (9)..(9)
<223> OTHER INFORMATION: PHOSPHORYLATION
<220> FEATURE:
<221> NAME/KEY: MOD_RES
<222> LOCATION: (11)..(11)
<223> OTHER INFORMATION: PHOSPHORYLATION

<400> SEQUENCE: 8

Arg Val Lys Val Asp Gly Pro Arg Ser Pro Ser Tyr Gly Arg Ser
 1               5                  10                  15

<210> SEQ ID NO 9
<211> LENGTH: 13
<212> TYPE: PRT
<213> ORGANISM: Artificial Sequence
<220> FEATURE:
<223> OTHER INFORMATION: phospho-containing peptide of SRSF1 identfied
      in Nano-LC-ESI-MS/MS analysis
<220> FEATURE:
<221> NAME/KEY: MOD_RES
<222> LOCATION: (7)..(7)
<223> OTHER INFORMATION: PHOSPHORYLATION
<220> FEATURE:
<221> NAME/KEY: MOD_RES
<222> LOCATION: (9)..(9)
<223> OTHER INFORMATION: PHOSPHORYLATION
```

```
<400> SEQUENCE: 9

Lys Val Asp Gly Pro Arg Ser Pro Ser Tyr Gly Arg Ser
1               5                   10

<210> SEQ ID NO 10
<211> LENGTH: 236
<212> TYPE: PRT
<213> ORGANISM: Artificial Sequence
<220> FEATURE:
<223> OTHER INFORMATION: carboxyl terminal domain of human GRK2, amino
      acids 454-689

<400> SEQUENCE: 10

Arg Ser Leu Asp Trp Gln Met Val Phe Leu Gln Lys Tyr Pro Pro Pro
1               5                   10                  15

Leu Ile Pro Pro Arg Gly Glu Val Asn Ala Ala Asp Ala Phe Asp Ile
            20                  25                  30

Gly Ser Phe Asp Glu Glu Asp Thr Lys Gly Ile Lys Leu Leu Asp Ser
        35                  40                  45

Asp Gln Glu Leu Tyr Arg Asn Phe Pro Leu Thr Ile Ser Glu Arg Trp
    50                  55                  60

Gln Gln Glu Val Ala Glu Thr Val Phe Asp Thr Ile Asn Ala Glu Thr
65                  70                  75                  80

Asp Arg Leu Glu Ala Arg Lys Lys Ala Lys Asn Lys Gln Leu Gly His
                85                  90                  95

Glu Glu Asp Tyr Ala Leu Gly Lys Asp Cys Ile Met His Gly Tyr Met
            100                 105                 110

Ser Lys Met Gly Asn Pro Phe Leu Thr Gln Trp Gln Arg Arg Tyr Phe
        115                 120                 125

Tyr Leu Phe Pro Asn Arg Leu Glu Trp Arg Gly Glu Gly Glu Ala Pro
    130                 135                 140

Gln Ser Leu Leu Thr Met Glu Glu Ile Gln Ser Val Glu Glu Thr Gln
145                 150                 155                 160

Ile Lys Glu Arg Lys Cys Leu Leu Leu Lys Ile Arg Gly Gly Lys Gln
                165                 170                 175

Phe Ile Leu Gln Cys Asp Ser Asp Pro Glu Leu Val Gln Trp Lys Lys
            180                 185                 190

Glu Leu Arg Asp Ala Tyr Arg Glu Ala Gln Gln Leu Val Gln Arg Val
        195                 200                 205

Pro Lys Met Lys Asn Lys Pro Arg Ser Pro Val Val Glu Leu Ser Lys
    210                 215                 220

Val Pro Leu Val Gln Arg Gly Ser Ala Asn Gly Leu
225                 230                 235
```